(12) United States Patent
Ohmoto et al.

(10) Patent No.: US 7,872,133 B2
(45) Date of Patent: Jan. 18, 2011

(54) TRICYCLIC HETEROCYCLE COMPOUND

(75) Inventors: Kazuyuki Ohmoto, Mishima-gun (JP);
Masashi Kato, Mishima-gun (JP);
Takeshi Matsushita, Mishima-gun (JP);
Seishi Katsumata, Mishima-gun (JP);
Junichiro Manako, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 1086 days.

(21) Appl. No.: 10/561,973

(22) PCT Filed: Jun. 22, 2004

(86) PCT No.: PCT/JP2004/009071

§ 371 (c)(1),
(2), (4) Date: Dec. 22, 2005

(87) PCT Pub. No.: WO2004/113300

PCT Pub. Date: Dec. 29, 2004

(65) Prior Publication Data

US 2006/0154944 A1 Jul. 13, 2006

(30) Foreign Application Priority Data

Jun. 23, 2003 (JP) .............................. 2003-178436

(51) Int. Cl.
*A61K 31/437* (2006.01)
*A61K 31/438* (2006.01)
*C07D 401/02* (2006.01)
*C07D 401/14* (2006.01)

(52) U.S. Cl. .......................................... 546/18; 514/278

(58) Field of Classification Search ....................... None
See application file for complete search history.

(56) References Cited

U.S. PATENT DOCUMENTS

| | | | |
|---|---|---|---|
| 3,959,470 | A | 5/1976 | Mashkovsky et al. |
| 4,336,260 | A | 6/1982 | Payne et al. |
| 5,095,020 | A | 3/1992 | Hulkenberg et al. |
| 5,403,851 | A | 4/1995 | D'Orlando et al. |
| 6,043,252 | A | 3/2000 | Bombrun |
| 6,048,868 | A | 4/2000 | Fourtillan et al. |
| 6,350,757 | B1 | 2/2002 | Goldstein et al. |
| 7,368,444 | B2 | 5/2008 | Seko et al. |
| 7,403,851 | B2 | 7/2008 | Kaufman et al. |
| 2002/0010189 | A1 | 1/2002 | Sui et al. |
| 2004/0072833 | A1 | 4/2004 | Nakai et al. |
| 2004/0116458 | A1 | 6/2004 | Sawyer et al. |
| 2004/0122035 | A1 | 6/2004 | Orme et al. |
| 2004/0132735 | A1 | 7/2004 | Troxler et al. |
| 2004/0147542 | A1 | 7/2004 | Sawyer et al. |
| 2004/0152736 | A1 | 8/2004 | Chackalamannil et al. |
| 2008/0114012 | A1 | 5/2008 | Ohmoto et al. |

FOREIGN PATENT DOCUMENTS

| | | |
|---|---|---|
| EP | 0 740 668 B1 | 7/1998 |
| EP | 1 438 973 A1 | 7/2004 |
| EP | 1475368 A1 | 11/2004 |
| FR | 1 431 702 | 4/1976 |
| GB | 1444980 A | 8/1976 |
| JP | 3-287586 A | 12/1991 |
| JP | 09-508113 A | 8/1997 |
| JP | 9-511246 A | 11/1997 |
| JP | 2001-072679 A | 3/2001 |
| JP | 2002-517500 A | 6/2002 |
| JP | 2002-524564 A | 8/2002 |
| JP | 2004-501919 A | 1/2004 |
| JP | 2004-518729 A | 6/2004 |
| JP | 2004-518730 A | 6/2004 |
| JP | 2004-532852 A | 10/2004 |
| WO | 95-26723 A1 | 10/1995 |
| WO | 97/43287 A1 | 11/1997 |
| WO | 99-64420 A1 | 12/1999 |
| WO | 00-15639 A1 | 3/2000 |
| WO | 01-87038 A2 | 11/2001 |
| WO | 2004-113300 A1 | 12/2001 |
| WO | 02-00657 A2 | 1/2002 |
| WO | 02-053565 A1 | 7/2002 |
| WO | 02-064590 A2 | 8/2002 |
| WO | 02-064591 A2 | 8/2002 |
| WO | 02-081471 A1 | 10/2002 |
| WO | 02/088123 A1 | 11/2002 |

(Continued)

OTHER PUBLICATIONS

Dorwald F. A. Side Reactions in Organic Synthesis, 2005, Wiley: VCH, Weinheim p. IX of Preface.*

(Continued)

*Primary Examiner*—Rita J Desai
(74) *Attorney, Agent, or Firm*—Sughrue Mion, PLLC

(57) ABSTRACT

The present invention relates to the compound represented by formula (I)

$$A-X-Y-Z-B \quad (I)$$

(wherein A is a cyclic group which may have a substituent(s); X is a single bond or a spacer; Y is a single bond or a spacer; Z is a single bond or a spacer; B is a hydrocarbon group which may have a substituent(s) or a cyclic group which may have a substituent(s)), a salt thereof, a solvate thereof or a prodrug thereof. The compound represented by formula (I), a salt thereof, a solvate thereof or a prodrug thereof is useful for preventive and/or therapeutic agent for a disease caused by stress.

5 Claims, No Drawings

FOREIGN PATENT DOCUMENTS

| | | |
|---|---|---|
| WO | 03-068753 A1 | 8/2003 |
| WO | 03/099821 A1 | 12/2003 |
| WO | 2005/070930 A2 | 8/2005 |
| WO | 2005/089764 A1 | 9/2005 |

OTHER PUBLICATIONS

Wolff, Manfred E. "Burger's Medicinal Chemistry, 5ed, Part I", John Wiley & Sons, 1995, pp. 975-977.*

Banker (Modern Pharmaceutics) Banker, G.S. et al, "Modern Pharmaceutics, 3ed.", Marcel Dekker, New York, 1996, pp. 451 and 596.*

International Search Report dated Oct. 5, 2004.

Haishan Wang, et al., "Synthesis and Evaluation of Tryprostatin B and Demethoxyfumitremorgin C Analogues", Journal of Medicinal Chemistry, 2000, vol. 43, No. 8, pp. 1577-1585.

Brian E. Love, et al., "Preparation of 1-Aryl-β-carbolines", Journal of Organic Chemistry, 1994, vol. 59, No. 11, pp. 3219-3222.

B. Bonaz, Y. Taché, "Water-Avoidance Stress-Induced c-fos Expression In The Rat Brain and Stimulation of Fecal Output: Role of Corticotropin-Releasing Factor", Brain Research, 624, pp. 21-28 (1994).

Michikazu Abe, Ken-Ichi Saito, "Reduction of Wrap Restraint Stress-Induced Defecation by MKC-242, a Novel Benzodioxan Derivative, via 5-HT 1A-Receptor Agonist Action in Rats", Jpn. J. Pharmacol. 77, pp. 211-217 (1998).

Cain, M et al., "Beta-Carbolines: Synthesis and Neurochemical and Pharmacological Actions on Brain Benzodiazepine Receptors", Journal of Medicinal Chemistry, Sep. 1982, pp. 1081-1091, vol. 25, No. 9.

Supplementary European Search Report dated Jul. 29, 2009.

Cain, M et al., "Beta-Carbolines: Synthesis and Neurochemical and Pharmacological Actions on Brain Benzodiazepine Receptors", Journal of Medicinal Chemistry, Sep. 1982, pp. 1081-1091, vol. 25, No. 9, American Chemical Society, Washington, US.

Limbach, et al.; "Addition of Indole to Methyl 2-Chloro-2-cyclopropylideneacetate en Route to Spirocyclopropanated Analogues of Demethoxyfumiremorgine C and Tadalafil"; Eur. J. Org. Chem., 2005, vol. 3, pp. 610 to 617.

L.N. Yakhontov, et al.; "Azaindol derivatives XXXVIII. Normal and abnormal course of reactions during 12-aza-b-carboline synthesis"; Khimiya Geterotsiklicheskikh Soedinenii, 1970, vol. 11, pp. 1550-1553.

European Search Report Dated Dec. 3, 2009 for Application No. 05820106.2-2101/1829874 (PCT/JP2005/023450).

International Search Report (PCT/ISA/210) for PCT/JP2005/023450, dated Apr. 11, 2006.

Chemical Abstracts Service; C. Balsamini, et al.; "N-benzhydryltryptamines and 1, 1-diphenyltetrandrobeta-carbolines: synthesis, x-ray crystal structure and benzodiazepine receptor affinity" XP002556789; retrieved from STN Database accession No. 1989:526474; ISSN: 0014-827X; 1989; 1 page in total.

* cited by examiner

TRICYCLIC HETEROCYCLE COMPOUND

This is a national stage application under 35 U.S.C. §371 of PCT/JP2004/009071 filed on Jun. 22, 2004, which claims priority from Japanese paten application 2003-178436 filed on Jun. 23, 2003, all of which are incorporated herein by reference.

TECHNICAL FIELD

The present invention relates to a novel tricyclic heterocyclic ring compound useful for preventing and/or treating for a disease caused by stress, process for preparation thereof and use.

BACKGROUND ART

In 1977, mitochondrial benzodiazepine receptor (hereinafter, it is abbreviated as MBR.) was identified as a receptor that is different from a benzodiazepine binding site in $GABA_A$ receptor to which benzodiazepines (Science, 198, 849-851 (1977), Proc. Natl. Acad. Sci., 89, 3805-3809 (1977)). Though a physiological function is not necessarily clarified, it has been reported to get involved in steroid synthesis, the differentiation and proliferation of cells, and the immune function modulation, etc. In peripheral tissue, there are MBRs in immune system cells such as red blood cell, platelet, monocyte, and macrophages besides adrenal cortex, heart, smooth muscle, kidney, lung, testis, and in central nervous system in plexus chorioideus, pineal body, olfactory bulb, cerebral cortex, and hippocampus, etc. Cells expressing MBRs in central nervous system have mainly been known to glial cells. They have been used as a marker of gliosis so that the MBR expression level increases along with the neurodegenerative disease such as Alzheimer's disease, cerebral ischemia, multiple scleosis, and Huntington's disease, etc.

There are MBRs in mitochondrial outer membrane, which transport cholesterol from intracellular to the internal membrane of mitochondria that is the active site of P-450scc. Steroid synthesized in the brain is called as neurosteroid. Cholesterol, which is the steroid precursor, is converted into pregnenolone metabolized with side-chain cleavage enzyme P-450scc. This process is the first process of Steroid production system. However, it has been indicated that this transport process was the rate-determining process in steroid production system rather than metabolism with P-450scc. It has been thought that the neurosteroid content in the brain could be adjusted if the function of MBRs could be regulated. Actually, it has been reported that a diazepam binding inhibitor (hereinafter, it may be abbreviated as DBI.), which was identified as an endogenous ligand of a benzodiazepine binding site in $GABA_A$ receptor and MBRs, promoted the pregnenolone synthesis at mitochondrial fraction derived from rat brain and glioma cells.

It has been reported that DBI content in hippocampus increased by loading sound stressor to rat and DBI concentration in cerebrospinal fluid of patients with depressed mode rose. Therefore, it is expected that the amount of neurosteroid production can increase under stress condition. As experiment results supporting this, it has been reported that the various neurosteroid content in the brain increased by loading stressors to rats, such as forced swimming, foot shock, carbon dioxide exposure and constraint and so on.

Neurosteroids regulate the function of various receptors and ion channels positively or negatively according to the types thereof. For example, though pregnenolone sulfate and dehydroepiandrosterone sulfate control the function of $GABA_A$ receptor, progesterone, allopregnenolone and tetrahydroxycorticosterone activate it. In addition, though pregnenolone sulfate also controls the function of AMPA/kainate-type glutamate receptor, glycine receptor, and voltage-dependent calcium channel, activates NMDA-type glutamate receptor. Additionally, progesterone controls the function of acetylcholine receptor as well as glycine receptor. Further, though dehydroepiandrosterone sulfate activates the function of a receptor, progesterone control adversely. Thus, it has been thought that as a result of balance between an excitatory signaling system and an inhibitory signaling system was collapsed by neurosteroid content in the brain varying under stress condition, the various stress-related diseases could be caused by changes of activities in nerve system, immune system and endocrine system which were regulated by these nerve systems. Further, considering it has been reported that pregnenolone sulfate reinforced NMDA-induced cell death in cultured hippocampal nerve cells and caused delayed cell death with DNA fragmentation in neural retina cells, it is suggested that there is possibility that pregnenolone sulfate at least partly takes part in the degeneration of hippocampus CA3 field under stress condition.

As mentioned above, the disrupted balance between an excitatory signaling system and an inhibitory signaling system caused by stressor load can be improved to the desirable balanced condition by the increase or the inhibition of neurosteroid production, which is useful for prevention or treatment for stress-related diseases. Therefore, it is expected that the compounds having affinity for MBRs are extremely useful for prevention and/or treatment for these diseases, if they are supplied.

The problem in the present invention that the compounds having affinity for MBRs can be supplied as preventive and/or therapeutic agent for diseases caused by stress.

As therapeutic agent for stress-related diseases, the compounds represented by formula (A)

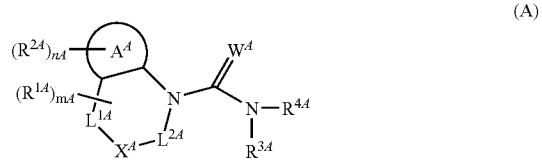

(A)

(wherein ring$A^A$ is C5-8 mono-cyclic carbocylic ring or 5-8 membered mono-heterocyclic ring having 1-2 nitrogen atom(s), 1-2 oxygen atom(s) and/or a sulfur atom; $X^A$ is $-CH_2-$, $-O-$, $-S-$, etc.; $L^{1A}$ and $L^{2A}$ are each independently single bond, C1-4 alkylene or C2-4 alkenylene.; $R^{1A}$ and $R^{2A}$ are each independently C1-8 alkyl, etc.; mA and nA is 0 or an integer of 1 to 4; $R^{3A}$ is hydrogen atom, ring$B^A$, etc.; $R^{4A}$ is hydrogen atom, C1-8 alkyl, etc.; $W^A$ is oxygen atom or sulfur atom.), or a pharmaceutically acceptable salt thereof has been known (see, WO03/068753).

In addition, as tri-cyclic compound (β-carboline derivative), the compounds represented by formula (B)

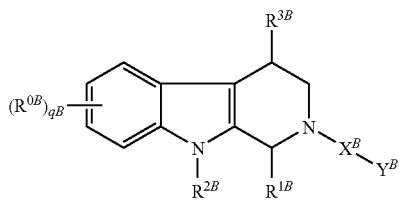

(wherein $R^{0B}$ is halogen atom, C1-6 alkyl, etc.; $R^{1B}$ is aryl which may be substituted, etc.; $R^{2B}$ is hydrogen atom, C1-6 alkyl, etc.; $R^{3B}$ is hydrogen atom, C1-6 alkyl, aryl, etc.; $X^B$ is C(=O), SO$_2$, C(=O)NR$^{aB}$, etc.; Y is (CH$_2$)$_{nB}$ aryl, etc.; nB is 0-4.), a pharmaceutically acceptable salt thereof or a solvate thereof has been known as phosphodiesterase inhibitor (see, WO02/064591).

DISCLOSURE OF THE INVENTION

As a result of the present inventors made further investigation to find out the compound having the affinity for MBRs, they found out that the compounds in the present invention represented by formula (I) accomplished the purpose and completed the present invention.

That is, the present invention relates to the followings:

1. A compound represented by formula (I)

A-X—Y—Z—B    (I)

wherein A is a cyclic group which may have a substituent(s); X, Y and Z are each independently a single bond or a spacer of which main chain has an atom number of 1-3; and B is a hydrocarbon group which may have a substituent(s) or a cyclic group which may have a substituent(s), a salt thereof, an N-oxide thereof, a solvate thereof or a prodrug thereof.

2. The compound according to the above-mentioned 1, which is represented by formula (I-1)

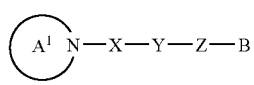

wherein ringA$^1$ is a di-, tri-, or tetra-nitrogen-containing heterocyclic ring, the other symbols have the same meanings as those defined in the above-mentioned 1, and wherein ringA$^1$ is not 2,3,4,5-tetrahydro-1H-1-benzazepine, 1,2,3,4,5,6-hexahydro-1-benzazepine, 2,3,4,5-tetrahydro-1,5-benzoxazepine, 6,7,8,9-tetrahydro-5H-pylid[2,3-d]azepine or 5,6,7,8-tetrahydro-4H-thieno[3,2-d]azepine.

3. The compound according to the above-mentioned 2, wherein ringA$^1$ is a tri-, or tetra-nitrogen-containing heterocyclic ring.

4. The compound according to the above-mentioned 3, which is represented by formula (I-2)

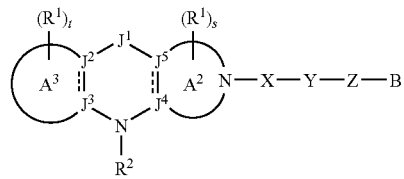

wherein ringA$^1$ is a mono-nitrogen-containing heterocyclic ring; ringA$^3$ is a mono-carbocyclic ring or mono-heterocyclic ring; plural R$^1$s are each independently a substituent, and when R$^1$s are plural, two R$^1$s may be together to form cyclic group which may have a substituent(s); R$^2$ is a hydrogen atom or a substituent; t and s are each independently 0 or an integer of 1-5, and the sum of t and s is 5 or less; J$^1$ is a single bond, a carbon atom which may have a substituent(s), a nitrogen atom which may have a substituent(s), an oxygen atom or a sulfur atom which may be oxidized; J$^2$, J$^3$, J$^4$ and J$^5$ are each independently a carbon atom or a nitrogen atom, 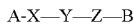 is a single bond or a double bond, and the other symbols have the same meanings as those defined in the above-mentioned 1.

5. The compound according to the above-mentioned 4, which is represented by formula (I-3)

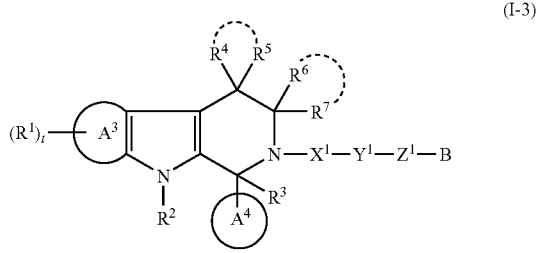

wherein R$^3$, R$^4$, R$^5$, R$^6$ and R$^7$ are each independently a hydrogen atom or a substituent, and R$^4$ and R$^5$, and/or R$^6$ and R$^7$ may be together with their binding carbon atom to form a cyclic group which may have a substituent(s); ringA$^4$ is a cyclic group which may have a substituent(s); X$^1$ and Z$^1$ are each independently a single bond, C1-3 alkylene which may have a substituent(s), C2-3 alkenylene which may have a substituent(s) or C2-3 alkynylene which may have a substituent(s); Y$^1$ is —C(=O)—, —C(=S)—, —C(=O)NR$^{103}$—, —SO$_2$—, —C(=O)O— or SO$_2$NR$^{103}$—, in which R$^{103}$ is a hydrogen atom or a substituent, the sum of the number of substituents represented by R$^1$, R$^3$, R$^4$, R$^5$, R$^6$ and R$^7$ is 4 or less, and the other symbols have the same meanings as those defined in the above-mentioned 1 or 4.

6. The compound according to the above-mentioned 5, wherein R$^4$ and R$^5$ are simultaneously substituents, or R$^4$ and R$^5$ are together with their binding carbon atom to form a cyclic group which may have a substituent(s).

7. The compound according to the above-mentioned 5, wherein R$^3$ is a substituent.

8. The compound according to the above-mentioned 5, wherein R$^6$ and R$^7$ are simultaneously substituents, or R$^6$ and $R^7$ are together with their binding carbon atom to form a cyclic group which may have a substituent(s).

9. The compound according to the above-mentioned 5, wherein $R^3$ is a mono-heterocyclic ring.

10. The compound according to the above-mentioned 5, wherein B is a C3-10 mono-, or di-carbocyclic ring which may have a substituent(s) or a 3-10 membered mono-, or di-heterocyclic ring which may have a substituent(s).

11. The compound according to the above-mentioned 5, wherein ring$A^4$ is a C3-10 mono-, or di-carbocyclic ring which may have a substituent(s) or a 3-10 membered mono-, or di-heterocyclic ring which may have a substituent(s).

12. The compound according to the above-mentioned 5, wherein $Y^1$ is —C(=O)— or —C(=O)NR$^{103}$—.

13. The compound according to the above-mentioned 4, which is selected from
(1) N-(3,5-dimethylphenyl)-1,3,4,9-tetrahydro-2H-β-carboline-2-carboxamide,
(2) N-(3-methylphenyl)-1,3,4,9-tetrahydro-2H-β-carboline-2-carboxamide,
(3) N-(3,5-dimethylphenyl)-6-methoxy-1,3,4,9-tetrahydro-2H-β-carboline-2-carboxamide,
(4) 6-methoxy-N-(3-methylphenyl)-1,3,4,9-tetrahydro-2H-β-carboline-2-carboxamide,
(5) 6-methoxy-N-[2-(trifuloromethyl)phenyl]-1,3,4,9-tetrahydro-2H-β-carboline-2-carboxamide,
(6) N-(3,5-dichlorophenyl)-6-methoxy-1,3,4,9-tetrahydro-2H-β-carboline-2-carboxamide,
(7) 1-(3-fluorophenyl)-N-phenyl-1,3,4,9-tetrahydro-2H-β-carboline-2-carboxamide,
(8) 1-(3-fluorophenyl)-N-(3-methylphenyl)-1,3,4,9-tetrahydro-2H-β-carboline-2-carboxamide,
(9) N-(3,5-dimethylphenyl)-1-(3-fluorophenyl)-1,3,4,9-tetrahydro-2H-β-carboline-2-carboxamide,
(10) 2-acetyl-1-(3-fluorophenyl)-2,3,4,9-tetrahydro-1H-β-carboline,
(11) 2-({[5-(trifluoromethyl)pyridin-2-yl]thio}acetyl)-2,3,4,9-tetrahydro-1H-β-carboline,
(12) 2-{[(2,5-dimethoxyphenyl)thio]acetyl}-2,3,4,9-tetrahydro-1H-β-carboline,
(13) 6-methoxy-1-(trifluoromethyl)-2-({[5-(trifluoromethyl)pyridin-2-yl]thio}acetyl)-2,3,4,9-tetrahydro-1H-β-carboline,
(14) 2-{[(2,5-dimethoxyphenyl)thio]acetyl}-6-methoxy-1-(trifluoromethyl)-2,3,4,9-tetrahydro-1H-β-carboline,
(15) 6-methoxy-N-(3-methylphenyl)-1-(trifluoromethyl)-1,3,4,9-tetrahydro-2H-β-carboline-2-carboxamide,
(16) N-(3,5-dimethylphenyl)-1-(3-fluorophenyl)-1,9-dihydrospiro[β-carboline-4,1'-cyclopropane]-2(3H)-carboxamide,
(17) rac-(1R,3S)—N-(3,5-dimethylphenyl)-1-(3-fluorophenyl)-3-methyl-1,3,4,9-tetrahydro-2H-β-carboline-2-carboxamide,
(18) rac-(1R,3R)—N-(3,5-dimethylphenyl)-1-(3-fluorophenyl)-3-methyl-1,3,4,9-tetrahydro-2H-β-carboline-2-carboxamide,
(19) N-(3,5-dimethylphenyl)-1-(3-fluorophenyl)-6-(trimethylsilyl)-1,3,4,9-tetrahydro-2H-β-carboline-2-carboxamide,
(20) N-(3,5-dimethylphenyl)-1-(3-fluorophenyl)-4,4-dimethyl-1,3,4,9-tetrahydro-2H-β-carboline-2-carboxamide,
(21) 2-acetyl-1-(3-fluorophenyl)-1,2,3,9-tetrahydrospiro[β-carboline-4,1'-cyclopropane],
(22) 2-(benzylsulfonyl)-1-(3-fluorophenyl)-2,3,4,9-tetrahydro-1H-β-carboline,
(23) rac-(1R,3R)-2-acetyl-1-(3-fluorophenyl)-3-methyl-2,3,4,9-tetrahydro-1H-β-carboline,
(24) methyl 1-(3-fluorophenyl)-3,3-dimethyl-1,3,4,9-tetrahydro-2H-β-carboline-2-carboxylate, and
(25) N-(3,5-dimethylphenyl)-8-(3-fluorophenyl)-5,6,8,9-tetrahydro-7H-pyrido[4',3':4,5]pyrrolo[2,3-b]pyridine-7-carboxamide.

14. A pharmaceutical composition comprising the compound represented by formula (I) according to the above-mentioned 1, a salt thereof, an N-oxide thereof, a solvate thereof or a prodrug thereof.

15. The pharmaceutical composition according to the above-mentioned 14, which is a preventive and/or therapeutic agent for a mitochondrial benzodiazepine receptor mediated disease.

16. The pharmaceutical composition according to the above-mentioned 15, wherein the mitochondrial benzodiazepine receptor mediated disease is a disease caused by stress.

17. The pharmaceutical composition according to the above-mentioned 16, wherein the disease caused by stress is a central nervous system disease caused by stress, a respiratory system disease caused by stress and/or a digestive system disease caused by stress.

18. The pharmaceutical composition according to the above-mentioned 17, wherein the central nervous system disease caused by stress is anxiety-related disease, sleep disorder, depression and/or epilepsy; a respiratory system disease caused by stress is asthma; or the digestive system disease caused by stress is irritable bowel syndrome.

19. A preventive and/or therapeutic agent for a central nervous system, a respiratory system disease and/or a digestive disease, comprising the compound represented by formula (I) according to the above-mentioned 1, a salt thereof, an N-oxide thereof, a solvate thereof or a prodrug thereof.

20. A pharmaceutical composition combining the compound represented by formula (I) according to the above-mentioned 1, a salt thereof, an N-oxide thereof, a solvate thereof or a prodrug thereof, and one kind or more kind selected from antianxiety drugs, antidepressant drugs, antiparkinson drugs, therapeutic drugs for schizophrenia, antiepileptic drugs, therapeutic drugs for asthma, therapeutic drugs for peptic ulcer, adjustive drugs for gastrointestinal function, antidiarrheals, evacuants, antihypertensive drugs, antiarrhythmic drugs, inotropic drugs and therapeutic drugs for urination disorder.

21. A method for prevention and/or treatment for a mitochondrial benzodiazepine receptor mediated disease in mammals, which comprises administering to a mammal an effective amount of the compound represented by formula (I) according to the above-mentioned 1, a salt thereof, an N-oxide, a solvate or a prodrug thereof.

22. Use of the compound represented by formula (I) according to the above-mentioned 1, a salt thereof, an N-oxide thereof, a solvate thereof or a prodrug thereof for preparing a preventive and/or therapeutic agent for a mitochondrial benzodiazepine receptor mediated disease.

In the specification, "cyclic group in cyclic group which may have a substituent(s)" represented by A means, for example, carbocyclic ring and heterocyclic ring and so on. Carbocyclic ring means, for example, C3-20 mono-, bi-, trior tetra-aromatic carbocyclic ring partially or fully saturated, spiro-linked bi-, tri-, or tetra-carbocyclic ring, and bridged bi-, tri-, or tetra-carbocyclic ring and so on. C3-20 mono-, bi-, tri- or tetra-aromatic carbocyclic ring partially or fully saturated means, for example, benzene, azulene, naphthalene, phenanthrene, anthracene, triphenylene, chrysene, naphthacene, pleiadene, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, pentalene, perhydropentalene, perhydroazulene, indene, perhydroindene, indane, dihydronaphthalene, tetrahydronaphthalene, perhydronaphthalene, heptalene, perhydroheptalene, biphenylene, as-indacene, s-indacene, acenaphthylene, acenaphtene, fluorene, phenalene, fluoranthene, acephenanthrylene, aceanthrylene, pyrene and so on. Spiro-linked bi-, tri-, or tetra-carbocyclic ring, and bridged bi-, tri-, or tetra-carbocyclic ring mean, for example, spiro[4.4]nonane, spiro[4.5]decane, spiro[5.5]undecane, bicyclo[2.2.1]heptane, bicyclo[2.2.1]hepta-2-ene, bicyclo[3.1.1]heptane, bicyclo[3.1.1]hepta-2-ene, bicyclo[2.2.2]octane, bicyclo[2.2.2]octa-2-ene, adamantane, noradamantane and so on. Heterocyclic ring means, for example, 3-20 membered mono-, bi-, tri-, or tetraaromatic heterocyclic ring optionally partially or fully saturated containing 1 to 5 hetero atom(s) selected from oxygen, nitrogen and/or sulfur atom(s) and so on. 3-20 membered mono-, bi-, tri-, or tetra-aromatic heterocyclic ring optionally partially or fully saturated containing 1 to 5 hetero atom(s) selected from oxygen, nitrogen and/or sulfur atom(s) means, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, pyrrolopyridine, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, pyridonaphthyridine, pyrazoloisoquinoline, pyrazolonaphthyridine, pyrimidoindole, indolizinoindole, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, tetrahydropyrrolopyridine, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, tetrapyridonaphthyridine, tetrahydro-β-carboline (e.g., 2,3,4,9-tetrahydro-1H-β-carboline, etc.), tetrahydropyridopyrrolopyridine (e.g., 6,7,8,9-tetrahydro-5H-pyrido[4',3':4,5]pyrrolo[2,3-b]pyridine, 2,3,4,9-tetrahydro-1H-pyrido[4',3':4,5]pyrrolo[2,3-c]pyridine, 6,7,8,9-tetrahydro-5H-pyrido[3',4':4,5]pyrrolo[2,3-c]pyridine, 6,7,8,9-tetrahydro-5H-pyrido[4',3':4,5]pyrrolo[3,2-b]pyridine, etc.), 6,7,8,9-tetrahydro-5H-pyrido[4',3':4,5]pyrrolo[2,3-d]pyrimidine, dihydroazepinoindole, hexahydroazepinoindole (e.g., 1,2,3,4,5,10-hexahydroazepino[3,4-b]indole, 1,2,3,4,5,6-hexahydroazepino[4,3-b]indole, etc.), tetrahydropyrazoloisoquinoline, tetrahydropyrazolonaphthyridine, dihydroazepinoindazole, hexahydroazepinoindazole, dihydropyrazolopyridoazepine, hexahydropyrazolopyridoazepine, tetrahydropyrimidoindole, dihydrothiazinoindole, tetrahydrothiazinoindole, dihydrooxazinoindole, tetrahydrooxazinoindole, hexahydroindolizinoindole, dihydroindolobenzdiazepine, octahydroindoloquinolizine, hexahydroimidazopyridoindole, hexahydropyrrolothiazepinoindole, dioxolane, dioxane, dithiolane, dithiane, dioxaindan, benzodioxane, chroman, benzodithiolane, benzodithiane, azaspiro[4.4]nonane, oxazaspiro[4.4]nonane, oxazaspiro[2.5]octane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxaspiro[5.5]undecane, 2,3,4,9-tetrahydrospiro[β-carboline-1,1'-cyclopentane], 1,2,3,9-tetrahydrospiro[β-carboline-4,1'-cyclopropane], 1,2,4,9-tetrahydrospiro[β-carboline-3,1'-cyclopropane], 1,2,3,9-tetrahydrospiro[β-carboline-4,1'-cyclobutane], 1,2,4,9-tetrahydrospiro[β-carboline-3,1'-cyclobutane], 1,2,3,9-tetrahydrospiro[β-carboline-4,1'-cyclopentane], 1,2,4,9-tetrahydrospiro[β-carboline-3,1'-cyclopentane], azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane and so on.

In the specification, "substituent in cyclic group which may have a substituent(s)" represented by A means, for example, (1) hydrocarbon group which may have a substituent(s), (2) carbocyclic ring which may have a substituent(s), (3) heterocyclic ring which may have a substituent(s), (4) hydroxyl which may have a substituent(s), (5) mercapto which may have a substituent(s), (6) amino which may have a substituent(s), (7) carbamoyl which may have a substituent(s), (8) sulfamoyl which may have a substituent(s), (9) carboxyl, (10) alkoxycarbonyl (e.g., C1-6 alkoxycarbonyl, etc., such as methoxycarbonyl, ethoxycarbonyl, propoxycarbonyl, isopropoxycarbonyl, tert-butoxycarbonyl and so on.), (11) sulfo (—SO$_3$H), (12) sulfino, (13) phosphono, (14) nitro, (15) cyano, (16) amidino, (17) imino, (18) dihydroborono (—B(OH)$_2$), (19) halogen atom (e.g., fluorine, chlorine, bromine, iodine), (20) alkylsufinyl (e.g., C1-4 alkylsulfinyl, etc., such as methylsulfinyl, ethylsulfinyl and so on.), (21) aromatic ring sulfinyl (e.g., C6-10 aromatic ring sulfinyl, etc., such as phenylsulfinyl and so on.), (22) alkylsulfonyl (e.g., C1-4 alkylsulfonyl, etc., such as methylsulfonyl, ethylsulfonyl and so on.), (23) aromatic ring sulfonyl (e.g., C6-10 aromatic ring sulfonyl, etc., phenylsulfonyl, etc.), (24) oxo, (25) thioxo, (26) (C1-6 alkoxyimino)methyl (e.g., (methoxyimino)methyl, etc.), (27) acyl (28) formyl, (29) alkyl substituted with hydroxyl which may have a substituent(s), (30) alkyl substituted with mercapto which may have a substituent(s), (31) alkyl substituted with amino which may have a substituent(s), (32) (alkyl which may have a substituent(s))-oxycarbonyl, (33) tri(C1-6 alkyl)silyl (e.g., trimethylsilyl, etc.) and so on. These optional substituents may be substituted 1-5 at the replaceable position.

Hydrocarbon group in "(1) hydrocarbon group which may have a substituent(s)" means, for example, alkyl, alkenyl, alkynyl, alkylidene, alkenylidene and so on.

Alkyl means, for example, straight-chain or branched-chain C1-20 alkyl and so on, such as methyl, ethyl, n-propyl, isopropyl, n-butyl, isobutyl, sec-butyl, tert-butyl, n-pentyl, neopentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, etc. Straight-chain or branched-chain C1-8 alkyl is preferred. Straight-chain or branched-chain C1-6 alkyl is more preferred.

Alkenyl means, for example, straight-chain or branched-chain C2-8 alkenyl and so on, such as ethenyl, propenyl, butenyl, pentenyl, hexenyl, heptenyl, octenyl, etc. Straight-chain or branched-chain C2-6 alkenyl is preferred.

Alkynyl means, for example, straight-chain or branched-chain C2-8 alkynyl and so on, such as ethynyl, propynyl, butynyl, pentynyl, hexynyl, heptynyl, octynyl, etc. Straight-chain or branched-chain C2-6 alkynyl is preferred.

Alkylidene means, for example, straight-chain or branched-chain C1-8 alkylidene and so on, such as methylidene, ethylidene, propylidene, butylidene, pentylidene, hexylidene, heptylidene, octylidene, etc.

Alkenylidene means, for example, straight-chain or branched-chain C2-8 alkenylidene and so on, such as ethenylidene, propenylidene, butenylidene, pentenylidene, hexenylidene, heptenylidene, octenylidene, etc.

Here, substituent of hydrocarbon group means, for example, hydroxyl, mercapto, amino, carboxyl, nitro, cyano, mono- or di-C1-6 alkylamino (e.g., methylamino, ethylamino, propylamino, dimethylamino, diethylamino, etc.), N-aromatic ring amino (e.g., N-phenylamino, etc.), N-aromatic ring-N-alkylamino (e.g., N-phenyl-N-methylamino, N-phenyl-N-ethylamino, N-phenyl-N-propylamino, N-phenyl-N-butylamino, N-phenyl-N-pentylamino, N-phenyl-N-hexylamino, etc.), acylamino, N-acyl-N-alkylamino, C1-6 alkoxy (e.g., methoxy, ethoxy, propoxy, isopropoxy, hexyloxy, etc.), C3-7 cycloalkyl-C1-6 alkoxy (e.g., cyclohexylmethyloxy, cylcopentylethyloxy, etc.), C3-7 cycloalkyloxy (e.g., cylcohexyloxy, etc.), C7-15 aralkyloxy (e.g., benzyloxy, phenethyloxy, phenylpropyloxy, naphthylmethyloxy, naphthylethyloxy, etc.), phenoxy, C1-6 alkoxycarbonyl (e.g., methoxycarbonyl, ethoxycarbonyl, tert-butoxycarbonyl, etc.), C1-6 alkylcarbonyloxy (e.g., acetoxy, ethylcarbonyloxy, etc.), C1-6 alkylthio (e.g., methylthio, ethylthio, propylthio, butylthio, pentylthio, hexylthio, etc.), halogen atom (e.g., florine, chlorine, bromine, iodine, etc.), alkylsulfonyl (e.g., C1-4 alkylsulfonyl, etc., such as methylsulfonyl, ethylsulfonyl and so on.), aromatic ring sulfonyl (e.g., C6-10 aromatic ring sulfonyl, etc., such as phenylsulfonyl and so on.), carbamoyl which may have a substituent(s) (e.g carbamoyl without substituent, N-mono-C1-6 alkylcarbamoyl (e.g., N-methylcarbamoyl, N-ethylcarbamoyl, N-propylcarbamoyl, N-isopropylcarbamoyl, N-butylcarbamoyl, etc.), N,N-di-C1-6 alkylcarbamoyl (e.g., N,N-dimethylcarbamoyl, N,N-diethylcarbamoyl, N,N-dipropylcarbamoyl, N,N-dibutylcarbamoyl, etc.), piperidin-1-ylcarbonyl, etc.), acyl, carbocyclic ring which may have a substituent(s), and heterocyclic ring which may have a substituent(s), etc. These optional substituents may be substituted 1-4 at the replaceable position. Here, alkyl in N-acyl-N-alkylamino means, for example, straight-chain or branched-chain C1-6 alkyl and so on, such as methyl, ethyl, n-propyl, isopropyl, n-butyl, isobutyl, sec-butyl, tert-butyl, pentyl, hexyl, etc. In addition, acyl in acyl, acylamino and N-acyl-N-alkylamino has the same meanings as that of the after-mentioned (27) acyl. Additionally, carbocylic ring which may have a substituent(s) and heterocyclic ring which may have a substituent(s) have the same meanings as that of the after-mentioned "(2) carbocyclic ring which may have a substituent(s)", and "(3) heterocyclic ring which may have a substituent(s)".

Carbocylcic ring in "(2) carbocyclic ring which may have a substituent(s)" has the same meanings as that of carbocyclic ring represented by the above-mentioned A. Here, substituent of carbocyclic ring means, for example, straight-chain or branched-chain C1-8 alkyl optionally with hydroxyl (e.g., methyl, ethyl, n-propyl, isopropyl, n-butyl, isobutyl, sec-butyl, tert-butyl, pentyl, hexyl, heptyl, octyl, etc.), straight-chain or branched-chain C2-6 alkenyl (e.g., ethenyl, propenyl, butenyl, pentenyl, hexenyl, etc.), straight-chain or branched-chain C2-6 alkynyl (e.g., ethynyl, propynyl, butynyl, pentynyl, hexynyl, etc.), hydroxyl, straight-chain or branched-chain C1-6 alkoxy (e.g., methoxy, ethoxy, propoxy, isopropoxy, butoxy, isobutyloxy, tert-butoxy, pentyloxy, hexyloxy, etc.), mercapto, straight-chain or branched-chain C1-6 alkylthio (e.g., methylthio, ethylthio, propylthio, isopropythio, butylthio, isobutylthio, tert-butylthio, pentylthio, hexylthio, etc.), amino, mono- or di-C1-6 alkylamino (e.g., methylamino, ethylamino, propylamino, isopropylamino, butylamino, isobutylamino, tert-butylamino, pentylamino, hexylamino, dimethylamino, diethylamino, dipropylamino, N-methyl-N-ethylamino, etc.), halogen atom (e.g., florine, chlorine, bromine, iodine), cyano, nitro, carboxyl, straight-chain or branched-chain C1-6 alkoxycarbonyl (e.g., methoxycarbonyl, ethoxycarbonyl, tert-butoxycarbonyl, etc.), straight-chain or branched-chain C1-6 alkylcarbonyloxy (e.g., acetoxy, ethylcarbonyloxy, etc.), trihalomethyl (e.g., tirfluoromethyl, etc.), trihalomethoxy (e.g., trifluoromethoxy, etc.), trihalomethylthio (e.g., trifluoromethylthio, etc.), dihalomethylthio (e.g., difluoromethylthio, etc.), oxo, carbocyclic ring (it has the same meanings as that of carbocyclic ring represented by the above-mentioned A), heterocyclic ring (it has the same meanings as that of heterocyclic ring represented by the above-mentioned A) and so on. These optional substituents may be substituted 1-4 at the replaceable position.

Heterocyclic ring in "(3) heterocyclic ring which may have a substituent(s)" has the same meanings as that of heterocyclic ring represented by the above-mentioned A. Here, substituent of heterocyclic ring has the same meanings as that of substituent in the above-mentioned (2) carbocyclic ring which may have a substituent(s).

Substituent in "(4) hydroxyl which may have a substituent(s)", "(5) mercapto which may have a substituent(s)" and "(6) amino which may have a substituent(s)" means, for example, hydrocarbon group which may have a substituent(s) (it has the same meanings as that of the above-mentioned "(1) hydrocarbon group which may have a substituent(s)".), carbocyclic ring which may have a substituent(s) (it has the same meanings as that of the above-mentioned "(2) carbocyclic ring which may have a substituent(s)".), heterocyclic ring which may have a substituent(s) (it has the same meanings as that of the above-mentioned "(3) heterocyclic ring which may have a substituent(s)".), alkylsulfonyl (e.g., C1-4 alkylsulfonyl, etc., such as methylsulfonyl, ethylsulfonyl and so on.), aromatic ring sulfonyl (e.g., C6-10 aromatic ring sulfonyl, etc., such as phenylsulfonyl and so on.), acyl (it has the same meanings as that of the after-mentioned "(27) acyl".), (alkyl which may have a substituent(s))-oxycarbonyl (it has the same meanings as that of the after-mentioned "(32) (alkyl which may have a substituent(s))-oxycarbonyl".) and so on.

"(7) carbamoyl which may have a substituent(s)" means, for example, carbamoyl without substituent, N-mono-C1-6 alkylcarbamoyl (e.g., N-methylcarbamoyl, N-ethylcarbamoyl, N-propylcarbamoyl, N-isopropylcarbamoyl, N-butylcarbamoyl, etc.), N,N-di-C1-6 alkylcarbamoyl (e.g., N,N-dimethylcarbamoyl, N,N-diethylcarbamoyl, N,N-dipropylcarbamoyl, N,N-dibutylcarbamoyl, etc.), piperidin-1-ylcarbonyl and so on.

"(8) sulfamoyl which may have a substituent(s)" means, for example, sulfamoyl without substituent, N-mono-C1-6 alkylsulfamoyl (e.g., N-methylsulfamoyl, N-ethylsulfamoyl, N-propylsulfamoyl, N-isopropylsulfamoyl, N-butylsulfamoyl, etc.), N,N-di-C1-6 alkylsulfamoyl (e.g., N,N-dimethylsulfamoyl, N,N-diethylsulfamoyl, N,N-dipropylsulfamoyl, N,N-dibutylsulfamoyl, etc.) and so on.

"(27) acyl" means, for example, alkylcarbonyl which may have a substituent(s) (wherein alkyl which may have a substituent(s) has the same meanings as that of "alkyl which may have a substituent(s)" in the above-mentioned "(1) hydrocarbon group which may have a substituent(s)".), alkenylcarbonyl which may have a substituent(s) (wherein alkenyl which may have a substituent(s) has the same meanings as that of "alkenyl which may have a substituent(s)" in the above-mentioned "(1) hydrocarbon group which may have a substituent(s)".), alkynylcarbonyl which may have a substituent(s) (wherein alkynyl which may have a substituent(s) has the same meanings as that of "alkynyl which may have a substituent(s)" in the above-mentioned "(1) hydrocarbon group which may have a substituent(s)".), carbocyclic ring carbonyl which may have a substituent(s) (wherein carbocyclic ring which may have a substituent(s) has the same meanings as that of the above-mentioned "(2) carbocyclic ring which may have a substituent(s)".), heterocyclic ring carbonyl which may have a substituent(s) (wherein heterocyclic ring which may have a substituent(s) has the same meanings as that of the above-mentioned "(3) heterocyclic ring which may have a substituent(s)".) and so on.

Hydroxyl which may have a substituent(s) in "(29) alkyl substituted with hydroxyl which may have a substituent(s)" has the same meanings as that of the above-mentioned "(4) hydroxyl which may have a substituent(s)". Mercapto which may have a substituent(s) in "(30) alkyl substituted with mercapto which may have a substituent(s)" has the same meanings as that of the above-mentioned "(5) mercapto which may have a substituent(s)". Amino which may have a substituent(s) in "(31) alkyl substituted with amino which may have a substituent(s)" has the same meanings as that of the above-mentioned "(6) amino which may have a substituent(s)". In addition, alkyl in "(29) alkyl substituted with hydroxyl which may have a substituent(s)", "(30) alkyl substituted with mercapto which may have a substituent(s)" and "(31) alkyl substituted with amino which may have a substituent(s)" means, for example, straight-chain or branched-chain C1-6 alkyl and so on, such as methyl, ethyl, n-propyl, isopropyl, n-butyl, isobutyl, sec-butyl, tert-butyl, pentyl, hexyl, etc.

Alkyl which may have a substituent(s) in "(32) (alkyl which may have a substituent(s))-oxycarbonyl" has the same meanings as that of "alkyl which may have a substituent(s)" in "(1) hydrocarbon group which may have a substituent(s)".

In the specification, "cyclic group" in cyclic group which may have a substituent(s) represented by B has the same meanings as that of cyclic group in "cyclic group which may have a substituent(s)" represented by A.

In the specification, "substituent" in cyclic group which may have a substituent(s) represented by B has the same meanings as that of substituent in "cyclic group which may have a substituent(s)" represented by A.

In the specification, "hydrocarbon group which may have a substituent(s)" represented by B has the same meanings as that of "(1) hydrocarbon group which may have a substituent(s) which is substituent" in the above-mentioned "cyclic group which may have a substituent(s)" represented by A.

In the specification, a "spacer of which main chain has an atom number of 1-3" represented by X means the distance that 1-3 atom(s) of main chain is(are) connected. Here, the "atom number of main chain" is counted to be minimal. The "spacer of which main chain has an atom number of 1-3" includes, for example, divalent group selected from C1-3 alkylene which may have a substituent(s), C2-3 alkenylene which may have a substituent(s), C2-3 alkynylene which may have a substituent(s), nitrogen atom which may have a substituent(s), (—NH—), —C(=O)—, —C(=S)—, —O—, —S—, —SO—, —SO$_2$—. Here, C1-3 alkylene means, for example, methylene, ethylene, propylene, etc. C2-3 alkenylene means, for example, ethenylene, propenylene, etc. C2-3 alkynylene means, for example, ethynylene, propynylene, etc. In addition, substituent in alkylene, alkenylene and alkynylene and substituent of nitrogen atom have the same meanings as "substituent" in the above-mentioned cyclic group which may have a substituent(s) represented by A. Concretely, it means, for example, —CR$^{101}$R$^{102}$—, —NR$^{103}$—, —C(=O)—, —C(=S)—, —O—, —S—, NR$^{103}$C(=O), —C(=O)NR$^{103}$—, —SO$_2$—, —C(=O)O—, —SO$_2$NR$^{103}$— (wherein R$^{101}$, R$^{102}$, R$^{103}$ are hydrogen atom, or have the same meanings as "substituent" in the above-mentioned cyclic group which may have a substituent(s) represented by A.) and so on.

In the specification, a "spacer of which main chain has an atom number of 1-3" represented by Y has the same meanings as a "spacer of which main chain has an atom number of 1-3" represented by the above-mentioned X.

In the specification, a "spacer of which main chain has an atom number of 1-3" represented by Z has the same meanings as a "spacer of which main chain has an atom number of 1-3" represented by the above-mentioned X.

In the specification, "di-nitrogen-containing heterocyclic ring" in di-nitrogen-containing heterocyclic ring which may have a substituent(s) represented by ringA$^1$ means, for example, 4-15 membered di-aromatic heterocyclic ring which may be partially or fully saturated containing at least one nitrogen atom, additionally which may contain 1 to 4 hetero atom(s) selected from oxygen atom, nitrogen atom and/or sulfur atom(s) and so on. 3-15 membered di-aromatic heterocyclic ring which may be partially or fully saturated containing at least one nitrogen atom, additionally which may contain 1 to 4 hetero atom(s) selected from oxygen atom, nitrogen atom and/or sulfur atom(s) means, for example, indole, isoindole, indazole, purine, pyrrolopyridine, benzimidazole, benzazepine, benzodiazepine, benzotriazole, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, tetrahydropyrrolopyridine, dihydrocinnoline, tetrahydrocinnoline, perhydrocinnoline, dihydrobenzoxazine, dihydrobenzothiazine, pyrazinomorpholine, dihydrobenzoxazol, perhydrobenzoxazol, dihydrobenzothiazol, perhydrobenzothiazol, dihydrobenzimidazole, perhydrobenzimidazole, dihydrobenzazepine, tetrahydrobenzazepine, dihydrobenzodiazepine, tetrahydrobenzodiazepine, tetrahydrobenzoxazepine, azaspiro[4.4]nonane, oxazaspiro[4.4]nonane, oxazaspiro[2.5]octane, azaspiro[4.5]decane, oxazaspiro[4.5]decane, azaspiro[5.5]undecane, azabicyclo[2.2.1]heptane, azabicyclo[3.1.1]heptane, azabicyclo[3.2.1]octane and so on.

In the specification, "substituent" in di-nitrogen-containing heterocyclic ring which may have a substituent(s) represented by ringA$^1$ has the same meanings as substituent in "cyclic ring which may have a substituent(s)" represented by the above-mentioned A.

In the specification, "tri-nitrogen-containing heterocyclic ring" in tri-nitrogen-containing heterocyclic ring which may have a substituent(s) represented by ringA$^1$ means, for example, 5-15 membered tri-aromatic heterocyclic ring which may be partially or fully saturated containing at least one nitrogen atom, additionally which may contain 1 to 4 hetero atom(s) selected from oxygen atom, nitrogen atom and/or sulfur atom(s) and so on. 5-15 membered tri-aromatic heterocyclic ring which may be partially or fully saturated containing at least one nitrogen atom, additionally which may contain 1 to 4 hetero atom(s) selected from oxygen atom, nitrogen atom and/or sulfur atom(s) means, for example, carbazole, β-carboline, phenothiazine, phenoxazine, perimidine, pyrazoloisoquinoline, pyrazolonaphthylidine, pyrimidoindole, dihydrocarbazole, tetrahydrocarbazole, perhydrocarbazole, dihydroacridine, perhydroacridine, tetrapyridonaphthylidine, tetrahydro-β-carboline (e.g., 2,3,4, 9-tetrahydro-1H-β-carboline, etc.), tetrahydropyridopyrrolopyridine (e.g., 6,7,8,9-tetrahydro-5H-pyrido[4',3':4,5]pyrrolo[2,3-b]pyridine, 2,3,4,9-tetrahydro-1H-pyrido[4',3':4,5]pyrrolo[2,3-c]pyridine, 6,7,8,9-tetrahydro-5H-pyrido[3',4':4,5]pyrrolo[2,3-c]pyridine, 6,7,8,9-tetrahydro-5H-pyrido[4',3':4,5]pyrrolo[3,2-b]pyridine, etc.), 6,7,8,9-tetrahydro-5H-pyrido[4',3':4,5]pyrrolo[2,3-d]pyrimidine, dihydroazepinoindole, hexahydroazepinoindole (e.g., 1,2,3,4,5,10-hexahydroazepino[3,4-b]indole, 1,2,3,4,5,6-hexahydroazepino[4,3-b]indole, etc.), tetrahydropyrazoloisoquinoline, tetrahydropyrazolonaphthylidine, dihydroazepinoindazole, hexahydroazepinoindazole, dihydropyrazolopyridoazepine, hexahydropyrazolopyridoazepine, tetrahydropyrimidoindole, dihydrothiazinoindole, tetrahydrothiazinoindole, dihydrooxazinoindole, tetrahydroxazinoindole and so on.

In the specification, "substituent" in tri-nitrogen-containing heterocyclic ring which may have a substituent(s) represented by ringA$^1$ has the same meanings as substituent in "cyclic ring which may have a substituent(s)" represented by the above-mentioned A.

In the specification, "tetra-nitrogen-containing heterocyclic ring" in tetra-nitrogen-containing heterocyclic ring which may have a substituent(s) represented by ringA$^1$ means, for example, 6 to 20 membered tetra-aromatic heterocyclic ring which may be partially or fully saturated containing at least one nitrogen atom, additionally which may contain 1 to 4 hetero atom(s) selected from oxygen atom, nitrogen atom and/or sulfur atom(s) and so on. 6 to 20 membered tetra-aromatic heterocyclic ring which may be partially or fully saturated containing at least one nitrogen atom, additionally which may contain 1 to 4 hetero atom(s) selected from oxygen atom, nitrogen atom and/or sulfur atom(s) means, for example, indolizinoindole, hexahydroindolizinoindole, dihydroindolobenzodiazepine, octahydroindoloquinolizine, hexahydroimidazopyridoinodole, hexahydropyrrolothiazepinoindole, 2,3,4,9-tetrahydrospiro[β-carboline-1,1'-cyclopentane], 1,2,3,9-tetrahydrospiro[β-carboline-4,1'-cyclopropane], 1,2,4,9-tetrahydrospiro[β-carboline-3,1'-cyclopropane], 1,2,3,9-tetrahydrospiro[β-carboline-4,1'-cyclobutane], 1,2,4,9-tetrahydrospiro[β-carboline-3,1'-cyclobutane], 1,2,3,9-tetrahydrospiro[β-carboline-4,1'-cyclopentane], 1,2,4,9-tetrahydrospiro[β-carboline-3,1'-cyclopentane] and so on.

In the specification, "substituent" in tetra-nitrogen-containing heterocyclic ring which may have a substituent(s) represented by ringA$^1$ has the same meanings as substituent in "cyclic ring which may have a substituent(s)" represented by the above-mentioned A.

In the specification, mono-nitrogen-containing heterocyclic ring represented by ringA$^2$ or ringA$^3$ means, for example, 3 to 10 membered mono-aromatic heterocyclic ring which may be partially or fully saturated containing at least one nitrogen atom, additionally which may contain 1 to 4 hetero atom(s) selected from oxygen atom, nitrogen atom and/or sulfur atom(s) and so on. 3 to 10 membered mono-aromatic heterocyclic ring means, for example, pyrrole, imidazole, triazole, pyrazole, pyrroline, imidazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrooxazole, dihydroisoxazole, dihydrothiazole, dihydroisothiazole, dihydrofurazan, dihydrooxazine, dihydrooxazepine, tetrahydrooxazepine, dihydrooxadiazepine, tetrahydrooxadiazepine, dihydrothiazine, dihydrothiazepine, tetrahydrothiazepine, dihydrothiadiazepine, tetrahydrothiadiazepine and so on.

As ring represented by ringA², 5 to 7 membered mono-nitrogen-containing heterocyclic ring is preferred. Concretely, it includes 5 to 7 membered mono-aromatic heterocyclic ring which may be partially or fully saturated containing at least one nitrogen atom, additionally which may contain 1 to 2 hetero atom(s) selected from oxygen atom, nitrogen atom and/or sulfur atom(s) and so on. 5 to 7 membered mono-aromatic heterocyclic ring means, for example, pyrrole, imidazole, pyrazole, pyrroline, imidazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrooxazole, dihydroisoxazole, dihydrothiazole, dihydroisothiazole, dihydrofurazan, dihydrooxazine, dihydrooxazepine, tetrahydrooxazepine, dihydrooxadiazepine, tetrahydrooxadiazepine, dihydrothiazine, dihydrothiazepine, tetrahydrothiazepine, dihydrothiadiazepine, tetrahydrothiadiazepine and so on.

Mono-carbocyclic ring represented by ringA³ means, for example, C3-10 mono-aromatic carbocyclic ring which is partially or fully saturated and so on. C3-10 mono-aromatic carbocyclic ring which is partially or fully saturated means, for example, cyclopropene, cyclobutene, cyclopentene, cyclohexene, cycloheptene, cyclooctene, cyclopentadiene, cyclohexadiene, cycloheptadiene, cyclooctadiene, benzene and so on.

As ring represented by ringA³, C5-7 mono-carbocyclic ring is preferred. Concretely, it includes C5-7 mono-aromatic carbocyclic ring which is partially or fully saturated and so on. C5-7 mono-aromatic carbocyclic ring which is partially or fully saturated means, for example, cyclopentene, cyclohexene, cycloheptene, cyclopentadiene, cyclohexadiene, cycloheptadiene, benzene and so on.

In the specification, substituent represented by $R^1$, $R^2$, $R^3$, $R^4$, $R^5$, $R^6$ or $R^7$ has the same meanings as substituent in "cyclic ring which may have a substituent(s)" represented by the above-mentioned A.

In the specification, substituent in "carbon atom which may have a substituent(s)" represented by $J^1$ has the same meanings as substituent in "cyclic ring which may have a substituent(s)" represented by the above-mentioned A. The substituent(s) may be replaceable 1 to 2.

In the specification, substituent in "nitrogen atom which may have a substituent(s)" represented by $J^1$ has the same meanings as substituent in "cyclic ring which may have a substituent(s)" represented by the above-mentioned A.

In the specification, sulfur atom which may be oxidized means, for example, —S—, —SO— and —SO₂— and so on.

In the specification, "cyclic group which may have a substituent(s)" represented by ringA⁴ has the same meanings as "cyclic group which may have a substituent(s)" represented by the above-mentioned A.

In the specification, "cyclic group which may have a substituent(s)" represented by two R's taken together, and "cyclic group which may have a substituent(s)" represented by $R^4$ and $R^5$ and/or $R^6$ and $R^7$ taken together with their binding carbon atom means, for example, C3-10 mono-aromatic carbocyclic ring which is partially or fully saturated, 3 to 10 membered mono-aromatic heterocyclic ring which may be partially or fully saturated containing 1 to 2 hetero atom(s) selected from oxygen atom, nitrogen atom and/or sulfur atom(s) and so on. C3-10 mono-aromatic carbocyclic ring which is partially or fully saturated means, for example, cyclopropane, cylcobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene and so on. 3 to 10 membered mono-aromatic heterocyclic ring which may be partially or fully saturated containing 1 to 4 hetero atom(s) selected from oxygen atom, nitrogen atom and/or sulfur atom(s) means, for example, aziridine, azetidine, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophen, tetrahydrothiophen, dihydrothiopyran, tetrahydrothiopyran, dihydrothiepine, tetrahydrothiepine, perhydrothiepine, dihydrooxazole, tetrahydrooxazole (oxazolidine), dihydroisooxazole, tetrahydroisooxazole (isooxazolidine), dihydrothiazole, tetrahydrothiazole (thiazolidine), dihydroisothiazole, tetrahydroisothiazole (isothiazolidine), dihydrooxazine, tetrahydrooxazine, dihydrooxazepine, tetrahydrooxazepine, perhydrooxazepine, dihydrothiazine, tetrahydrothiazine, dihydrothiazepine, tetrahydrothiazepine, perhydrothiazepine, morpholine, thiomorpholine, oxathiane, dioxolane, dioxane, dithiolane, dithiane and so on.

As A, heterocyclic ring which may have a substituent(s) is preferred. 4 to 20 membered mono-, di-, tri- or tetra-aromatic heterocyclic ring optionally with substituent which may be partially or fully saturated containing 1 to 5 hetero atom(s) selected from oxygen atom, nitrogen atom and/or sulfur atom(s) is more preferred. 11 to 18 membered tri- or tetra-aromatic heterocyclic ring optionally with substituent which may be partially or fully saturated containing 1 to 5 hetero atom(s) selected from oxygen atom, nitrogen atom and/or sulfur atom(s) is further preferred.

As ringA¹, 11 to 18 membered tri- or tetra-aromatic heterocyclic ring optionally with a substituent(s) which may be partially or fully saturated containing at least one nitrogen atom, additionally which may contain 1 to 3 hetero atom(s) selected from oxygen atom, nitrogen atom and/or sulfur atom(s) is preferred. 13 to 16 membered tri- or tetra-aromatic heterocyclic ring optionally with a substituent(s) which may be partially or fully saturated containing at least one nitrogen atom, additionally which contains 1 to 3 hetero atom(s) selected from oxygen atom, nitrogen atom and/or sulfur atom(s) is more preferred. 2,3,4,9-tetrahydro-1H-β-carboline, 1,2,3,4,5,10-hexahydroazepino[3,4-b]indole, 1,2,3,4,5,6-hexahydroazepino[4,3-b]indole, 6,7,8,9-tetrahydro-5H-pyrido[4',3':4,5]pyrrolo[2,3-b]pyridine, 2,3,4,9-tetrahydro-1H-pyrido[4',3':4,5]pyrrolo[2,3-c]pyridine, 6,7,8,9-tetrahydro-5H-pyrido[3',4':4,5]pyrrolo[2,3-c]pyridine, 6,7,8,9-tetrahydro-5H-pyrido[4',3':4,5]pyrrolo[3,2-b]pyridine, 6,7,8,9-tetrahydro-5H-pyrido[4',3':4,5]pyrrolo[2,3-d]pyrimidine, 1,2,3,9-tetrahydrospiro[β-carboline-4,1'-cyclopropane], 1,2,4,9-tetrahydrospiro[β-carboline-3,1'-cyclopropane], 1,2,3,9-tetrahydrospiro[β-carboline-4,1'-cyclobutane], 1,2,4,9-tetrahydrospiro[β-carboline-3,1'-cyclobutane], 1,2,3,9-tetrahydrospiro[β-carboline-4,1'-cyclopentane], 1,2,4,9-tetrahydrospiro[β-carboline-3,1'-cyclopentane] which may have a substituent(s) is particularly preferred.

As ringA², 1,2,3,6-tetrahydropyridine, 2,3,4,7-tetrahydro-1H-azepine, 1,2,3,4-tetrahydropyrimidine, 3,4-dihydro-2H-1,3-oxazine, 3,4-dihydro-2H-1,3-thiazine, etc. is preferred.

As ringA³, benzene, pyridine, pyrimidine, pyrazine, etc. is preferred.

As X, single bond, C1-3 alkylene which may have a substituent(s), C2-3 alkenylene which may have a substituent(s), C2-3 alkynylene which may have a substituent(s) is preferred. Single bond, C1-3 alkylene which may have a substituent(s) is more preferred.

As Y, —C(=O)—, —C(=S)—, —C(=O)NR¹⁰³—, —C(=S)NR¹⁰³—, —SO₂—, —C(=O)O— or —SO₂NR¹⁰³— is preferred. —C(=O)—, —C(=O)NR¹⁰³—, SO₂—, —C(=O)O—, —SO₂NR¹⁰³— is more preferred. —C(=O)—, —C(=O)NR¹⁰³— is particularly preferred.

As Z, single bond, C1-3 alkylene which may have a substituent(s), C2-3 alkenylene which may have a substituent(s), C2-3 alkynylene which may have a substituent(s) is preferred. Single bond, C1-3 alkylene which may have a substituent is more preferred.

As "hydrocarbon group which may have a substituent(s)" represented by B, C1-8 alkyl, C2-8 alkenyl, C2-8 alkynyl which may be substituted with 1 to 4 substituent(s) optionally selected from hydroxyl, mercapto, amino, carboxyl, nitro, cyano, mono- or di-C1-6 alkylamino, C1-6 alkoxy, C1-6 alkylcarbonyloxy, C1-6 alkylthio, halogen atom, acyl, carbocyclic ring which may have a substituent(s), and heterocyclic ring which may have a substituent(s) is preferred.

As "cyclic group which may have a substituent(s)" represented by B and ringA⁴, C3-10 mono- or di-carbocyclic ring which is partially or fully saturated (e.g., benzene, naphthalene, etc.), or 3 to 10 membered mono- or di-aromatic heterocyclic ring which may be partially or fully saturated containing 1 to 4 hetero atom(s) selected from oxygen atom, nitrogen atom and/or sulfur atom(s) (e.g., pyridine, etc.) which may be substituted with 1 to 4 substituent(s) optionally selected from C1-8 alkyl, C2-8 alkenyl, C2-8 alkynyl, carbocyclic ring, heterocyclic ring, hydroxyl, C1-8 alkoxy (e.g., methoxy, ethoxy, n-propoxy, isopropoxy, n-butoxy, isobutoxy, sec-butoxy, tert-butoxy, pentyloxy, hexyloxy, heptyloxy, octyloxy, etc.), amino, NR¹⁰⁴R¹⁰⁵ (wherein R¹⁰⁴ and R¹⁰⁵ are each independently hydrogen atom or C1-8 alkyl.), carboxyl, C1-6 alkoxycarbonyl, nitro, cyano, halogen atom, oxo, acyl, formyl, and tri(C1-6 alkyl)silyl is preferred.

As "substituent in cyclic group which may have a substituent(s)" represented by A, and "di-, tri- or tetra-nitrogen-containing heterocyclic ring" represented by ringA¹, and substituent represented by R¹, 1 to 4 substituent(s) optionally selected from C1-8 alkyl, C2-8 alkenyl, C2-8 alkynyl, carbocyclic ring which may have a substituent(s), heterocyclic ring which may have a substituent(s), hydroxyl, C1-8 alkoxy (e.g., methoxy, ethoxy, n-propoxy, isopropoxy, n-butoxy, isobutoxy, sec-butoxy, tert-butoxy, pentyloxy, hexyloxy, heptyloxy, octyloxy, etc.), mercapto, C1-8 alkylthio (e.g., methylthio, ethylthio, n-propylthio, isopropylthio, n-butylthio, isobutylthio, sec-butylthio, tert-butylthio, pentylthio, hexylthio, heptylthio, octylthio, etc.), amino, NR¹⁰⁴R¹⁰⁵ (wherein R¹⁰⁴ and R¹⁰⁵ are each independently hydrogen atom or C1-8 alkyl.), carboxyl, C1-6 alkoxycarbonyl, nitro, cyano, halogen atom, oxo, acyl, formyl, and tri(C1-6 alkyl)silyl is(are) preferred.

As J¹, single bond, carbon atom which may have a substituent is preferred. Single bond is more preferred.

As "substituent" represented by R³, R⁴, R⁵, R⁶ and R⁷, C1-8 alkyl, C2-8 alkenyl, C2-8 alkynyl, carbocyclic ring, heterocyclic ring, hydroxyl, C1-8 alkoxy, mercapto, C1-8 alkylthio, amino, NR¹⁰⁴R¹⁰⁵ (wherein R¹⁰⁴ and R¹⁰⁵ are each independently hydrogen atom or C1-8 alkyl.), carboxyl, C1-6 alkoxycarbonyl, nitro, cyano, halogen atom, oxo, acyl, formyl, tri(C1-6 alkyl)silyl, etc. is preferred.

As "cyclic group which may have a substituent(s)" represented by R⁴ and R⁵ and/or R⁶ and R⁷ taken together with their binding carbon atom, C3-8 cycloalkyl (e.g., cyclopropyl, cyclobutyl, cyclopentyl, cyclohexyl, cycloheptyl, cyclooctyl, etc.) which may be substituted with 1 to 4 substituent(s) optionally selected from C1-8 alkyl, C2-8 alkenyl, C2-8 alkynyl, carbocyclic ring, heterocyclic ring, hydroxyl, C1-8 alkoxy, mercapto, C1-8 alkylthio, amino, NR¹⁰⁴R¹⁰⁵ (wherein R¹⁰⁴ and R¹⁰⁵ are each independently hydrogen atom or C1-8 alkyl.), carboxyl, C1-6 alkoxycarbonyl, nitro, cyano, halogen atom, oxo, acyl, formyl, tri(C1-6 alkyl)silyl, etc. is preferred.

In the compound represented by formula (I-2), as

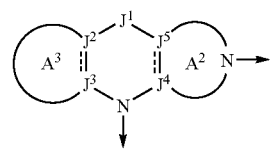

(wherein downward arrow means binding to R², rightward arrow means binding to X, the other symbols have the same meanings as that of the above-mentioned.),

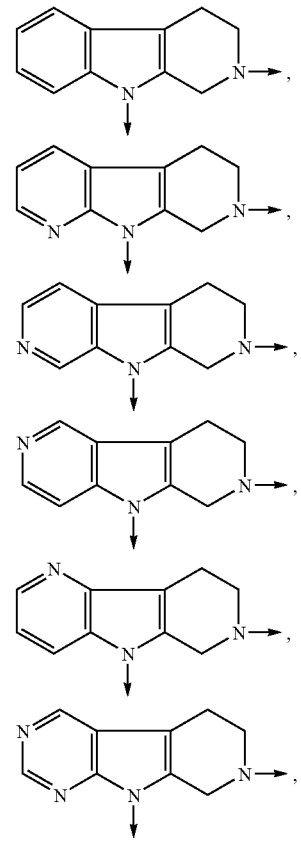

-continued
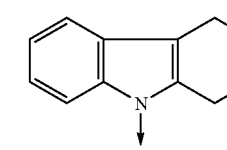

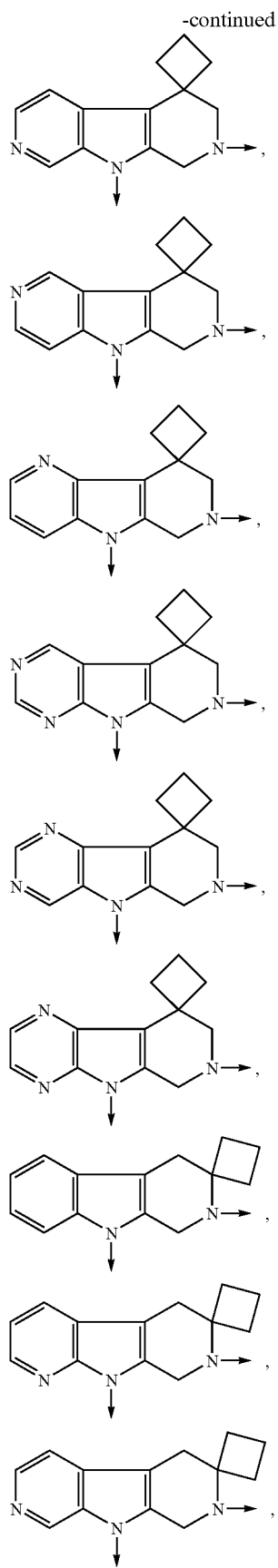
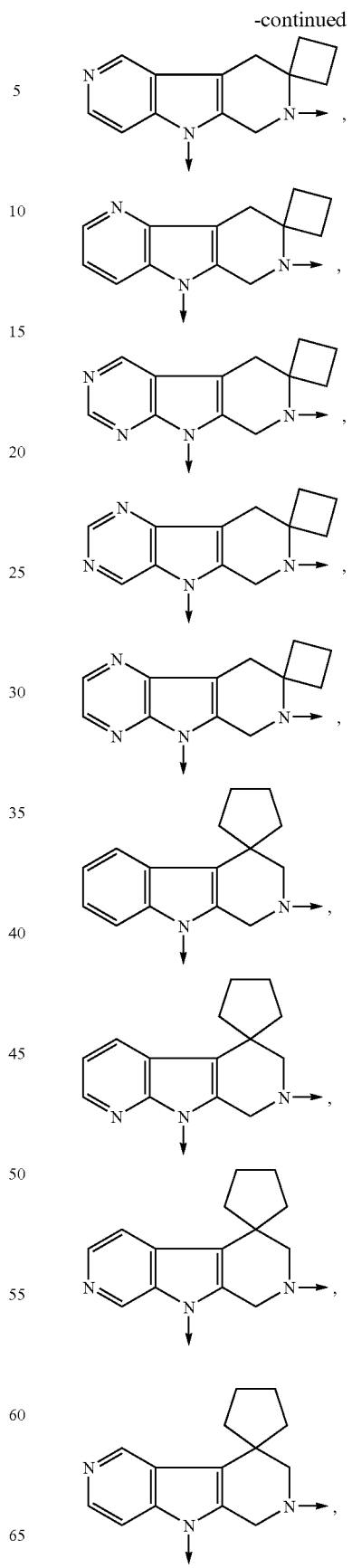

-continued
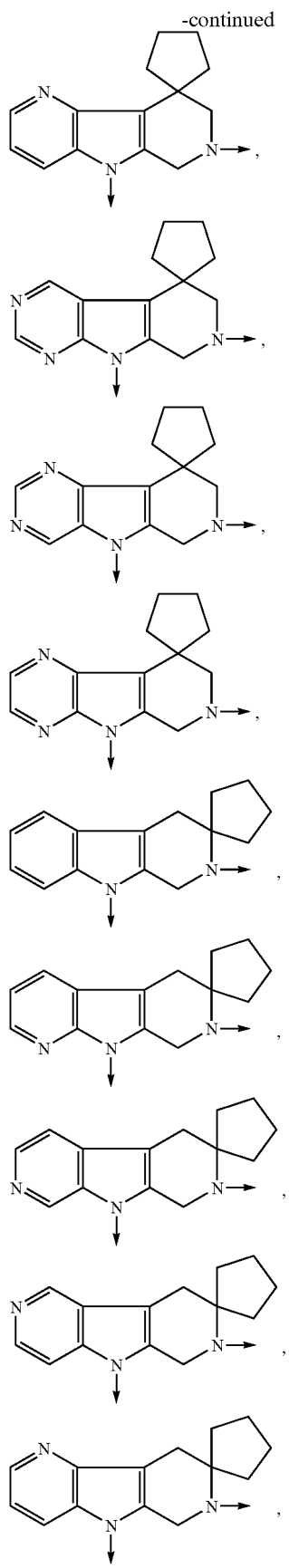
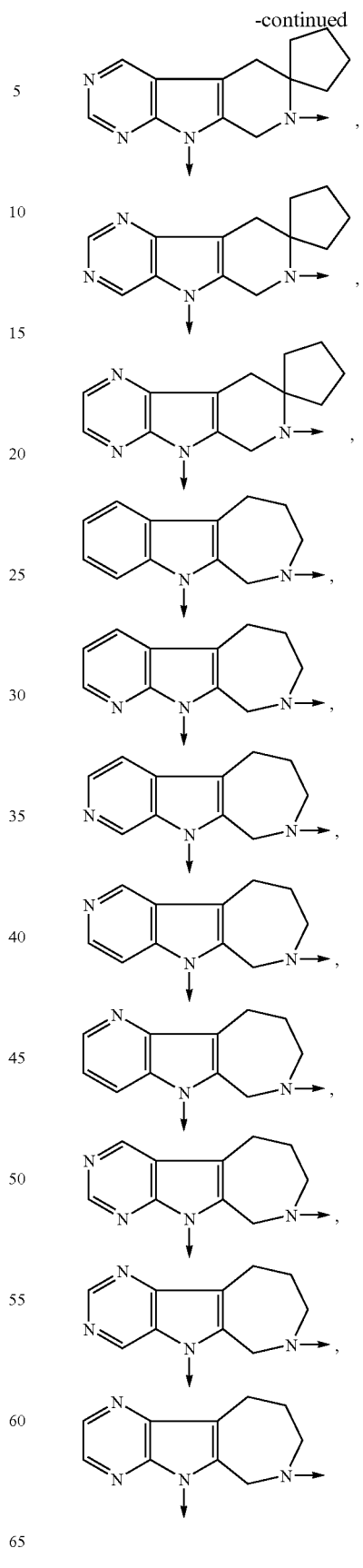
etc. is preferred.

As the compound represented by formula (I-3), the compound represented by formula (I-3-1)

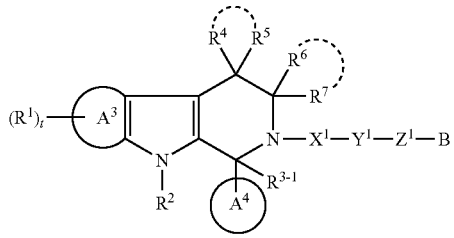

(I-3-1)

(wherein $R^{3-1}$ is a substituent, the other symbols have the same meanings as that of the above-mentioned.), the compound represented by formula (I-3-2)

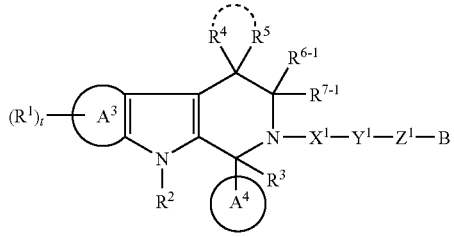

(I-3-2)

(wherein $R^{6-1}$ and $R^{7-1}$ are each independently a substituent, the other symbols have the same meanings as that of the above-mentioned.), the compound represented by formula (I-3-3)

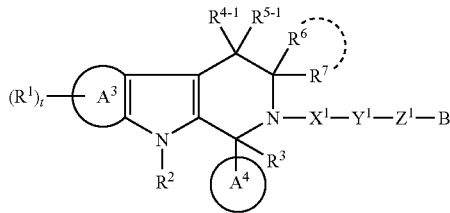

(I-3-3)

(wherein $R^{4-1}$ and $R^{5-1}$ are each independently a substituent, the other symbols have the same meanings as that of the above-mentioned.), the compound represented by formula (I-3-4)

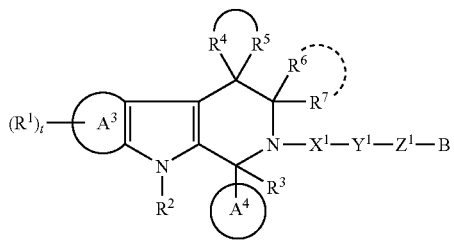

(I-3-4)

(wherein $R^4$ and $R^5$ are together with their carbon atom to be cyclic group which may have a substituent(s), the other symbols have the same meanings as that of the above-mentioned.), the compound represented by formula (I-3-5)

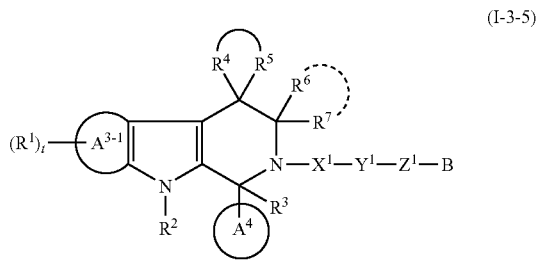

(I-3-5)

(wherein ring $A^{3-1}$ is 5 to 7 membered mono-heterocyclic ring, the other symbols have the same meanings as that of the above-mentioned.), etc. is preferred.

Furthermore, as concrete embodiments of the compound represented by formula (1), they includes the compounds described below or the compounds described in Example:

(1) 7-acetyl-6-(3-fluorophenyl)-6,7,8,9-tetrahydro-5H-pyrido[4',3':4,5]pyrrolo[3,2-b]pyridine, (2) 7-acetyl-6-(3-fluorophenyl)-6,7,8,9-tetrahydro-5H-pyrido[3',4':4,5]pyrrolo[2,3-c]pyridine, (3) 2-acetyl-1-(3-fluorophenyl)-2,3,4,9-tetrahydro-1H-pyrido[4',3':4,5]pyrrolo[2,3-c]pyridine, (4) 7-acetyl-6-(3-fluorophenyl)-6,7,8,9-tetrahydro-5H-pyrido[4',3':4,5]pyrrolo[3,2-d]pyrimidine, (5) 7-acetyl-6-(3-fluorophenyl)-6,7,8,9-tetrahydro-5H-pyrido[4',3':4,5]pyrrolo[2,3-b]pyrazine, (6) 7-acetyl-8-(3-fluorophenyl)-6,7,8,9-tetrahydro-5H-pyrido[4',3':4,5]pyrrolo[2,3-d]pyrimidine, (7) 7'-acetyl-6'-(3-fluorophenyl)-5',6',7',8'-tetrahydrospiro[cyclopropane-1,9'-pyrido[4',3':4,5]pyrrolo[3,2-b]pyridine], (8) 7'-acetyl-6'-(3-fluorophenyl)-5',6',7',8'-tetrahydrospiro[cyclopropane-1,9'-pyrido[3',4':4,5]pyrrolo[2,3-c]pyridine], (9) 2'-acetyl-1'-(3-fluorophenyl)-1',2',3',9'-tetrahydrospiro[cyclopropane-1,4'-pyrido[4',3':4,5]pyrrolo[2,3-c]pyridine],

(10) 7'-acetyl-8'-(3-fluorophenyl)-6',7',8',9'-tetrahydrospiro[cyclopropane-1,5'-pyrido[4',3':4,5]pyrrolo[2,3-b]pyridine],

(11) 7'-acetyl-6'-(3-fluorophenyl)-5',6',7',8'-tetrahydrospiro[cyclopropane-1,9'-pyrido[4',3':4,5]pyrrolo[3,2-d]pyrimidine],

(12) 7'-acetyl-6'-(3-fluorophenyl)-5',6',7',8'-tetrahydrospiro[cylcopropane-1,9'-pyrido[4',3':4,5]pyrrolo[2,3-b]pyrazine,

(13) 7'-acetyl-8'-(3-fluorophenyl)-6',7',8',9'-tetrahydrospiro[cyclopropane-1,5'-pyrido[4',3':4,5]pyrrolo[2,3-d]pyrimidine],

(14) 7'-acetyl-6'-(3-fluorophenyl)-5',6',7',9'-tetrahydrospiro[cyclopropane-1,8'-pyrido[4',3':4,5]pyrrolo[3,2-b]pyridine],

(15) 7'-acetyl-6'-(3-fluorophenyl)-5',6',7',9'-tetrahydrospiro[cyclopropane-1,8'-pyrido[3',4':4,5]pyrrolo[2,3-c]pyridine],

(16) 2'-acetyl-1'-(3-fluorophenyl)-1',2',4',9'-tetrahydrospiro[cylcopropane-1,3'-pyrido[4',3':4,5]pyrrolo[2,3-c]pyridine]

(17) 7'-acetyl-8'-(3-fluorophenyl)-5',7',8',9'-tetrahydrospiro[cyclopropane-1,6'-pyrido[4',3':4,5]pyrrolo[2,3-b]pyridine],

(18) 7'-acetyl-6'-(3-fluorophenyl)-5',6',7',9'-tetrahydrospiro[cyclopropane-1,8'-pyrido[4',3':4,5]pyrrolo[3,2-d]pyrimidine],

(19) 7'-acetyl-6'-(3-fluorophenyl)-5',6',7',9'-tetrahydrospiro[cyclopropane-1,8'-pyrido[4',3':4,5]pyrrolo[2,3-b]pyrazine],

(20) 7'-acetyl-8'-(3-fluorophenyl)-5',7',8',9'-tetrahydrospiro[cyclopropane-1,6'-pyrido[4',3':4,5]pyrrolo[2,3-d]pyrimidine],

(21) N-(3,5-dimethylphenyl)-6-(3-fluorophenyl)-5,6,8,9-tetrahydro-7H-pyrido[4',3':4,5]pyrrolo[3,2-b]pyridine-7-carboxamide,

(22) N-(3,5-dimethylphenyl)-6-(3-fluorophenyl)-5,6,8,9-tetrahydro-7H-pyrido[3',4':4,5]pyrrolo[2,3-c]pyridine-7-carboxamide,

(23) N-(3,5-dimethylphenyl)-1-(3-fluorophenyl)-1,3,4,9-tetrahydro-2H-pyrido[4',3':4,5]pyrrolo[2,3-c]pyridine-2-carboxamide,

(24) N-(3,5-dimethylphenyl)-6-(3-fluorophenyl)-5,6,8,9-tetrahydro-7H-pyrido[4',3':4,5]pyrrolo[3,2-d]pyrimidine-7-carboxamide,

(25) N-(3,5-dimethylphenyl)-6-(3-fluorophenyl)-5,6,8,9-tetrahydro-7H-pyrido[4',3':4,5]pyrrolo[2,3-b]pyrazine-7-carboxamide,

(26) N-(3,5-dimethylphenyl)-8-(3-fluorophenyl)-5,6,8,9-tetrahydro-7H-pyrido[4',3':4,5]pyrrolo[2,3-d]pyrimidine-7-carboxamide,

(27) N-(3,5-dimethylphenyl)-6'-(3-fluorophenyl)-5',6'-dihydrospiro[cyclopropane-1,9'-pyrido[4',3':4,5]pyrrolo[3,2-b]pyridine]-7'(8'H)-carboxamide,

(28) N-(3,5-dimethylphenyl)-6'-(3-fluorophenyl)-5',6'-dihydrospiro[cyclopropane-1,9'-pyrido[3',4':4,5]pyrrolo[2,3-c]pyridine]-7'(8'H)-carboxamide,

(29) N-(3,5-dimethylphenyl)-1'-(3-fluorophenyl)-1',9'-dihydrospiro[cyclopropane-1,4'-pyrido[4',3':4,5]pyrrolo[2,3-c]pyridine]-2'(3'H)-carboxamide,

(30) N-(3,5-dimethylphenyl)-8'-(3-fluorophenyl)-8',9'-dihydrospiro[cyclopropane-1,5'-pyrido[4',3':4,5]pyrrolo[2,3-b]pyridine]-7'(6'H)-carboxamide,

(31) N-(3,5-dimethylphenyl)-6'-(3-fluorophenyl)-5',6'-dihydrospiro[cyclopropane-1,9'-pyrido[4',3':4,5]pyrrolo[3,2-d]pyrimidine-7'(8'H)-carboxamide,

(32) N-(3,5-dimethylphenyl)-6'-(3-fluorophenyl)-5',6'-dihydrospiro[cyclopropane-1,9'-pyrido[4',3':4,5]pyrrolo[2,3-b]pyrazine]-7'(8'H)-carboxamide,

(33) N-(3,5-dimethylphenyl)-8'-(3-fluorophenyl)-8',9'-dihydrospiro[cylcopropane-1,5'-pyrido[4',3':4,5]pyrrolo[2,3-d]pyrimidine]-7'(6'H)-carboxamide,

(34) N-(3,5-dimethylphenyl)-6'-(3-fluorophenyl)-6',9'-dihydrospiro[cyclopropane-1,8'-pyrido[4',3':4,5]pyrrolo[3,2-b]pyridine]-7'(5'H)-carboxamide,

(35) N-(3,5-dimethylphenyl)-6'-(3-fluorophenyl)-6',9'-dihydrospiro[cyclopropane-1,8'-pyrido[3',4':4,5]pyrrolo[2,3-c]pyridine]-7'(5'H)-carboxamide,

(36) N-(3,5-dimethylphenyl)-1'-(3-fluorophenyl)-4',9'-dihydrospiro[cyclopropane-1,3'-pyrido[4',3':4,5]pyrrolo[2,3-c]pyridine]-2'(1'H)-carboxamide,

(37) N-(3,5-dimethylphenyl)-8'-(3-fluorophenyl)-8',9'-dihydrospiro[cyclopropane-1,6'-pyrido[4',3':4,5]pyrrolo[2,3-b]pyridine]-7'(5'H)-carboxamide,

(38) N-(3,5-dimethylphenyl)-6'-(3-fluorophenyl)-6',9'-dihydrospiro[cyclopropane-1,8'-pyrido[4',3':4,5]pyrrolo[3,2-d]pyrimidine]-7'(5'H)-carboxamide,

(39) N-(3,5-dimethylphenyl)-6'-(3-fluorophenyl)-6',9'-dihydrospiro[cyclopropane-1,8'-pyrido[4',3':4,5]pyrrolo[2,3-b]pyrazine]-7'(5'H)-carboxamide,

(40) N-(3,5-dimethylphenyl)-8'-(3-fluorophenyl)-8',9'-dihydrospiro[cyclopropane-1,6'-pyrido[4',3':4,5]pyrrolo[2,3-d]pyrimidine]-7'(5'H)-carboxamide,

(41) methyl 6-(3-fluorophenyl)-5,6,8,9-tetrahydro-7H-pyrido[4',3':4,5]pyrrolo[3,2-b]pyridine-7-carboxylate,

(42) methyl 6-(3-fluorophenyl)-5,6,8,9-tetrahydro-7H-pyrido[3',4':4,5]pyrrolo[2,3-c]pyridine-7-carboxylate,

(43) methyl 1-(3-fluorophenyl)-1,3,4,9-tetrahydro-2H-pyrido[4',3':4,5]pyrrolo[2,3-c]pyridine-2-carboxylate,

(44) methyl 8-(3-fluorophenyl)-5,6,8,9-tetrahydro-7H-pyrido[4',3':4,5]pyrrolo[2,3-b]pyridine-7-carboxylate,

(45) methyl 6-(3-fluorophenyl)-5,6,8,9-tetrahydro-7H-pyrido[4',3':4,5]pyrrolo[3,2-d]pyrimidine-7-caboxylate,

(46) methyl 6-(3-fluorophenyl)-5,6,8,9-tetrahydro-7H-pyrido[4',3':4,5]pyrrolo[2,3-b]pyrazine-7-carboxylate,

(47) methyl 8-(3-fluorophenyl)-5,6,8,9-tetrahydro-7H-pyrido[4',3':4,5]pyrrolo[2,3-d]pyrimidine-7-carboxylate,

(48) methyl 6'-(3-fluorophenyl)-5',6'-dihydrospiro[cyclopropane-1,9'-pyrido[4',3':4,5]pyrrolo[3,2-b]pyridine]-7'(8'H)-carboxylate,

(49) methyl 6'-(3-fluorophenyl)-5',6'-dihydrospiro[cyclopropane-1,9'-pyrido[3',4':4,5]pyrrolo[2,3-c]pyridine]-7'(8'H)-carboxylate,

(50) methyl 1'-(3-fluorophenyl)-1',9'-dihydrospiro[cyclopropane-1,4'-pyrido[4',3':4,5]pyrrolo[2,3-c]pyridine]-2'(3'H)-carboxylate,

(51) methyl 8'-(3-fluorophenyl)-8',9'-dihydrospiro[cyclopropane-1,5'-pyrido[4',3':4,5]pyrrolo[2,3-b]pyridine]-7'(6'H)-carboxylate,

(52) methyl 6'-(3-fluorophenyl)-5',6'-dihydrospiro[cyclopropane-1,9'-pyrido[4',3':4,5]pyrrolo[3,2-d]pyrimidine]-7'(8'H)-carboxylate,

(53) methyl 6'-(3-fluorophenyl)-5',6'-dihydrospiro[cyclopropane-1,9'-pyrido[4',3':4,5]pyrrolo[2,3-b]pyrazine]-7'(8'H)-carboxylate,

(54) methyl 8'-(3-fluorophenyl)-8',9'-dihydrospiro[cyclopropane-1,5'-pyrido[4',3':4,5]pyrrolo[2,3-d]pyrimidine]-7'(6'H)-carboxylate,

(55) methyl 6'-(3-fluorophenyl)-6',9'-dihydrospiro[cyclopropane-1,8'-pyrido[4',3':4,5]pyrrolo[3,2-b]pyridine]-7'(5'H)-carboxylate,

(56) methyl 6'-(3-fluorophenyl)-6',9'-dihydrospiro[cyclopropane-1,8'-pyrido[3',4':4,5]pyrrolo[2,3-c]pyridine]-7'(5'H)-carboxylate,

(57) methyl 1'-(3-fluorophenyl)-4',9'-dihydrospiro[cyclopropane-1,3'-pyrido[4',3':4,5]pyrrolo[2,3-c]pyridine]-2'(1'H)-carboxylate,

(58) methyl 8'-(3-fluorophenyl)-8',9'-dihydrospiro[cyclopropane-1,6'-pyrido[4',3':4,5]pyrrolo[2,3-b]pyridine]-7'(5'H)-carboxylate,

(59) methyl 6'-(3-fluorophenyl)-6',9'-dihydrospiro[cyclopropane-1,8'-pyrido[4',3':4,5]pyrrolo[3,2-d]pyrimidine]-7'(5'H)-carboxylate,

(60) methyl 6'-(3-fluorophenyl)-6',9'-dihydrospiro[cyclopropane-1,8'-pyrido[4',3':4,5]pyrrolo[2,3-b]pyrazine]-7'(5'H)-carboxylate,

(61) methyl 8'-(3-fluorophenyl)-8',9'-dihydrospiro[cyclopropane-1,6'-pyrido[4',3':4,5]pyrrolo[2,3-d]pyrimidine]-7'(5'H)-carboxylate,

(62) 7-acetyl-8-(2-fluorophenyl)-6,7,8,9-tetrahydro-5H-pyrido[4',3':4,5]pyrrolo[2,3-b]pyridine,

(63) 7-acetyl-8-(4-fluorophenyl)-6,7,8,9-tetrahydro-5H-pyrido[4',3':4,5]pyrrolo[2,3-b]pyridine,

(64) 7-acetyl-8-(2,3-difluorophenyl)-6,7,8,9-tetrahydro-5H-pyrido[4',3':4,5]pyrrolo[2,3-b]pyridine,
(65) 7-acetyl-8-(2,4-difluorophenyl)-6,7,8,9-tetrahydro-5H-pyrido[4',3':4,5]pyrrolo[2,3-b]pyridine,
(66) 7-acetyl-8-(2,5-difluorophenyl)-6,7,8,9-tetrahydro-5H-pyrido[4',3':4,5]pyrrolo[2,3-b]pyridine,
(67) 7-acetyl-8-(2,6-difluorophenyl)-6,7,8,9-tetrahydro-5H-pyrido[4',3':4,5]pyrrolo[2,3-b]pyridine,
(68) 7-acetyl-8-(3,4-difluorophenyl)-6,7,8,9-tetrahydro-5H-pyrido[4',3':4,5]pyrrolo[2,3-b]pyridine,
(69) 7-acetyl-8-(3,5-difluorophenyl)-6,7,8,9-tetrahydro-5H-pyrido[4',3':4,5]pyrrolo[2,3-b]pyridine,
(70) 7-acetyl-8-(3-methoxyphenyl)-6,7,8,9-tetrahydro-5H-pyrido[4',3':4,5]pyrrolo[2,3-b]pyridine,
(71) 7-acetyl-8-(3-methoxyphenyl)-6,7,8,9-tetrahydro-5H-pyrido[4',3':4,5]pyrrolo[2,3-b]pyridine,
(72) 7-acetyl-8-(4-methoxyphenyl)-6,7,8,9-tetrahydro-5H-pyrido[4',3':4,5]pyrrolo[2,3-b]pyridine,
(73) 7-acetyl-8-(2,3-dimethoxyphenyl)-6,7,8,9-tetrahydro-5H-pyrido[4',3':4,5]pyrrolo[2,3-b]pyridine,
(74) 7-acetyl-8-(2,4-dimethoxyphenyl)-6,7,8,9-tetrahydro-5H-pyrido[4',3':4,5]pyrrolo[2,3-b]pyridine,
(75) 7-acetyl-8-(2,5-dimethoxyphenyl)-6,7,8,9-tetrahydro-5H-pyrido[4',3':4,5]pyrrolo[2,3-b]pyridine,
(76) 7-acetyl-8-(2,6-dimethoxyphenyl)-6,7,8,9-tetrahydro-5H-pyrido[4',3':4,5]pyrrolo[2,3-b]pyridine,
(77) 7-acetyl-8-(3,4-dimethoxyphenyl)-6,7,8,9-tetrahydro-5H-pyrido[4',3':4,5]pyrrolo[2,3-b]pyridine,
(78) 7-acetyl-8-(3,5-dimethoxyphenyl)-6,7,8,9-tetrahydro-5H-pyrido[4',3':4,5]pyrrolo[2,3-b]pyridine,
(79) N-(3,5-dimethylphenyl)-8-(2-fluorophenyl)-5,6,8,9-tetrahydro-7H-pyrido[4',3':4,5]pyrrolo[2,3-b]pyridine-7-carboxamide,
(80) N-(3,5-dimethylphenyl)-8-(4-fluorophenyl)-5,6,8,9-tetrahydro-7H-pyrido[4',3':4,5]pyrrolo[2,3-b]pyridine-7-carboxamide,
(81) 8-(2,3-difluorophenyl)-N-(3,5-dimethylphenyl)-5,6,8,9-tetrahydro-7H-pyrido[4',3':4,5]pyrrolo[2,3-b]pyridine-7-carboxamide,
(82) 8-(2,4-difluorophenyl)-N-(3,5-dimethylphenyl)-5,6,8,9-tetrahydro-7H-pyrido[4',3':4,5]pyrrolo[2,3-b]pyridine-7-carboxamide,
(83) 8-(2,5-difluorophenyl)-N-(3,5-dimethylphenyl)-5,6,8,9-tetrahydro-7H-pyrido[4',3':4,5]pyrrolo[2,3-b]pyridine-7-carboxamide,
(84) 8-(2,6-difluorophenyl)-N-(3,5-dimethylphenyl)-5,6,8,9-tetrahydro-7H-pyrido[4',3':4,5]pyrrolo[2,3-b]pyridine-7-carboxamide,
(85) 8-(3,4-difluorophenyl)-N-(3,5-dimethylphenyl)-5,6,8,9-tetrahydro-7H-pyrido[4',3':4,5]pyrrolo[2,3-b]pyridine-7-carboxamide,
(86) 8-(3,5-difluorophenyl)-N-(3,5-dimethylphenyl)-5,6,8,9-tetrahydro-7H-pyrido[4',3':4,5]pyrrolo[2,3-b]pyridine-7-carboxamide,
(87) N-(3,5-dimethylphenyl)-8-(2-methoxyphenyl)-5,6,8,9-tetrahydro-7H-pyrido[4',3':4,5]pyrrolo[2,3-b]pyridine-7-carboxamide,
(88) N-(3,5-dimethylphenyl)-8-(3-methoxyphenyl)-5,6,8,9-tetrahydro-7H-pyrido[4',3':3,5]pyrrolo[2,3-b]pyridine-7-carboxamide,
(89) N-(3,5-dimethylphenyl)-8-(4-methoxyphenyl)-5,6,8,9-tetrahydro-7H-pyrido[4',3':4,5]pyrrolo[2,3-b]pyridine-7-carboxamide,
(90) 8-(2,3-dimethoxyphenyl)-N-(3,5-dimethylphenyl)-5,6,8,9-tetrahydro-7H-pyrido[4',3':4,5]pyrrolo[2,3-b]pyridine-7-carboxamide,
(91) 8-(2,4-dimethoxyphenyl)-N-(3,5-dimethylphenyl)-5,6,8,9-tetrahydro-7H-pyrido[4',3':4,5]pyrrolo[2,3-b]pyridine-7-carboxamide,
(92) 8-(2,5-dimethoxyphenyl)-N-(3,5-dimethylphenyl)-5,6,8,9-tetrahydro-7H-pyrido[4',3':4,5]pyrrolo[2,3-b]pyridine-7-carboxamide,
(93) 8-(2,6-dimethoxyphenyl)-N-(3,5-dimethylphenyl)-5,6,8,9-tetrahydro-7H-pyrido[4',3':4,5]pyrrolo[2,3-b]pyridine-7-carboxamide,
(94) 8-(3,4-dimethoxyphenyl)-N-(3,5-dimethylphenyl)-5,6,8,9-tetrahydro-7H-pyrido[4',3':4,5]pyrrolo[2,3-b]pyridine-7-carboxamide,
(95) 8-(3,5-dimethoxyphenyl)-N-(3,5-dimethylphenyl)-5,6,8,9-tetrahydro-7H-pyrido[4',3':4,5]pyrrolo[2,3-b]pyridine-7-carboxamide,
(96) methyl 8-(2-fluorophenyl)-5,6,8,9-tetrahydro-7H-pyrido[4',3':4,5]pyrrolo[2,3-b]pyridine-7-carboxylate,
(97) methyl 8-(4-fluorophenyl)-5,6,8,9-tetrahydro-7H-pyrido[4',3':4,5]pyrrolo[2,3-b]pyridine-7-carboxylate,
(98) methyl 8-(2,3-difluorophenyl)-5,6,8,9-tetrahydro-7H-pyrido[4',3':4,5]pyrrolo[2,3-b]pyridine-7-carboxylate,
(99) methyl 8-(2,4-difluorophenyl)-5,6,8,9-tetrahydro-7H-pyrido[4',3':4,5]pyrrolo[2,3-b]pyridine-7-carboxylate,
(100) methyl 8-(2,5-difluorophenyl)-5,6,8,9-tetrahydro-7H-pyrido[4',3':4,5]pyrrolo[2,3-b]pyridine-7-carboxylate,
(101) methyl 8-(2,6-difluorophenyl)-5,6,8,9-tetrahydro-7H-pyrido[4',3':4,5]pyrrolo[2,3-b]pyridine-7-carboxylate,
(102) methyl 8-(3,4-difluorophenyl)-5,6,8,9-tetrahydro-7H-pyrido[4',3':4,5]pyrrolo[2,3-b]pyridine-7-carboxylate,
(103) methyl 8-(3,5-difluorophenyl)-5,6,8,9-tetrahydro-7H-pyrido[4',3':4,5]pyrrolo[2,3-b]pyridine-7-carboxylate,
(104) methyl 8-(2-methoxyphenyl)-5,6,8,9-tetrahydro-7H-pyrido[4',3':4,5]pyrrolo[2,3-b]pyridine-7-carboxylate,
(105) methyl 8-(3-methoxyphenyl)-5,6,8,9-tetrahydro-7H-pyrido[4',3':4,5]pyrrolo[2,3-b]pyridine-7-carboxylate,
(106) methyl 8-(4-methoxyphenyl)-5,6,8,9-tetrahydro-7H-pyrido[4',3':4,5]pyrrolo[2,3-b]pyridine-7-carboxylate,
(107) methyl 8-(2,3-dimethoxyphenyl)-5,6,8,9-tetrahydro-7H-pyrido[4',3':4,5]pyrrolo[2,3-b]pyridine-7-carboxylate,
(108) methyl 8-(2,4-dimethoxyphenyl)-5,6,8,9-tetrahydro-7H-pyrido[4',3':4,5]pyrrolo[2,3-b]pyridine-7-carboxylate,
(109) methyl 8-(2,5-dimethoxyphenyl)-5,6,8,9-tetrahydro-7H-pyrido[4',3':4,5]pyrrolo[2,3-b]pyridine-7-carboxylate,
(110) methyl 8-(2,6-dimethoxyphenyl)-5,6,8,9-tetrahydro-7H-pyrido[4',3':4,5]pyrrolo[2,3-b]pyridine-7-carboxylate,
(111) methyl 8-(3,4-dimethoxyphenyl)-5,6,8,9-tetrahydro-7H-pyrido[4',3':4,5]pyrrolo[2,3-b]pyridine-7-carboxylate,
(112) methyl 8-(3,5-dimethoxyphenyl)-5,6,8,9-tetrahydro-7H-pyrido[4',3':4,5]pyrrolo[2,3-b]pyridine-7-carboxylate,
(113) 2-acetyl-1-(2-fluorophenyl)-1,2,3,9-tetrahydrospiro[β-carboline-4,1'-cyclopropane],
(114) 2-acetyl-1-(4-fluorophenyl)-1,2,3,9-tetrahydrospiro[β-carboline-4,1'-cyclopropane],
(115) 2-acetyl-1-(2,3-difluorophenyl)-1,2,3,9-tetrahydrospiro[β-carboline-4,1'-cyclopropane],
(116) 2-acetyl-1-(2,4-difluorophenyl)-1,2,3,9-tetrahydrospiro[β-carboline-4,1'-cyclopropane],
(117) 2-acetyl-1-(2,5-difluorophenyl)-1,2,3,9-tetrahydrospiro[β-carboline-4,1'-cyclopropane],
(118) 2-acetyl-1-(2,6-difluorophenyl)-1,2,3,9-tetrahydrospiro[β-carboline-4,1'-cyclopropane], (119) 2-acetyl-1-(3,4-difluorophenyl)-1,2,3,9-tetrahydrospiro[β-carboline-4,1'-cyclopropane],
(120) 2-acetyl-1-(3,5-difluorophenyl)-1,2,3,9-tetrahydrospiro[β-carboline-4,1'-cyclopropane],
(121) 2-acetyl-1-(2-methoxyphenyl)-1,2,3,9-tetrahydrospiro[β-carboline-4,1'-cyclopropane],
(122) 2-acetyl-1-(3-methoxyphenyl)-1,2,3,9-tetrahydrospiro[β-carboline-4,1'-cyclopropane],
(123) 2-acetyl-1-(4-methoxyphenyl)-1,2,3,9-tetrahydrospiro[β-carboline-4,1'-cyclopropane],
(124) 2-acetyl-1-(2,3-dimethoxyphenyl)-1,2,3,9-tetrahydrospiro[β-carboline-4,1'-cyclopropane],
(125) 2-acetyl-1-(2,4-dimethoxyphenyl)-1,2,3,9-tetrahydrospiro[β-carboline-4,1'-cyclopropane],
(126) 2-acetyl-1-(2,5-dimethoxyphenyl)-1,2,3,9-tetrahydrospiro[β-carboline-4,1'-cyclopropane],
(127) 2-acetyl-1-(2,6-dimethoxyphenyl)-1,2,3,9-tetrahydrospiro[β-carboline-4,1'-cyclopropane],
(128) 2-acetyl-1-(3,4-dimethoxyphenyl)-1,2,3,9-tetrahydrospiro[β-carboline-4,1'-cyclopropane],
(129) 2-acetyl-1-(3,5-dimethoxyphenyl)-1,2,3,9-tetrahydrospiro[β-carboline-4,1'-cyclopropane],
(130) N-(3,5-dimethylphenyl)-1-(2-fluorophenyl)-1,9-dihydrospiro[β-carboline-4,1'-cyclopropane]-2(3H)-carboxamide,
(131) N-(3,5-dimethylphenyl)-1-(4-fluorophenyl)-1,9-dihydrospiro[β-carboline-4,1'-cyclopropane]-2(3H)-carboxamide,
(132) 1-(2,3-difluorophenyl)-N-(3,5-dimethylphenyl)-1,9-dihydrospiro[β-carboline-4,1'-cyclopropane]-2(3H)-carboxamide,
(133) 1-(2,4-difluorophenyl)-N-(3,5-dimethylphenyl)-1,9-dihydrospiro[β-carboline-4,1'-cyclopropane]-2(3H)-carboxamide,
(134) 1-(2,5-difluorophenyl)-N-(3,5-dimethylphenyl)-1,9-dihydrospiro[β-carboline-4,1'-cyclopropane]-2(3H)-carboxamide,
(135) 1-(2,6-difluorophenyl)-N-(3,5-dimethylphenyl)-1,9-dihydrospiro[β-carboline-4,1'-cyclopropane]-2(3H)-carboxamide,
(136) 1-(3,4-difluorophenyl)-N-(3,5-dimethylphenyl)-1,9-dihydrospiro[β-carboline-4,1'-cyclopropane]-2(3H)-carboxamide,
(137) 1-(3,5-difluorophenyl)-N-(3,5-dimethylphenyl)-1,9-dihydrospiro[β-carboline-4,1'-cyclopropane]-2(3H)-carboxamide,
(138) N-(3,5-dimethylphenyl)-1-(2-methoxyphenyl)-1,9-dihydrospiro[β-carboline-4,1'-cyclopropane]-2(3H)-carboxamide,
(139) N-(3,5-dimethylphenyl)-1-(3-methoxyphenyl)-1,9-dihydrospiro[β-carboline-4,1'-cyclopropane]-2(3H)-carboxamide,
(140) N-(3,5-dimethylphenyl)-1-(4-methoxyphenyl)-1,9-dihydrospiro[β-carboline-4,1'-cyclopropane]-2(3H)-carboxamide,
(141) 1-(2,3-dimethoxyphenyl)-N-(3,5-dimethylphenyl)-1,9-dihydrospiro[β-carboline-4,1'-cyclopropane]-2(3H)-carboxamide,
(142) 1-(2,4-dimethoxyphenyl)-N-(3,5-dimethylphenyl)-1,9-dihydrospiro[β-carboline-4,1'-cyclopropane]-2(3H)-carboxamide,
(143) 1-(2,5-dimethoxyphenyl)-N-(3,5-dimethylphenyl)-1,9-dihydrospiro[β-carboline-4,1'-cyclopropane]-2(3H)-carboxamide,
(144) 1-(2,6-dimethoxyphenyl)-N-(3,5-dimethylphenyl)-1,9-dihydrospiro[β-carboline-4,1'-cyclopropane]-2(3H)-carboxamide,
(145) 1-(3,4-dimethoxyphenyl)-N-(3,5-dimethylphenyl)-1,9-dihydrospiro[β-carboline-4,1'-cyclopropane]-2(3H)-carboxamide,
(146) 1-(3,5-dimethoxyphenyl)-N-(3,5-dimethylphenyl)-1,9-dihydrospiro[β-carboline-4,1'-cyclopropane]-2(3H)-carboxamide,
(146) 1-(3,5-dimethoxyphenyl)-N-(3,5-dimethylphenyl)-1,9-dihydrospiro[β-carboline-4,1'-cyclopropane]-2(3H)-carboxylate,
(147) methyl 1-(2-fluorophenyl)-1,9-dihydrospiro[β-carboline-4,1'-cyclopropane]-2(3H)-carboxylate,
(148) methyl 1-(3-fluorophenyl)-1,9-dihydrospiro[β-carboline-4,1'-cyclopropane]-2(3H)-carboxylate,
(149) methyl 1-(4-fluorophenyl)-1,9-dihydrospiro[β-carboline-4,1'-cyclopropane]-2(3H)-carboxylate,
(150) methyl 1-(2,3-difluorophenyl)-1,9-dihydrospiro[β-carboline-4,1'-cyclopropane]-2(3H)-carboxylate,
(151) methyl 1-(2,4-difluorophenyl)-1,9-dihydrospiro[β-carboline-4,1'-cyclopropane]-2(3H)-carboxylate,
(152) methyl 1-(2,5-difluorophenyl)-1,9-dihydrospiro[β-carboline-4,1'-cyclopropane]-2(3H)-carboxylate,
(153) methyl 1-(2,6-difluorophenyl)-1,9-dihydrospiro[β-carboline-4,1'-cyclopropane]-2(3H)-carboxyalte,
(154) methyl 1-(3,4-difluorophenyl)-1,9-dihydrospiro[β-carboline-4,1'-cyclopropane]-2(3H)-carboxylate,
(155) methyl 1-(3,5-difluorophenyl)-1,9-dihydrospiro[β-carboline-4,1'-cyclopropane]-2(3H)-carboxylate,
(156) methyl 1-(2-methoxyphenyl)-1,9-dihydrospiro[β-carboline-4,1'-cyclopropane]-2(3H)-carboxylate,
(157) methyl 1-(3-methoxyphenyl)-1,9-dihydrospiro[β-carboline-4,1'-cyclopropane]-2(3H)-carboxylate,
(158) methyl 1-(4-methoxyphenyl)-1,9-dihydrospiro[β-carboline-4,1'-cyclopropane]-2(3H)-carboxylate,
(159) methyl 1-(2,3-dimethoxyphenyl)-1,9-dihydrospiro[β-carboline-4,1'-cyclopropane]-2(3H)-carboxylate,
(160) methyl 1-(2,4-dimethoxyphenyl)-1,9-dihydrospiro[β-carboline-4,1'-cyclopropane]-2(3H)-carboxylate,
(161) methyl 1-(2,5-dimethoxyphenyl)-1,9-dihydrospiro[β-carboline-4,1'-cyclopropane]-2(3H)-carboxylate,
(162) methyl 1-(2,6-dimethoxyphenyl)-1,9-dihydrospiro[β-carboline-4,1'-cyclopropane]-2(3H)-carboxylate,
(163) methyl 1-(3,4-dimethoxyphenyl)-1,9-dihydrospiro[β-carboline-4,1'-cyclopropane]-2(3H)-carboxylate,
(164) methyl 1-(3,5-dimethoxyphenyl)-1,9-dihydrospiro[β-carboline-4,1'-cyclopropane]-2(3H)-carboxylate,
(165) 2-acetyl-1-[2-(trimethylsilyl)phenyl]-2,3,4,9-tetrahydro-1H-β-carboline,
(166) 2-acetyl-1-[4-(trimethylsilyl)phenyl]-2,3,4,9-tetrahydro-1H-β-carboline,
(167) N-(3,5-dimethylphenyl)-1-[2-(trimethylsilyl)phenyl]-1,3,4,9-tetrahydro-2H-β-carboline-2-carboxamide,
(168) N-(3,5-dimethylphenyl)-1-[4-(trimethylsilyl)phenyl]-1,3,4,9-tetrahydro-2H-β-carboline-2-carboxamide,
(169) methyl 1-[2-(trimethylsilyl)phenyl]-1,3,4,9-tetrahydro-2H-β-carboline-2-carboxylate, and
(170) methyl 1-[4-(trimethylsilyl)phenyl]-1,3,4,9-tetrahydro-2H-β-carboline-2-carboxylate.

Unless otherwise specified, all isomers are included in the present invention. For example, alkyl, alkenyl, alkynyl, alkoxy, alkylthio, alkylene, alkenylene, alkynylene, alkylidene and alkenylidene group means straight-chain or branched-chain ones. In addition, isomers on double bond, ring, fused ring (E-, Z-, cis-, trans-isomer), isomers generated from asymmetric carbon atom(s) (R-, S-isomer, α-, β-configuration, enantiomer, diastereomer), optically active isomers (D-, L-, d-, l-isomer), polar compounds generated by chromatographic separation (more polar compound, less polar compound), equilibrium compounds, rotational isomers, mixtures thereof at voluntary ratios and racemic mixtures are also included in the present invention.

The salts of the compounds represented by formula (I) include all of pharmaceutically acceptable ones. As pharmaceutically salts, non-toxic, water-soluble salts are preferred. The suitable salts include for example, salts of alkali metals (e.g., potassium, sodium, lithium, etc.), salts of alkaline earth metals (e.g., calcium, magnesium, etc.), ammonium salts (e.g., tetramethylammonium salt, tetrabutylammonium salt, etc.), pharmaceutical acceptable salts of organic amine (e.g., triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid addition salts (salts of inorganic acids (e.g., hydrochloride, hydrobromide, hydroiodide, sulfate, phosphate, nitrate, etc.), and salts of organic acids (e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, etc.).

In addition, N-oxide means nitrogen atom of the compound represented by formula (I) is oxidized. The N-oxide of the compound in the present invention may be the above-mentioned salts of alkali (earth) metals, ammonium salts, salts of organic amine, acid addition salts and so on.

The suitable solvates include for example, hydrates, solvates of the alcohols (e.g., ethanol, etc.), and so on. The solvates are preferably nontoxic and water-soluble. In addition, the solvate of the compound in the present invention included the above-mentioned salts of alkali (earth) metals, ammonium salts, salts of organic amine, acid addition salts, N-oxide and so on.

The compound of the present invention may be converted into the above-mentioned N-oxide, the above-mentioned solvates by known methods.

The prodrug of the compounds represented by formula (I) means a compound is the compound represented by formula (I) by reaction with enzymes, gastric acids and so on within an organism. The prodrug of the compounds represented by formula (I) include, when the compounds represented by formula (I) have amino, the prodrug is the compounds the amino of which is acylated, alkylated, phosphorylated (e.g., the compounds are that the amino of the compounds represented by formula (I) is eicosanoated, alanylated, pentylaminocarbonylated, (5-methyl-2-oxo-1,3-dioxolan-4-yl)methoxycarbonylated, tetrahydrofuranated, pyrrolidylmethylated, pivaloyloxymethylated, acetoxymethylated, tert-butylated, etc.); when the compounds represented by formula (I) have hydroxyl, the prodrug is the compounds the hydroxyl of which are acylated, alkylated, phosphorylated, borated (e.g., the compounds are that the hydroxyl of the compounds represented by formula (I) are acetylated, palmitoylated, propanoylated, pivaloylated, succinylated, fumarylated, alanylated, dimethylaminomethylcarbonylated, etc.); when the compounds represented by formula (I) have carboxyl, the prodrug is the compound the carboxyl of which are esterified, amidated (e.g., the compounds are that the carboxyl of the compounds represented by formula (I) is ethylesterified, phenylesterified, carboxymethylesterified, dimethylaminomethylesterified, pivaloyloxymethylesterified, ethoxycarbonyloxyethylesterified, phthalidylesterified, (5-methyl-2-oxo-1,3-dioxolen-4-yl)methylesterified, cyclohexyloxycarbonylethylesterified, methylamidated, etc.); and so on. These compounds can be prepared by known methods. In addition, the prodrug of the compound represented by formula (I) may be either hydrate or non-hydrate. In addition, the prodrug of the compound represented by formula (I) may be converted into the compound represented by formula (I) under the physiological condition which is described in *The Development of Medicine*, vol. 7, "Molecular Design" published in 1991 Hirokawa Shoten p.p. 163-198. Further, the compound represented by formula (I) may be labeled with isotopes (e.g., $^3H$, $^{14}C$, $^{35}S$, $^{125}I$, etc.) and so on.

Pharmacological Activity

As pharmacological test except one described in Example, for example, there are the methods as follows.

Determination of Pregnenolone in Rat Adrenocortical Mitochondria:

The steroid productivity of the compound in the present invention can be evaluated using rat adrenocortical mitochondria.

After intraperitoneal administration of 20 mg/mL cycloheximide solution (1 mL) to male SD rats, 101 U/mL adrenocorticotropic hormone (ACTH) solution (0.3 mL) is intraperitoneally administered to them in five minutes. 20 minutes after ACTH administration, the rats are sacrificed by cervical dislocation and bilateral adrenal cortexes are removed at once. The removed adrenal cortexes are homogenized in buffer A (composition: 50 mmol/L Tris-HCl; 250 mmol/L sucrose) and then the suspension is centrifuged at 2000 g for 3 minutes at 4° C. The obtained supernatant is centrifuged at 12500 g for 10 minutes at 4° C. The pellet is washed with buffer A twice and suspended in buffer B (composition: 250 mmol/L sucrose; 10 mmol/L potassium phosphate buffer; 15 mmol/L triethanolamine; 20 mmol/L potassium chloride; 5 mmol/L magnesium chloride; 10 μmol/L trilostane; 10 mol/L SU10603) for experiments. Assay buffer which includes malic acid (150 mmol/L), β-NADP$^+$ (5 mmol/L) and the compound in the present invention is incubated for 5 minutes at 37° C. Then, crude mitochondrial membrane fraction derived from rat adrenal cortex is added and further incubated for 10 minutes at 37° C. to produce pregnenolone (final concentration of the compound: 1 μmol/L). After incubation, the reaction is terminated by addition of ethanol, extracted by addition of n-hexane and then evaporated to dryness. The residue is dissolved in buffer C (composition: 0.1% gelatin; phosphate buffered salts solution), centrifuged and then the collected supernatant is determined as samples for measurement. [3H] pregnenolone (10000 cpm; 100 μL), anti-pregnenolone antibody (ICN Biomedicals Inc; 100 μL) and sample (100 μL) are mixed and incubated overnight at 4° C. After the reaction, the mixture is added by dextran/charcoal (200 μL), mixed well, kept on ice for 10 minutes and then centrifuged. The radioactivity of the supernatant is measured by liquid scintillation counter. The pregnenolone in the sample is calculated from the standard curve.

Effect of the Compound in the Present Invention on Increase in Pregnenolon Content in the Brain by Loading Stressor:

It can be confirmed that MBR antagonist can inhibit steroid production in the brain, as follows.

Male Wistar rats are loaded with psychological stressor (*Brain Res.*, 641, 21-28, 1994). Water is stored up to about 10 cm depth in a container of which the platform is set up at the center. Rats in the non-treated group are loaded without administration and stressor. In contrast, rats in the stressor loaded group are orally administered with the vehicle or the compounds and 30 minutes later the rats are put on the platform to be loaded with stressor. One hour later from starting to load, the rats are irradiated by microwave (output: about: about 6.5 kW, exposure time: 0.96 s) using microwave applicator (Muromachi Kikai Co., Ltd.) and then the bilateral hippocampuses are removed and weighed. The hippocampuses are added by internal standard substance ($D_4$-pregnenolone 20 ng), water (1 mL) and diethylether/n-hexane (9:1, 3 mL) and stirred. The mixture is crushed by ultrasonic waves, stirred again, centrifuged at 300 rpm for minutes and the organic layer is transferred to new tube with Pasteur pipet. The water phase is extracted with diethylether/n-hexane (9:1, 3 mL) again and the organic layer is mixed to the above-mentioned extract. After reduced pressure to dryness, the residue is dissolved with 150 μL water/acetonitrile (1:9) again and measured by liquid chromatography/mass spectrometry (LC-MS). The measurement condition is shown as follows.

LC (Liquid chromatography): Hewlett Packard series 1100,

Column: Inertsil ODS-3, 3 μm, 2,1$^\Phi$×100 mm,

Temperature: room temperature,

Mobile phase: 5 mmol/L $CH_3CO_2NH_4$/MeCN (10:90),

Flow rate: 0.2 mL/min,

Injection volume: 40 μL,

MS (Micro spectrometry): Quattoro II (Micromass),

Ionization mode: Atmosphere Pressure Chemical Ionization (APCI), positive; Corona: 3.4 kV, Sheath gas: N2 (50 L/hr), Source temperature: 180° C., Probe temperature: 550° C., Detection: Pregnenolone: m/z 317.2 (cone: 10V), $D_4$-pregnenolone: m/z 321.2 (cone: 10V).

Processes for the Preparation of the Compound in the Present Invention:

The compound in the present invention represented by formula (I) can be prepared by combining the known processes, for example, the following processes or the processes shown in Examples, which is the properly improved processes described in "*Comprehensive Organic Transformations: A Guide to Functional Group Preparations,* 2nd Edition", "Richard C. Larock, John Wiley & Sons Inc, 1999". Still, ingredients may be used as salts in the following each processes for the preparation. As these salts, the salts described as the pharmaceutically acceptable ones in the above-mentioned formula (I) can be used.

a) Among the compounds represented by formula (I), the compound, wherein A is heterocyclic ring containing at least one nitrogen atom, X is a single bond, Y is —C(=O)—, —C(=O)$NR^{103}$—, —$SO_2$—, —C(=O)O—, —$SO_2NR^{103}$—, that is, the compound represented by formula (IA)

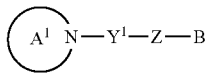

(IA)

(wherein $Y^1$ is —C(=O)—, —C(=O)$NR^{103}$—, —$SO_2$—, —C(=O)O— or —$SO_2NR^{103}$—, the other symbols have the same meanings as these described above.) can be prepared by following processes.

The compound represented by formula (IA) can be prepared by reacting the compound represented by formula (II)

(II)

(wherein ring$A^{1-1}$ has the same meanings as ring$A^1$, but carboxyl, hydroxyl, amino or mercapto included the group represented by ring$A^{1-1}$ are, if necessary, protected), with the compound represented by formula (III)

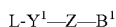

L-$Y^1$—Z—$B^1$ (III)

(wherein L is elimination group (e.g., halogen atom, imidazolyl, etc.), $B^1$ has the same meanings as B, but carboxyl, hydroxyl, amino or mercapto included the group represented by $B^1$ are, if necessary, protected. The other symbols has the same meanings as these described above.), if necessary, followed by subjecting to a deprotection reaction of protection group.

The reaction with the compound represented by formula (II) and the compound represented by formula (III) is carried out, for example, by reacting the compound represented by formula (II) with the compound represented by formula (III) in an organic solvent (e.g., chloroform, dichloromethane, diethylether, tetrahydrofuran, etc.) under the presence of a base (e.g., pyridine, triethylamine, dimethylaniline, dimethylaminopyridine, diisopropylethylamine, etc.) at a temperature from −20° C. to reflux temperature.

Or, it is carried out by reacting the compound represented by formula (II) with the compound represented by formula (III) in an organic solvent (e.g., dioxane, tetrahydrofuran, diethylether, etc.) using alkaline solution (e.g., sodium bicarbonate or sodium hydroxide solution, etc.) at the temperature from 0° C. to reflux temperature.

The deprotection reaction of a protective group for carboxyl, hydroxyl, amino, or mercapto is known, and it includes (1) alkaline hydrolysis, (2) deprotection reaction under acidic conditions, (3) deprotection reaction by hydrogenolysis, (4) deprotection reaction of a silyl group, (5) deprotection reaction using metals, (6) deprotection reaction using metal complexes, and so on.

These methods are described concretely as follows.

(1) The deprotection reaction by alkaline hydrolysis is, for example, carried out in an organic solvent (e.g., methanol, tetrahydrofuran, or dioxane, etc.) using a hydroxide of an alkali metal (e.g., sodium hydroxide, potassium hydroxide, or lithium hydroxide, etc.), a hydroxide alkaline earth metal (e.g., barium hydroxide, or calcium hydroxide, etc.), or a carbonate (e.g., sodium carbonate or potassium carbonate, etc.), or an aqueous solution thereof, or a mixture thereof at a temperature of 0 to 40° C.

(2) The deprotection reaction under acidic conditions is carried out, for example, in an organic solvent (e.g., dichloromethane, chloroform, dioxane, ethyl acetate, or anisole, etc.) in an organic acid (e.g., acetic acid, trifuloroacetic acid, methansulfonic acid, or p-tosylate, etc.), or an inorganic acid (e.g., hydrochloric acid, or sulfuric acid, etc.) or a mixture thereof (e.g., hydrogen bormide/acetic acid, etc.) at a temperature of 0 to 100° C.

(3) The deprotection reaction by hydrogenolysis is carried out, for example, in a solvent (e.g., ethers (e.g., tetrahydrofuran, dioxane, dimethoxyethane (DME), or diethylether, etc.), alcohols (e.g., methanol, or ethanol, etc.), benzenes (e.g., benzene, or toluene, etc.), ketones (e.g., acetone, or methylethylketone, etc.), nitriles (e.g., actetonitrile, etc.), amides (e.g., DMF, etc.), water, ethyl acetate, acetic acid, or a mixed solvent of at least two of these, etc.) in the presence of a catalyst (e.g., palladium-carbon, palladium black, palladium hydroxide-carbon, platinum oxide, or Raney nickel, etc.) under the hydrogen atmosphere at normal pressure or under pressurization, or in the presence of ammonium formate at a temperature of 0 to 200° C.

(4) The deprotection reaction of a silyl group is carried out, for example, in a water-miscible organic solvent (e.g., tetrahydrofuran, or acetonitrile, etc.) using tetrabutylammonium fluoride at a temperature of 0 to 40° C.

(5) The deprotection reaction using metals is carried out, for example, in an acidic solvent (e.g., acetic acid, pH4.2-7.2 buffer solution, or a mixture of a solution thereof and an organic solvent of tetrahydrofran, etc.) in the presence of zinc powder, if necessary sonicating, at the temperature of 0 to 40° C.

(6) The deprotection reaction using metal complexes is carried out, for example, in an organic solvent (e.g., dichloromethane, DMF, THF, ethyl acetate, acetonitrile, dioxane, ethanol, etc.), water, or a mixture thereof, in the presence of a trap reagent (e.g., tributyltine hydride, triethylsilane, dimedone, morpholine, diethylamine, pyrrolidine, etc.), an organic acid (e.g., acetic acid, formic acid, 2-ethylhexanoic acid, etc.) and/or salts of organic acid (e.g., sodium 2-ethylhexanoate, potassium 2-ethylhexanoate, etc.), in the presence or absence of a phosphine reagent (e.g., triphenylphosphine, etc.), using metal complexes (e.g., tetrakistriphenylphosphinepalladium(0), dichlorobis(triphenylphosphine)palladium(II), palladium acetate(II), tris(triphenylphosphine)rhodium(I) chloride, etc.) at the temperature of 0 to 40° C.

In addition, the deprotection reaction except the above-mentioned processes can be carried out, for example, by the process described in T. W. Greene, *Protective Groups in Organic Synthesis*, Wiley, New York, 1999.

The protection group for carboxyl includes, for example, methyl, ethyl, allyl, t-butyl, trichloroethyl, benzyl (Bn), phenacyl, p-methoxybenzyl, trityl, 2-chlorotrityl or structure thereof bound to solid phase carrier and so on.

The protection group for hydroxyl includes, for example, methyl, trytyl, methoxymethyl (MOM), 1-ethoxyethyl (EE) methoxyethoxymethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxycarbonyl (Alloc), 2,2,2-trichloroethoxycarbbnyl (Troc), and so on.

The protection group of amino includes benzyloxycarbonyl, t-butoxycarbonyl, allyloxycarbonyl (Alloc), 1-methyl-1-(4-biphenyl) ethoxycarbonyl (Bpoc), trifluoroacetyl, 9-fluorenylmethoxycarbonyl, benzyl (Bn), p-methoxybenzyl, benzyloxymethyl (BOM), 2-(trimethylsilyl) ethoxymethyl (SEM) and so on.

The protection group of mercapto includes, for example, benzyl (Bn), methoxybenzyl, methoxymethyl (MOM), 2-tetrahydropyranyl (THP), diphenylmethyl, acetyl (Ac) and so on.

The protective group for carboxyl, hydroxyl, amino or mercapto is not particularly limited to the above mentioned groups, so long as it can be easily and selectively left. For example, those described in T. W. Greene, *Protective Groups in Organic Synthesis*, Wiley, New York, 1999 can be used.

As will be easily understood by those skilled in the art, the intended compounds in the present invention can be easily prepared by choosing these deprotection reactions.

b) Among the compounds represented by formula (I), the compound, wherein A is heterocyclic ring containing at least one nitrogen atom, X is a single bond, Y is —C(=O)NR$^{103}$—, —C(=S)NR$^{103}$—, that is, the compound represented by formula (IB)

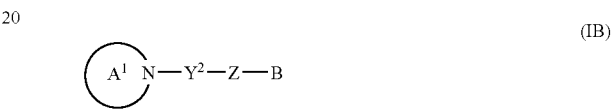

(wherein Y$^2$ is —C(=O)NR$^{103}$— or —C(=S)NR$^{103}$—, the other symbols have the same meanings as these described above.) can be prepared by following processes.

The compound represented by formula (IB) can be prepared by reacting the compound represented by formula (IV)

(wherein W is an oxygen or a sulfur atom, the other symbols have the same meaning as these described above.) with the compound represented by formula (V)

(wherein all the symbols have the same meanings as these described above.), if necessary, followed by subjecting to a deprotection reaction of protection group.

The reaction with the compound represented by formula (IV) and the compound represented by formula (V) is carried out, for example, by reacting the compound represented by formula (IV) with the compound represented by formula (V) in an organic solvent (e.g., chloroform, dichloromethane, diethylether, tetrahydrofuran, etc.) under the presence of a base (e.g., pyridine, triethylamine, dimethylaniline, dimethylaminopyridine, diisopropylethylamine, etc.) at a temperature from 0° C. to reflux temperature.

Or, it is carried out by reacting the compound represented by formula (IV) with the compound represented by formula (V) in an organic solvent (e.g., dioxane, tetrahydrofuran, diethylether, etc.) using alkali aqueous solution (e.g., sodium bicarbonate or sodium hydroxide solution, etc.) at the temperature from 0° C. to reflux temperature.

The deprotection reaction of the protective group can be carried out by the above-mentioned method.

The compound represented by formula (IB) can be prepared by reacting the compound represented by formula (II), the compound represented by formula (V) and the compound represented by formula (VI)

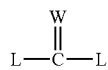  (VI)

(wherein all the symbols have the same meanings as these described above.), if necessary, followed by subjecting to a deprotection reaction of protection group.

The reaction with the compound represented by formula (II), the compound represented by formula (V) and the compound represented by formula (VI) is carried out, for example, by reacting the compound represented by formula (II), the compound represented by formula (V), the compound represented by formula (VI) (for example, phosgene compound (e.g., phosgene, thiophosgene, triphosgene(bis (trichloromethyl)carbonate), etc.), imidazole compound (e.g., CDI (carbonyldiimidazole), TCDI (thiocarbonylimidazole), etc.) in an organic solvent (e.g., ethyl acetate, chloroform, dichloromethane, diethylether, tetrahydrofuran, benzene, toluene, etc.) or absence of solvent and under the presence of a base (e.g., pyridine, triethylamine, dimethylaniline, dimethylaminopyridine, diisopropylethylamine, etc.) at a temperature from −20° C. to reflux temperature.

This reaction is preferably carried out under the anhydrous condition in the presence of inert gases.

The deprotection reaction of the protective group can be carried out by the above-mentioned method.

c) Among the compounds represented by formula (I), the compound, wherein A is heterocyclic ring containing at least one nitrogen atom, X is a single bond, Y is —C(=O)NH—, —C(=S)NH—, that is, the compound represented by formula (IC)

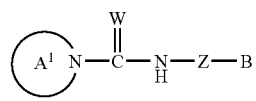  (IC)

(wherein all the symbols have the same meanings as these described above.) can be prepared by following processes.

The compound represented by formula (IC) can be prepared by reacting the compound represented by formula (II) with the compound represented by formula (VII)

$$W=C=N-Z-B^1 \quad (VII)$$

(wherein all the symbols have the same meanings as these described above.), if necessary, followed by subjecting to a deprotection reaction of protection group.

The reaction with the compound represented by formula (II) and the compound represented by formula (VII) is carried out, for example, by reacting the compound represented by formula (II) with the compound represented by formula (VII) in an organic solvent (e.g., toluene, benzene, xylene, tetrahydrofuran, dichloromethane, diethylether, 1,2-dichloroethane, dimethylformamide, etc.) at a temperature from 0° C. to reflux temperature.

This reaction is preferably carried out under the anhydrous condition in the presence of inert gases.

The deprotection reaction of the protective group can be carried out by the above-mentioned method.

d) Among the compounds represented by formula (I), the compound, wherein A is heterocyclic ring containing at least one nitrogen atom, X is C1-3 alkylene which may have a substituent(s), C2-3 alkenylene which may have a substituent(s), C2-3 alkynylene which may have a substituent(s), Y is —C(=O)—, —C(=O)NR$^{103}$—, —SO$_2$—, —C(=O)—, —SO$_2$NR$^{103}$—, that is, the compound represented by formula (ID)

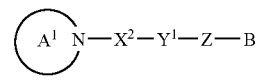  (ID)

(wherein X$^2$ is C1-3 alkylene which may have a substituent(s), C2-3 alkenylene which may have a substituent(s), or C2-3 alkynylene which may have a substituent(s), the other symbols have the same meanings as these described above.) can be prepared by following processes.

The compound represented by formula (ID) can be prepared by reacting the compound represented by formula (II) with the compound represented by formula (VIII)

$$L^1\text{-}X^2-Y-Z-B^1 \quad (VIII)$$

(wherein L$^1$ is halogen atom, the other symbols have the same meanings as these described above.), if necessary, followed by subjecting to a deprotection reaction of protection group.

The reaction with the compound represented by formula (II) and the compound represented by formula (VIII) is carried out, for example, in an organic solvent (e.g., tetrahydrofuran, dichloromethane, chloroform, benzene, toluene, xylene, hexane, heptane, cyclohexane, diethylether, dioxane, acetone, ethylmethylketone, acetonitrile, dimethylsulfoxide, dimethylformamide, dimethylacetamide, ethyl acetate, etc.), under the presence of a base (e.g., potassium carbonate, sodium carbonate, cesium carbonate, sodium hydride, etc.), and under the presence or the absence of a catalyst (e.g., potassium iodide, sodium iodide, tetra-n-butyl ammonium iodide, etc.) at a temperature from 0° C. to reflux temperature.

The deprotection reaction of the protective group can be carried out by the above-mentioned method.

e) Among the compounds represented by formula (I), the compound, wherein A is heterocyclic ring containing at least one nitrogen atom, X is a single bond, Y is —C(=O)— CR$^{101}$R$^{102}$—S—, —C(=S)R$^{101}$R$^{102}$—S—, that is, the compound represented by formula (IE)

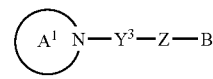  (IE)

(wherein Y$^3$ is —C(=O)—CR$^{101}$R$^{102}$—S—, —C(=S) R$^{101}$R$^{102}$—S—, the other symbols have the same meanings these described above.) can be prepared by following processes.

The compound represented by formula (IE) can be prepared by reacting the compound represented by formula (IX)

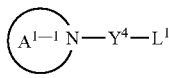

(wherein $Y^4$ is —C(=O)—$CR^{101}R^{102}$— or —C(=S)—$CR^{101}R^{102}$—, the other symbols have the same meanings these described above.)

with the compound represented by formula (X)

$$HS-B^1 \quad (X)$$

(wherein all the symbols have the same meanings as these described above.), if necessary, followed by subjecting to a deprotection reaction of protection group.

The reaction with the compound represented by formula (IX) and the compound represented by formula (X) is carried out, for example, in an organic solvent (e.g., tetrahydrofuran, dichloromethane, chloroform, benzene, toluene, xylene, hexane, heptane, cylcohexane, diethylether, dioxane, acetone, ethylmethylketone, acetonitrile, dimethylsulfoxide, dimethylformamide, dimethylacetamide, ethyl acetate, etc.), under the presence of a base (e.g., potassium carbonate, sodium carbonate, cesium carbonate, sodium hydride, etc.), and under the presence or the absence of a catalyst (e.g., potassium iodide, sodium iodide, tetra-n-butyl ammonium iodide etc) at a temperature from 0° C. to reflux temperature.

The deprotection reaction of the protective group can be carried out by the above-mentioned method.

f) Among the compounds represented by formula (I), the compound, wherein A is heterocyclic ring containing at least one nitrogen atom, X is a single bond, Y is —C(=O)— or —C(=S)—, Z is a single bond or C1-3 alkylene which may have a substituent(s), C2-3 alkenylene which may have a substituent(s), C2-3 alkynylene which may have a substituent(s), that is, the compound represented by formula (IF)

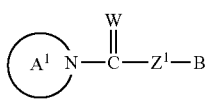

(wherein all the symbols have the same meanings as these described above.) can be prepared by following processes.

The compound represented by formula (IF) can be prepared by reacting the compound represented by formula (II) with the compound represented by formula (XI)

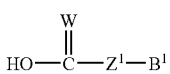

(wherein all the symbols have the same meanings as these described above.), if necessary, followed by subjecting to a deprotection reaction of protection group.

The reaction with the compound represented by formula (II) and the compound represented by formula (XI) is carried out, for example, by the method (1) using acid halide, (2) using mixed acid anhydride, (3) using condensing agent, etc.

These methods are explained concretely as follows.

(1) The method using acid halide is carried out, for example, by reacting the compound represented by formula (XI) in an organic solvent (e.g., chloroform, dichloroform, diethylether, tetrahydrofuran, dimethoxyethane, etc.) or the absence of solvent, with acid halide agent (e.g., oxalylchloride, thionylchloride, etc.) at the temperature from −20° C. to reflux temperature, and reacting the obtained acid halide with the compound represented by formula (II) in a organic solvent (e.g., chloroform, dichloromethane, diethylether, tetrahydrofuran, acetonitrile, ethyl acetate, etc.) under the presence of a base (e.g., pyridine, triethylamine, dimethylaniline, dimethylaminopyridine, diisopropylethylamine, etc.) at the temperature of from 0 to 40° C. In addition, it is carried out by reacting the obtained halide with the compound represented by formula (II) in an organic solvent (e.g., dioxane, tetrahydrofuran, dichloromethane, etc.), under the presence or absence of phase-transfer catalyst (e.g., quaternary ammonium salt, etc., for example, tetrabutylammoniumchloride, triethylbenzylammoniumchloride, tri-n-octylmethylammoniumchloride, trimethyldecylammoniumchloride, tetramethylammoniumbromide and so on.), using alkaline solution (e.g., sodium bicarbonate or sodium hydroxide solution, etc.) at the temperature from 0 to 40° C.

(2) The method using mixed acid anhydride is carried out, for example, the compound represented by formula (XI) with an acid halide (e.g., pivaloyl chloride, tosyl chloride, mesyl chloride, etc.), or an acid derivative (e.g., chloroethyl formate, chloroisobutyl formate, etc.) in an organic solvent (e.g., chloroform, dichloromethane, diethylether, tetrahydrofuran, etc.) or the absence of solvent, under the presence of a base (e.g., pyridine, triethylamine, dimethylaniline, dimethylaminopyridine, diisopropylethylamine, etc.) at the temperature from 0 to 40° C., and by reacting the obtained mixed acid anhydride with the compound represented by formula (II) in an organic solvent (e.g., chloroform, dichloromethane, diethylether, tetrahydrofuran, etc.) at the temperature from 0 to 40° C.

(3) The method using condensing agent is carried out, for example, by reacting the compound represented by formula (XI) with the compound represented by formula (II) in an organic solvent (e.g., chloroform, dichloromethane, dimethylformamide, diethylether, tetrahydrofuran, etc.), or in the absence of solvent, under the presence or the absence of a base (e.g., pyridine, triethylamine, dimethylaniline, dimethylaminopyridine, etc.) using the condensing agent (e.g., 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodine, 1-propanephosphonic acid cyclic anhydride (PPA), etc.), using or not using 1-hydroxybenztriazole (HOBt) at the temperature from 0 to 40° C.

These reactions (1), (2) and (3) are all preferably carried out under the anhydrous condition in the presence of inert gases (argon, nitrogen, etc.).

The deprotection reaction of the protective group can be carried out by the above-mentioned method.

The compounds represented by formula (II), (III), (IV), (V), (VI), (VII), (VIII), (IX), (X) and (XI) used as starting materials or reagents can be easily prepared by the known processes, the processes shown in following Examples, or the known processes, for example, processes described in "*Comprehensive Organic Transformations: A Guide to Functional Group Preparations,* 2nd Edition", "Richard C. Larock, John Wiley & Sons Inc, 1999".

In each reaction in the present specification, as will be understood by those skilled in the art, the reaction with heating can be effected using water bath, oil bath, sand bath or microwave.

In each reaction in the present specification, solid-phase supported reagent accordingly supported to macromolecule polymer (e.g., polystyrene, polyacrylamide, polypropylene, polyethyleneglycol, etc.) may be used.

In each reaction in the present specification, reaction products may be purified in an ordinary manner, for example, through normal-pressure or reduced-pressure distillation, or through high-performance liquid chromatography with silica gel or magnesium silicate, thin-layer chromatography, or column chromatography, ion-exchange resin, scavenger resin or through washing or recrystallizaion and so on. The purification may be effected in each reaction or after some reactions.

Toxicity:

Toxicity of the compound represented by formula (I) is very low, and it is safe enough to use as a pharmaceutical agent.

INDUSTRIAL APPLICABILITY

Since the compounds of the present invention represented by formula (I) have the affinity to MBR, they are useful for the prevention and/or treatment for disease induced or exacerbated and/or reignited by stressor or useful for the prevention and/or treatment for disease caused by stress.

The disease induced or exacerbated and/or reignited by stressor or the disease caused by stress include, for example, central nervous system diseases caused by stress (e.g., anxiety related disease (neurosis, psychosomatic disorder, generalized anxiety disorder (GAD), social-anxiety disorder (SAD), panic disorder, hyperactivity disorder, attention-deficit, personality disorder, bipolar disorder, autism, etc.), sleep disorder, depression, reactive depression, epilepsy, Parkinson's disease, Perkinsonian syndrome, schizophrenia, autonomic dystonia, Huntington's disease, Alzheimer's disease, affective disorder, cognitive disorder, migraine, tension headache, cluster headache, posttraumatic stress disorder, dissociative disorder, insomnia, nervous vomiting, nervous cough, psychogenic convulsive seizure, psychogenic syncopal attack, maladjustment to job, burn-out syndrome, chronic fatigue syndrome, writer's cramp, spastic torticollis, etc.), respiratory system diseases caused by stress (e.g., asthma, bronchial asthma, hyperventilation syndrome, laryngeal spasm, chronic obstructive pulmonary diseases, etc.), digestive system diseases caused by stress (e.g., irritable bowel syndrome, peptic ulcer, functional dyspepsia, gastric ulcer, duodenal ulcer, ulcerative colitis, biliary tract dyskinesia, esophageal spasm, gastric atony, aerophagy, chronic hepatitis, chronic panceatitis, etc.), cardiovascular system diseases caused by stress (e.g., essential hypertension, arrhythmia, (neurological) angina pectoris, essential hypotension, orthostatic dysregulation, myocardial infarction, arteriosclerosis, vertigo, etc.), uropathy-reproductive system diseases caused by stress (e.g., dysuria, nervous pollakisuria (hyperreflexic bladder), nocturia, enuresis, psychogenic ischuria, impotentia, prostatism, urethral syndrome, etc.), gynecologic disorder caused by stress (e.g., menopausal disorder, menstrual pain, premenstrual syndrome, infertility, frigidity, serious vomiting of pregnancy, abortion, immature birth, etc.), endocrine and metabolic disease caused by stress (e.g., anorexia nervosa, eating disorder, anorexia, hyperphagia, Bartter's syndrome, hyperthyroidism, diabetes, psychogenic polydipsia, adiposity, reflex hypoglycemia, etc.), ophthalmologic diseases caused by stress (e.g., asthenopia, central retinitis, floaters, blepharospasm, primary glaucoma, vertigo, etc.), otolaryngological diseases caused by stress (e.g., tinnitus, vertigo, psychogenic deafness, chronic sinusitis, allergic rhinitis, smell disorder, stuttering, aphonia, etc.), dental surgery and dentistry caused by stress (e.g., temporomandibular arthrosis, glossopharyngeal neuralgia, sudden glossodynia, stomatitis, toothache, ozostomia, abnormal salivation, bruxism, etc.), surgical and orthopedic diseases caused by stress (e.g., postoperative abdominal neurosis, dumping syndrome, polysurgery, plastic postoperative neurosis, rheumatoid arthritis, low back pain, cervico-omo-brachial syndrome, stiff neck, fibrositis, polyarthralgia, systemic myalgia, gout, etc.), skin diseases caused by stress (e.g., chronic urticaria, atopic dermatitis, hyperhidrosis, eczema, skin pruritus, alopecia greata, etc.) and other diseases caused by stress (e.g., cancer, systemic lupus erythematosus, etc.).

The compounds in the present invention may be administered in combination with other pharmaceutical preparations for the purpose of 1) complement and/or enhancement of preventing and/or treating effect of the compounds in the present invention, 2) improvement of dynamics/absorption and lowering of dose of the compounds in the present invention and/or 3) alleviation of side effect of the compounds in the present invention.

The compounds in the present invention and other pharmaceutical preparations may be administered in the form of formulation having these components incorporated in one preparation or may be administered in separate preparations. In the case where these pharmaceutical preparations are administered in separate preparations, they may be administered simultaneously or at different times. In the latter case, the compounds in the present invention may be administered before the other pharmaceutical preparations. Alternatively, the other pharmaceutical preparations may be administered before the compounds in the present invention. The method for the administration of these pharmaceutical preparations may be same or different.

The other pharmaceutical preparations may be low-molecular compounds. In addition, they may be macromolecular protein, polypeptide, polynucleotide (DNA, RNA, and gene), antisense, decoy, antibody or vaccine and so on. The dose of the other pharmaceutical preparations can be accordingly selected as a standard of clinical dose. Additionally, the compounding ratio of the compounds in the present invention and the other pharmaceutical preparations can be accordingly selected by the age and body weight of administering object, the administration method, the administration time, the object disease, the symptom, the combination, etc. For example, the other pharmaceutical preparations may be used from 0.01 to 100 parts by weight relative to 1 part by weight of the compounds in the present invention. The other pharmaceutical preparations may be administered at appropriate ratio combining one or more arbitrarily selected from the homogeneous groups or heterogeneous groups as follows. The other pharmaceutical preparations do not only include ones which have ever been found but ones which will be found from now based on the above-mentioned mechanism.

The other pharmaceutical preparations which may combine the compounds in the present invention include, for example, antianxiety drugs (e.g., benzodiazepine drugs, thienodiazepine drugs, non-benzodiazepine drugs, serotonergic drugs, CRF antagonists, tachykinin $NK_1$ antagonists, etc.), antidepressants (e.g., tricyclic antidepressants, tetracyclic antidepressants, monoamine release drugs, monoamine oxidase inhibitors, monoamine reuptake inhibitors (SSRI, SNRI), CRF inhibitors, tachykinin $NK_1$ inhibitors, neurotensin antagonists, etc.), antiparkinson drugs (e.g., anticholinergic drugs, dopamine agonists, monoamine oxidase inhibitors, etc.), schizophrenia drugs (e.g., dopamine antagonists, etc.), antiepileptic drugs (e.g., barbituric acid series, hydantoin series, etc.), anti vertigo drugs, asthmatic drugs (e.g., bronchodilators, α receptor agonists, $β_2$ receptor agonists, xanthine series, inhaled steroids, anticholinergic drugs, 5-lipoxygenase inhibitors, etc.), peptic ulcer drugs (e.g., offensive factor inhibitors, antipeptic drugs, antacids, histamine-$H_2$ receptor antagonists, anti gastrin drugs, proton pump inhibitors, muscarine receptor inhibitors, anticholinergic drugs, defensive factor enhancers, prostaglandin derivatives, etc.), gastrointestinal tract function regulators-gastrointestinal tract prokinetic drugs (e.g., intestinal remedies, CCK-A antagonists, neurotensin antagonists, opioid agonists, muscarine receptor inhibitors, 5-$HT_4$ agonists, 5-$HT_3$ antagonists, etc.), antidiarrheals (e.g., antidiarrheal drugs, opioid μ receptor stimulators, etc.), evacuants (e.g., bulk laxatives, saline laxatives, stimulant laxatives, affinity polyacrylic resin, etc.), antihypertensive drugs (e.g., calcium antagonists, β receptor blockers, $α_1$ receptor blockers, angiotensin converting enzyme inhibitors, angiotensin II receptor blockers, etc.), antiarrhythmic drugs (e.g., sodium inhibitors, β receptor blockers, potassium antagonists, calcium antagonists, etc.), cardiac stimulants (e.g., phosphodiesterase inhibitors, cardiac glycosides, β receptor agonists, etc.), dysuria remedies (e.g., frequent urination remedies, anticholinergic drugs, muscarine agonists (antagonists), tachykinin $NK_1$ antagonists, $NK_2$ antagonists, etc.) and so on.

The diseases on which the preventive and/or therapeutic effect works with the above-mentioned combination drugs are not especially limited. The diseases may be those which compensate for and/or enhance the preventive and/or therapeutic effect of the compounds in the present invention.

The other pharmaceutical preparations to compensate and/or enhance for preventive and/or therapeutic effect on irritable bowel syndrome of the compounds in the present invention include, for example, antianxiety drugs (e.g., benzodiazepine drugs, thienodiazepine drugs, non-benzodiazepine drugs, serotonergic drugs, CRF antagonists, etc.), antidepressants (e.g., monoamine release drugs, monoamine oxidase inhibitors, monoamine reuptake inhibitors (SSRI, SNRI), CRF inhibitors, neurotensin antagonists, tricyclic antidepressants, tetracyclic antidepressants, etc.), anticholinergic drugs, gastrointestinal tract function regulators gastrointestinal tract prokinetic drugs (e.g., intestinal remedies, CCK-A antagonists, neurotensin antagonists, opioid agonists, muscarine receptor inhibitors, 5-$HT_4$ agonists, etc.), antidiarrheals (e.g., antidiarrheal drugs, opioid μ receptor stimulators, etc.), evacuants (e.g., bulk laxatives, saline laxatives, stimulant laxatives, affinity polyacrylic resin, etc.), mucosal paralytic drugs, autonomic nerve modulators, calcium antagonists, phosphodiesterase inhibitors, serotonin antagonists (e.g., 5-$HT_3$ antagonists, 5-$HT_4$ antagonists, etc.), darifenacyn, polycarbophil calcium and so on.

The other pharmaceutical preparations to compensate and/or enhance for preventive and/or therapeutic effect on gastric ulcer and duodenal ulcer of the compounds in the present invention include, for example, peptic ulcer drugs (e.g., offensive factor inhibitors, antipeptic drugs, antacids, histamine-$H_2$ receptor antagonists, anti gastrin drugs, proton pump inhibitors, muscarine receptor inhibitors, anticholinergic drugs, defensive factor enhancers, prostaglandin derivatives, mesalazine, salazosulfapyridine, etc.), anticholinergic drugs, gastric mucosal paralytic drugs, antianxiety drugs (e.g., benzodiazepine drugs, thienodiazepine drugs, non-benzodiazepine drugs, serotonergic drugs, CRF antagonists, etc.), dopamine antagonists and so on.

The other pharmaceutical preparations to compensate and/or enhance for preventive and/or therapeutic effect on ulcerative colitis of the compounds in the present invention include, for example, mesalazine, salazosulfapyridine, peptic ulcer drugs (e.g., offensive factor inhibitors, antipeptic drugs, antacids, histamine-$H_2$ receptor antagonists, anti gastrin drugs, proton pump inhibitors, muscarine receptor inhibitors, anticholinergic drugs, defensive factor enhancers, prostaglandin derivatives, etc.), anticholinergic drugs, steroids, 5-lipoxygenase inhibitors, antioxidant drugs, $LTB_4$ antagonists, local anesthetics, immunosuppressive drugs, defensive factor enhancers, metalloprotease inhibitors and so on.

The other pharmaceutical preparations to compensate and/or enhance for preventive and/or therapeutic effect on biliary tract dyskinesia of the compounds in the present invention include, for example, ceruleins, antispasmodic drugs, COMT (catechol-O-methyltransferase) inhibitors, cholinergic agonists, antianxiety drugs, cholagogues, antidepressants, CCK-A antagonists and so on.

The other pharmaceutical preparations to compensate and/or enhance for preventive and/or therapeutic effect on aerophagy of the compounds in the present invention include, for example, intestinal remedies, antianxiety drugs, autonomic nerve modulators, fiber formulations, digestive enzymes, gas absorbent drugs, intestinal tract prokinetic drugs and so on.

The other pharmaceutical preparations to compensate and/or enhance for preventive and/or therapeutic effect on chronic hepatitis of the compounds in the present invention include, for example, liver hydrolysate formulations, polyenephosphatidylcholine, glycyrrhizin formulations, protoporphyrin sodium, ursodeoxycholic acid, steroids, anticholinergic drugs, antacids, propagermanium, lipid peroxidase inhibitors and so on.

The other pharmaceutical preparations to compensate and/or enhance for preventive and/or therapeutic effect on chronic pancreatitis of the compounds in the present invention include, for example, protease inhibitors, gastric acid inhibitors, antispasmodic drugs (e.g., COMT inhibitors, anti serotonin drugs, etc.), nonsteroidal anti-inflammatory drugs, central analgesics, sedatives, digestive enzymes, antacids, histamine $H_2$ receptor inhibitors, antidepressants, gastric mucosa local anesthetics, gastrointestinal tract function regulators (CCK-A antagonists) and so on.

The other pharmaceutical preparations to compensate and/or enhance for preventive and/or therapeutic effect on esophageal spasm of the compounds in the present invention include, for example, esophageal prokinetic drugs, antidepressants, autonomic nerve modulators and so on.

The other pharmaceutical preparations to compensate and/or enhance for preventive and/or therapeutic effect on gastric atony of the compounds in the present invention include, for example, gastrointestinal tract prokinetic drugs, digestive enzymes, tranquilizers and so on.

The other pharmaceutical preparations to compensate and/or enhance for preventive and/or therapeutic effect on functional dyspepsia of the compounds in the present invention include, for example, antacids, histamine $H_2$ receptor inhibitors, gastrointestinal tract function regulators, gastrointestinal tract prokinetic drugs, antidepressants, tranquilizers, digestive enzymes, proton pump inhibitors, muscarine receptor inhibitors, anticholinergic drugs, defensive factor enhancers, dopamine antagonists and so on.

Antianxiety drugs include, for example, diazepam, oxazolam, flunitrazepam, alprazolam, etizolam, flutazolam, lorazepam, ethyl loflazepate, tofisopam, clotiazepam, γoryzanol and so on.

Tricyclic antidepressants include, for example, amitriptyline, imipramine, clomipramine, nortriptyline, desipramine, amoxapine and so on.

Tetracyclic antidepressants include, for example, mianserin, maprotiline and so on.

Monoamine oxidase inhibitors include, for example, trazodone, fluvoxamine and so on.

Antiparkinson drugs include, for example, levodopa, amantadine, selegiline, bromocriptine, pramipexole, anticholinergic drug, arundic acid and so on.

Anticholinergic drugs include, for example, trihexyphenidyl, biperiden, ipratropium bromide, mepenzolate bromide and so on.

Antiepileptic drugs include, for example, phenobarbital, phenyloin, carbamazepine, valproic acid, clonazepam and so on.

Anti vertigo drugs include, for example, difenidol, betahistine and so on.

Asthmatic drugs include, for example, ephedrine, orciprenaline, salbutamol, procaterol, theophylline, aminophylline, disodium cromoglycate, anticholinergic drug, inhaled steroid and so on.

Inhaled steroids include, for example, beclomethasone, prednisolone and so on.

Antipeptic drugs include, for example, sucralfate and so on.

Antacids include, for example, sodium bicarbonate, magnesium oxide, dry aluminum hydroxide gel, aluminum silicate and so on.

Histamine $H_2$ receptor inhibitors include, for example, famotidine, ranitidine, cimetidine, roxatidine and so on.

Anti gastrin drugs include, for example, proglumide and so on.

Proton pump inhibitors include, for example, omeprazole, lansoprazole and so on.

Muscarine receptor inhibitors include, for example, pirenzepine and so on.

Defensive factor enhancers include, for example, gefarnate, teprenone, sucralfate, aldioxa, cetraxate hydrochloride, omoprostil and so on.

Prostaglandin derivatives include, for example, ornoprostil, misoprostol and so on.

Gastrointestinal tract function regulators include, for example, cisapride, domperidone, sulpiride, metoclopramide, alosetron, trimebutine maleate and so on.

Gastrointestinal tract prokinetic drugs include, for example, cisapride, tegaserod, bethanechol hydrochloride and so on.

Antidiarrheals include, for example, loperamide and so on.

Bulk laxatives include, for example, methylcellulose, carmellose, lactulose and so on.

Saline laxatives include, for example, magnesium sulfate, magnesium oxide and so on.

Stimulant laxatives include, for example, picosulfate, lactulose, castor oil, senna, rhubarb and so on.

Antihypertensive drugs include, for example, nicardipine, nifedipine, nilvadipine, atenolol, allotynol, carteolol, propranolol, metoprolol, prazosin, captopril, enalapril, candesartan cilexetil, losartan potassium and so on.

Antiarrhythmic drugs include, for example, quinidine, procainamide, disopyramide, lidocaine, mexiletine, propranolol, amiodarone, verapamil and so on.

Cardiac stimulants include, for example, digitoxin, digoxin, dopamine, dobutamine, aminophylline, mirnoline and so on.

Dysuria remedies include, for example, oxybutynin, tamsulosin, propiverine and so on.

Local anesthetics include, for example, lidocaine, oxethazaine, procaine hydrochloride, dibucaine hydrochloride, cocaine hydrochloride, tetracaine hydrochloride and so on.

Immunosuppressive drugs include, for example, cyclosporine, tacrolimus, azathiopurine and so on.

Autonomice nerve modulators include, for example, γorizanol and so on.

Cholagogues include, for example, ursodeoxycholic acid and so on.

In order to use the compounds in the present invention, or the compounds in the present invention in combination with the other pharmaceutical preparations by the above-mentioned purpose, these compounds are normally administered to the entire of human body or topically, and orally or parenterally.

The dose of the compounds in the present invention depends on age, body weight, symptom, therapeutic effect, the administration method, the treatment time and so on. In practice, however, these compounds are administered orally once or several times per day each in an amount of from 100 μg to 1000 mg per adult, parentally once or several times per day each in an amount of from 50 μg to 500 mg per adult or continuously administered into vein for 1 hour to 24 hours per day.

It goes without saying that the dose of these compounds may be less than the above-mentioned dose or may need to exceed the above-mentioned range because the dose varies under various conditions as mentioned above.

When the compounds in the present invention, or the compounds in the present invention are administered in combination with the other pharmaceutical preparations, they are used in the form of solid or liquid agent for oral administration, injection, agent for external application, suppository, eye drops or inhalant for parenteral administration or the like.

Examples of the solid agent for oral administration include tablet, pill, capsule, powder, and pellet. Examples of the capsule include hard capsule, and soft capsule.

In such a solid agent for internal application, one or more active materials are used in the form of preparation produced by an ordinary method singly or in admixture with a vehicle (e.g., lactose, mannitol, glucose, microcrystalline cellulose, starch, etc.), binder (e.g., hydroxypropyl cellulose, polyvinyl pyrrolidone, magnesium metasilicoaluminate, etc.), disintegrant (e.g., calcium fibrinoglycolate, etc.), glidant (e.g., magnesium stearate, etc.), stabilizer, dissolution aid (e.g., glutamic acid, aspartic acid, etc.) or the like. The solid agent may be coated with a coating agent (e.g., white sugar, gelatin, hydroxypropyl cellulose, hydroxypropyl methyl cellulose phthalate, etc.) or two or more layers. Alternatively, the solid agent may be capsulized by an absorbable material such as gelatin.

Examples of the liquid agent for oral administration include pharmaceutically acceptable aqueous solution, suspension, emulsion, syrup, and elixir. In such a liquid agent, one or more active agents are dissolved, suspended or emulsified in a commonly used diluent (e.g., purified water, ethanol, mixture thereof, etc.). Furthermore, such a liquid agent may comprise a wetting agent, a suspending agent, an emulsifier, a sweetening agent, a flavor, a fragrance, a preservative, a buffer, etc.

The agent for parenteral administration may be in the form of, e.g., ointment, gel, cream, wet compress, paste, liniment, nebula, inhalant, spray, aerosol, eye drops, collunarium or the like. These agents each contain one or more active materials and are prepared by any known method or commonly used formulation.

The ointment is prepared by any known or commonly used formulation. For example, one or more active materials are triturated or dissolved in a base to prepare such an ointment. The ointment base is selected from known or commonly used materials. In some detail, higher aliphatic acid or higher aliphatic acid ester (e.g., adipic acid, myristic acid, palmitic acid, stearic acid, oleic acid, adipic acid ester, myristic acid ester, palmitic acid ester, stearic acid ester, oleic acid ester, etc.), wax (e.g., beeswax, whale wax, ceresin, etc.), surface active agent (e.g., polyoxyethylenealkylether phosphoric acid ester, etc.), higher alcohol (e.g., cetanol, stearyl alcohol, setostearyl alcohol, etc.), silicon oil (e.g., dimethyl polysiloxane, etc.), hydrocarbon group (e.g., hydrophilic petrolatum, white petrolatum, purified lanolin, liquid paraffin, etc.), glycol (e.g., ethylene glycol, diethylene glycol, propylene glycol, polyethylene glycol, macrogol, etc.), vegetable oil (e.g., castor oil, olive oil, sesame oil, turpentine oil), animal oil (mink oil, vitelline oil, squalane, squalene), water, absorption accelerator and rash preventive may be used singly or in admixture of two or more thereof. The base may further comprise a humectant, a preservative, a stabilizer, an antioxidant, a perfume, etc.

The gel is prepared by any known or commonly used formulation. For example, one or more active materials are dissolved in a base to prepare such a gel. The gel base is selected from known or commonly used materials. For example, lower alcohol (e.g., ethanol, isopropyl alcohol, etc.), gelling agent (e.g., carboxymethyl cellulose, hydroxyethyl cellulose, hydroxypropyl cellulose, ethyl cellulose, etc.), neutralizing agent (e.g., triethanolamine, diisopropanolamine, etc.), surface active agent (e.g., polyethylene glycol monostearate, etc.), gums, water, absorption accelerator, and rash preventive are used singly or in admixture of two or more thereof. The gel base may further comprise a preservative, an antioxidant, a perfume, etc.

The cream is prepared by any known or commonly used formulation. For example, one or more active materials are dissolved in a base to prepare such a cream. The cream base is selected from known or commonly used materials. For example, higher aliphatic acid ester, lower alcohol, hydrocarbon group, polyvalent alcohol (e.g., propylene glycol, 1,3-butylene glycol, etc.), higher alcohol (e.g., 2-hexyl decanol, cetanol, etc.), emulsifier (e.g., polyoxyethylene alkyl ethers, aliphatic acid esters, etc.), water, absorption accelerator, and rash preventive are used singly or in admixture of two or more thereof. The cream base may further comprise a preservative, an antioxidant, a perfume, etc.

The wet compress is prepared by any known or commonly used formulation. For example, one or more active materials are dissolved in a base to prepare a kneaded mixture which is then spread over a support to prepare such a wet compress. The wet compress base is selected from known or commonly used materials. For example, thickening agent (e.g., polyacrylic acid, polyvinyl pyrrolidone, gum arabic, starch, gelatin, methyl cellulose, etc.), wetting agent (e.g., urea, glycerin, propylene glycol, etc.), filler (e.g., kaolin, zinc oxide, talc, calcium, magnesium, etc.), water, dissolution aid, tackifier, and rash preventive may be used singly or in admixture of two or more thereof. The wet compress base may further comprise a preservative, an antioxidant, a perfume, etc.

The pasting agent is prepared by any known or commonly used formulation. For example, one or more active materials are dissolved in a base to prepare a kneaded mixture which is then spread over a support to prepare such a pasting agent. The pasting agent base is selected from known or commonly used materials. For example, polymer base, fat and oil, higher aliphatic acid, tackifier and rash preventive may be used singly or in admixture of two or more thereof. The pasting agent base may further comprise a preservative, an antioxidant, a perfume, etc.

The liniment is prepared by any known or commonly used formulation. For example, one or more active materials are dissolved, suspended or emulsified in water, alcohol (e.g., ethanol, polyethylene glycol, etc.), higher aliphatic acid, glycerin, soap, emulsifier, suspending agent, etc., singly or in combination of two or more thereof, to prepare such a liniment. The liniment may further comprise a preservative, an antioxidant, a perfume, etc.

The nebula, inhalant, spray and aerozol each may comprise a commonly used diluent, additionally, a stabilizer such as sodium hydrogen sulfite and a buffer capable of providing isotonicity such as isotonic agent (e.g., sodium chloride, sodium citrate, or citric acid, etc.). For the process for the preparation of spray, reference can be made to U.S. Pat. Nos. 2,868,691 and 3,095,355.

The injection for parenteral administration consists of solid injection used to be dissolved or suspended in the form of solution, suspension, emulsion and a solvent to be dissolved before use. The injection is prepared by dissolving, suspending or emulsifying one or more active materials in a solvent. As such a solvent there may be used distilled water for injection, physiological saline, vegetable oil, alcohol such as propylene glycol, polyethylene glycol and ethanol, etc., singly or in combination thereof. The injection may further comprise a stabilizer, a dissolution aid (e.g., glutamic acid, aspartic acid, Polysolvate 80 (trade name), etc.), a suspending agent, an emulsifier, a soothing agent, a buffer, a preservative, etc. The injection is sterilized at the final step or prepared by an aseptic process. Alternatively, an aseptic solid agent such as freeze-dried product which has previously been prepared may be rendered aseptic or dissolved in aseptic distilled water for injection or other solvents before use.

The eye drops for parenteral administration consist of eye drop, suspension eye drop, emulsion eye drop, eye drop to be dissolved before use and ointment and so on.

These eye drops are prepared by a known method. For example, it is prepared by dissolving, suspending or emulsifying one or more active materials in a solvent. As such a solvent for eye drops there may be used distilled water, physiological saline, the other aqueous solvent or nonaqueous solvent for injection (e.g., vegetable oil, etc.), etc., singly or in combination thereof. The eye drops may comprise, if necessary, of materials properly selected from tonisity agent (e.g., sodium chloride, concentrated glycerin, etc.), buffer agents (e.g., sodium phosphate, sodium acetate, etc.), surfactants (e.g., polysorbate 80 (trade name), polyoxyl 40 stearate, polyoxyethylene hydrogenated castor oil, etc.), stabilizer (e.g., sodium citrate, sodium edentate, etc.), antiseptic agent (e.g., benzalkonium chloride, paraben, etc.) These are sterilized at the final step or prepared by an aseptic process. Alternatively, an aseptic solid agent such as freeze-dried product which has previously been prepared may be rendered aseptic or dissolved in aseptic distilled water for injection or other solvents before use.

The inhalant for parenteral administration may be in the form of aerosol, powder for inhalation or liquid for inhalation. The liquid for inhalation may be dissolved or suspended in water or other proper medium in use.

These inhalants are prepared by a known method.

For example, the liquid for inhalation is prepared from materials properly selected from preservatives (e.g., benzalconium chloride, Paraben, etc.), colorants, buffering agents (e.g., sodium phosphate, sodium acetate, etc.), isotonic agents (e.g., sodium chloride, concentrated glycerin, etc.), thickening agents (e.g., carboxyvinyl polymer, etc.), absorption accelerators, etc. as necessary.

The powder for inhalation is prepared from materials properly selected from glidants (e.g., stearic acid and salt thereof, etc.), binders (e.g., starch, dextrin, etc.), vehicles (e.g., lactose, cellulose, etc.), colorants, preservatives (e.g., benzalconium chloride, Paraben, etc.), absorption accelerators, etc., if necessary.

In order to administer the liquid for inhalation, a sprayer (e.g., atomizer, nebulizer, etc.) is normally used. In order to administer the powder for inhalation, a powder inhaler is normally used.

Other examples of the composition for parenteral administration include suppository for rectal administration and pessary for vaginal administration prepared by an ordinary formulation comprising one or more active materials.

BEST MODE FOR CARRYING OUT THE INVENTION

The present invention is explained below in detail base on Examples, however, the present invention is not limited thereto. The solvents in parentheses at chromatographic separations section and TLC section show the developing or eluting solvents and the ratios of the solvents used are indicated by volume. The solvents in parentheses indicated in NMR section show solvents used in determination.

All compounds described in the specification are named by using of ACD/Name (Trade mark, Advanced Chemistry Development Inc.) or ACD/Name batch (Trade mark, Advanced Chemistry Development Inc.) which is the computer program to name according to IUPAC rule, or according to IUPAC organic chemistry nomenclature.

In addition, HPLC condition is described below.

Used equipment: Waters LC/MS,

Column: Xterra (trade name) MS $C_{18}$ 5 um, 4.6×50 mm I.D.,

Flow rate: 3 mL/min,

Eluting solvent: A solution: 0.1% trifuloroacetic acid aqueous solution,

B solution: 0.1% trifuloroacetic acid-acetonitrile solution.

Time course of ratio of mixed eluting solvent shows the below table 1.

TABLE 1

| Time (min.) | A solution | B solution |
|---|---|---|
| 0 | 95 | 5 |
| 0.5 | 95 | 5 |
| 3 | 0 | 100 |
| 3.5 | 0 | 100 |
| 3.51 | 95 | 5 |
| 5 | 95 | 5 |

Example 1

N-[3-(trifluoromethyl)phenyl]-1,3,4,9-tetrahydro-2H-β-carboline-2-carboxamide

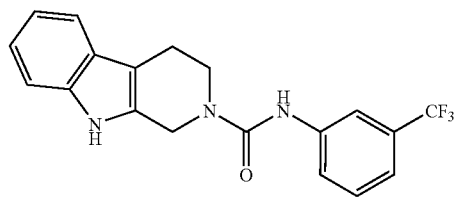

A solution of 2,3,4,9-tetrahydro-1H-β-carboline (172 mg) in dimethylformamide (5 mL) was added by a solution of 1-isocyanato-3-(trifluoromethyl)benzene (173 mg) in dichloromethane (5 mL) and stirred overnight at the room temperature. The mixture was concentrated under reduced pressure and the residue was purified by column chromatography on silica gel (hexane:ethyl acetate=6:1) to give the title compound (205 mg) having the following physical data.

TLC: Rf 0.54 (hexane:ethyl acetate=1:1);

NMR(CD$_3$OD): δ 2.86 (t, J=5.68 Hz, 2H), 3.88 (t, J=5.68 Hz, 2H), 4.74 (s, 2H), 7.00 (m, 2H), 7.27 (m, 2H), 7.42 (m, 2H), 7.64 (m, 1H), 7.81 (s, 1H).

Example 1(1)-Example 1(86)

By the same procedure as described in Example 1 using 2,3,4,9-tetrahydro-1H-β-carboline or the corresponding derivative instead thereof, and 1-isocyanato-3-(trifluoromethyl)benzene or the corresponding derivatives instead thereof, the following compounds in the present invention were obtained.

Example 1(1)

N-(3,5-dimethylphenyl)-1,3,4,9-tetrahydro-2H-β-carboline-2-carboxamide

TLC: Rf 0.46 (ethyl acetate:hexane=1:1);

NMR(CDCl$_3$): δ 2.29 (s, 6H), 2.90 (t, J=5.68 Hz, 2H), 3.80 (t, J=5.68 Hz, 2H), 4.74 (s, 2H), 6.44 (s, 1H), 6.72 (s, 1H), 7.04 (s, 2H), 7.13 (m, 2H), 7.27 (m, 1H), 7.48 (d, J=7.32 Hz, 1H), 8.10 (s, 1H).

Example 1(2)

N-(3-methylphenyl)-1,3,4,9-tetrahydro-2H-β-croboline-2-carboxamide

TLC: Rf 0.43 (ethyl acetate:hexane=1:1);

NMR(CDCl$_3$): δ 2.33 (s, 3H), 2.89 (m, 2H), 3.80 (t, J=5.77 Hz, 2H), 4.74 (t, J=1.46 Hz, 2H), 6.51 (s, 1H), 6.89 (m, 1H), 7.16 (m, 6H), 7.47 (m, 1H), 8.13 (s, 1H).

Example 1(3)

N-(3,5-dimethylphenyl)-6-methoxy-1,3,4,9-tetrahydro-2H-β-carboline-2-carboxamide TLC: Rf 0.34 (ethyl acetate:hexane=1:1);

NMR(CDCl$_3$): δ 2.29 (s, 6H), 2.87 (m, 2H), 3.80 (t, J=5.68 Hz, 2H), 3.86 (s, 3H), 4.72 (s, 2H), 6.41 (s, 1H), 6.72 (s, 1H), 6.81 (dd, J=8.70, 2.47 Hz, 1H), 6.93 (d, J=2.56 Hz, 1H), 7.02 (s, 2H), 7.18 (d, J=8.79 Hz, 1H), 7.90 (s, 1H).

Example 1(4)

6-methoxy-N-(3-methylphenyl)-1,3,4,9-tetrahydro-2H-β-carboline-2-carboxamide

TLC: Rf 0.32 (ethyl acetate:hexane=1:1);
NMR(CDCl$_3$): δ 2.32 (s, 3H), 2.83 (t, J=5.68 Hz, 2H), 3.77 (t, J=5.68 Hz, 2H), 3.84 (s, 3H), 4.68 (s, 2H), 6.58 (s, 1H), 6.79 (dd, J=8.79, 2.38 Hz, 1H), 6.89 (m, 2H), 7.10 (d, J=8.79 Hz, 1H), 7.20 (m, 3H), 8.10 (s, 1H).

Example 1(5)

6-methoxy-N-[2-(trifluoromethyl)phenyl-1,3,4,9-tetrahydro-2H-β-carboline-2-carboxamide TLC: Rf 0.32 (ethyl acetate:hexane=1:1);
NMR(CDCl$_3$): δ 2.90 (m, 2H), 3.83 (m, 2H), 3.86 (s, 3H), 4.77 (s, 2H), 6.83 (dd, J=8.79, 2.56 Hz, 1H), 6.95 (d, J=2.38 Hz, 2H), 7.16 (m, 1H), 7.21 (d, J=8.60 Hz, 1H), 7.53 (t, J=7.87 Hz, 1H), 7.59 (d, J=7.87 Hz, 1H), 7.86 (s, 1H), 8.11 (d, J=8.24 Hz, 1H).

Example 1(6)

N-(3,5-dichlorophenyl)-6-methoxy-1,3,4,9-tetrahydro-2H-β-carboline-2-carboxamide TLC: Rf 0.34 (ethyl acetate: dichloromethane=1:9);
NMR(DMSO-d$_6$): δ 2.73 (m, 2H), 3.74 (s, 3H), 3.80 (t, J=5.49 Hz, 2H), 4.65 (s, 2H), 6.67 (dd, J=8.79, 2.38 Hz, 1H), 6.90 (d, J=2.38 Hz, 1H), 7.12 (t, J=1.74 Hz, 1H), 7.19 (d, J=8.60 Hz, 1H), 7.61 (d, J=1.65 Hz, 2H), 9.04 (s, 1H), 10.71 (s, 1H).

Example 1(7)

1-oxo-N-phenyl-1,3,4,9-tetrahydro-2H-β-carboline-2-carboxamide

TLC: Rf 0.36 (hexane:ethyl acetate=4:1);
NMR(DMSO-d$_6$): δ 3.08 (t, J=6.59 Hz, 2H), 4.29 (t, J=6.68 Hz, 2H), 7.11 (m, 2H), 7.34 (m, 3H), 7.46 (d, J=8.42 Hz, 1H), 7.57 (m, 2H), 7.68 (d, J=8.06 Hz, 1H), 11.36 (s, 1H), 11.91 (s, 1H).

Example 1(8)

N-(3-methylphenyl)-1-oxo-1,3,4,9-tetrahydro-2H-β-carboline-2-carboxamide

TLC: Rf 0.37 (hexane:ethyl acetate=4:1);
NMR(DMSO-d$_6$): δ 2.30 (s, 3H), 3.08 (t, J=6.59 Hz, 2H), 4.28 (t, J=6.68 Hz, 2H), 6.92 (d, J=7.51 Hz, 1H), 7.11 (m, 1H), 7.23 (m, 1H), 7.34 (m 3H), 7.46 (d, J=8.42 Hz, 1H), 7.68 (d, J=8.06 Hz, 1H), 11.32 (s, 1H), 11.90 (s, 1H).

Example 1(9)

N-(3,5-dimethylphenyl)-1-oxo-1,3,4,9-tetrahydro-2H-β-carboline-2-carboxamide

TLC: Rf 0.40 (hexane:ethyl acetate=4:1);
NMR(DMSO-d$_6$): δ 2.26 (s, 6H), 3.07 (t, J=6.59 Hz, 2H), 4.28 (t, J=6.59 Hz, 2H), 6.74 (s, 1H), 7.12 (m, 1H), 7.18 (s, 2H), 7.32 (m, 1H), 7.46 (d, J=8.42 Hz, 1H), 7.68 (d, J=8.06 Hz, 1H), 11.28 (s, 1H), 11.88 (s, 1H).

Example 1(10)

1-(3-fluorophenyl)-N-phenyl-1,3,4,9-tetrahydro-2H-β-carboline-2-carboxamide

TLC: Rf 0.22 (hexane:ethyl acetate=4:1);
NMR(DMSO-d$_6$): δ 2.86 (m, 2H), 3.16 (m, 1H), 4.31 (m, 1H), 6.68 (s, 1H), 7.21 (m, 13H), 8.75 (s, 1H), 11.02 (s, 1H).

Example 1(11)

1-(3-fluorophenyl)-N-(3-methylphenyl)-1,3,4,9-tetrahydro-2H-β-carboline-2-carboxamide TLC: Rf 0.26 (hexane:ethyl acetate=4:1);
NMR(DMSO-d$_6$): δ 2.25 (s, 3H), 2.84 (m, 2H), 3.15 (m, 1H), 4.30 (m, 1H), 6.67 (s, 1H), 6.78 (d, J=7.69 Hz, 1H), 7.08 (m, 6H), 7.39 (m, 5H), 8.68 (s, 1H), 11.02 (s, 1H).

Example 1(12)

N-(3,5-dimethylphenyl)-1-(3-fluorophenyl)-1,3,4,9-tetrahydro-2H-β-carboline-2-carboxamide TLC: Rf 0.29 (hexane:ethyl acetate=4:1);
NMR(DMSO-d$_6$): δ 2.20 (s, 6H), 2.84 (m, 2H), 3.14 (m, 1H), 4.29 (m, 1H), 6.60 (s, 1H), 6.66 (s, 1H), 7.08 (m, 7H), 7.40 (m, 3H), 8.60 (s, 1H), 11.01 (s, 1H).

Example 1(13)

N-(3-methylphenyl)-4,9-dihydrospiro[β-carboline-1,1'-cyclopentane]-2(3H)-carboxamide TLC: Rf 0.37 (hexane:ethyl acetate=4:1);
NMR(DMSO-d$_6$): δ 2.00 (m, 6H), 2.34 (m, 5H), 2.75 (t, J=5.40 Hz, 2H), 3.77 (t, J=5.49 Hz, 2H), 6.73 (d, J=7.32 Hz, 1H), 6.94 (m, 1H), 7.02 (m, 1H), 7.09 (t, J=7.78 Hz, 1H), 7.19 (m, 1H), 7.33 (m, 3H), 8.83 (s, 1H), 10.48 (s, 1H).

Example 1(14)

N-(3-methoxyphenyl)-1,3,4,9-tetrahydro-2H-β-carboline-2-carboxamide

HPLC retention time: 3.77 min.; Mass (ESI, Pos. 20V):m/z 322 (M+H)$^+$.

Example 1(15)

N-[3-(methylthio)phenyl]-1,3,4,9-tetrahydro-2H-β-carboline-2-carboxamide

HPLC retention time: 3.88 min.; Mass (ESI, Pos. 20V):m/z 338 (M+H)$^+$.

Example 1(16)

N-(3-fluorophenyl)-1,3,4,9-tetrahydro-2H-β-carboline-2-carboxamide

HPLC retention time: 3.82 min.; Mass (ESI, Pos. 20V):m/z 310 (M+1)$^+$.

Example 1(17)

N-(4-phenoxyphenyl)-1,3,4,9-tetrahydro-2H-β-carboline-2-carboxamide

HPLC retention time: 4.06 min.; Mass (ESI, Pos. 20V):m/z 767 (2M+H)$^+$, 384 (M+H)$^+$.

Example 1(18)

N-(3,5-difluorophenyl)-1,3,4,9-tetrahydro-2H-β-carboline-2-carboxamide

HPLC retention time: 3.93 min.; Mass (ESI, Pos. 20V):m/z 328 (M+H)$^+$.

Example 1(19)

N-(3-phenoxyphenyl)-3,4-dihydroisoquinoline-2(1H)-carboxamide

HPLC retention time: 4.13 min.; Mass (ESI, Pos. 20V):m/z 345 (M+H)$^+$.

Example 1(20)

N-(4-phenoxyphenyl)-3,4-dihydroisoquinoline-2(1H)-carboxamide

HPLC retention time: 4.06 min.; Mass (ESI, Pos. 20V):m/z 345 (M+H)$^+$.

Example 1(21)

N-(3,4-dichlorophenyl)-3,4-dihydroisoquinoline-2(1H)-carboxamide

HPLC retention time: 4.10 min.; Mass (ESI, Pos. 20V):m/z 323, 321 (M+H)$^+$.

Example 1(22)

Methyl 3-[(8,9-dihydropyrido[2,3-b]-1,6-naphthyridin-7(6H)-ylcarbonyl)amino]benzoate HPLC retention time: 3.07 min.; Mass (ESI, Pos. 20V):m/z 363 (M+H)$^+$.

Example 1(23)

N-[3-(methylthio)phenyl]-8,9-dihydropirido[2,3-b]-1,6-naphthyridine-7(6H)-carboxamide HPLC retention time: 3.16 min.; Mass (ESI, Pos. 20V):m/z 351 (M+H)$^+$.

Example 1(24)

N-(3-fluorophenyl)-8,9-dihydropyrido[2,3-b]-1,6-naphthyridine-7(6H)-carboxamide

HPLC retention time: 3.09 min.; Mass (ESI, Pos. 20V):m/z 323 (M+H)$^+$.

Example 1(25)

N-(3,5-difluorophenyl)-8,9-dihydropyrido[2,3-b]-1,6-naphthyridine-7(6H)-carboxamide HPLC retention time: 3.18 min.; Mass (ESI, Pos. 20V):m/z 341 (M+H)$^+$.

Example 1(26)

6-methyl-N-[2-(trifluoromethyl)phenyl]-3,4-dihydroquinoline-1(2H)-carboxamide

HPLC retention time: 4.17 min.; Mass (ESI, Pos. 20V):m/z 335 (M+H)$^+$.

Example 1(27)

methyl 3-{[(6-methyl-3,4-dihydroquinolin-1(2H)-yl)carbonyl]amino}benzoate

HPLC retention time: 3.91 min.; Mass (ESI, Pos. 20V):m/z 325 (M+H)$^+$.

Example 1(28)

6-methyl-N-[3-(trifluoromethyl)phenyl]-3,4-dihydroquinoline-1(2H)-carboxamide

HPLC retention time: 4.17 min.; Mass (ESI, Pos. 20V):m/z 335 (M+H)$^+$.

Example 1(29)

6-methyl-N-[3-(methylthio)phenyl]-3,4-dihydroquinoline-1(2H)-carboxamide

HPLC retention time: 4.04 min.; Mass (ESI, Pos. 20V):m/z 313 (+H)$^+$.

Example 1(30)

N-(2,6-dichloropyridin-4-yl)-6-methyl-3,4-dihydroquinoline-1(2H)-carboxamide

HPLC retention time: 4.11 min.; Mass (ESI, Pos. 20V):m/z 338, 336 (M+H)$^+$.

Example 1(31)

N-phenyl-1,3,4,9-tetrahydro-2H-β-carboline-2-carboxamide

HPLC retention time: 3.69 min.; Mass (ESI, Pos. 20V):m/z 292 (M+H)$^+$.

Example 1(32)

N-butyl-1,3,4,9-tetrahydro-2H-β-carboline-2-carboxamide

HPLC retention time: 3.62 min.; Mass (ESI, Pos. 20V):m/z 272 (M+H)$^+$.

Example 1(33)

N-cyclohexyl-1,3,4,9-tetrahydro-2H-β-carboline-2-carboxamide

HPLC retention time: 3.73 min.; Mass (ESI, Pos. 20V):m/z 298 (M-+H)$^+$.

Example 1(34)

N-(3,4-dichlorophenyl)-1,3,4,9-tetrahydro-2H-β-carboline-2-carboxamide

HPLC retention time: 4.00 min; Mass (ESI, Pos. 20V):m/z 362, 360 (M+H)$^+$.

Example 1(35)

N-(2-methoxyphenyl)-1,3,4,9-tetrahydro-2H-β-carboline-2-carboxamide

HPLC retention time: 3.78 min.; Mass (ESI, Pos. 20V):m/z 322 (M+H)$^+$.

Example 1(36)

N-(4-methoxyphenyl)-1,3,4,9-tetrahydro-2H-β-carboline-2-carboxamide

HPLC retention time: 3.62 min.; Mass (ESI, Pos. 20V):m/z 322 (M+H)$^+$.

Example 1(37)

N-[2-(trifluoromethyl)phenyl]-1,3,4,9-tetrahydro-2H-β-carboline-2-carboxamide

HPLC retention time: 3.82 min.; Mass (ESI, Pos. 20V):m/z 360 (M+H)$^+$.

Example 1(38)

N-(2-fluorophenyl)-1,3,4,9-tetrahydro-2H-β-carboline-2-carboxamide

HPLC retention time: 3.67 min.; Mass (ESI, Pos. 20V):m/z 310 (M+H)$^+$.

Example 1(39)

N-benzyl-1,3,4,9-tetrahydro-2H-β-carboline-2-carboxamide

HPLC retention time: 3.67 min.; Mass (ESI, Pos. 20V):m/z 306 (M+H)$^+$.

Example 1(40)

N-(4-fluorophenyl)-1,3,4,9-tetrahydro-2H-β-carboline-2-carboxamide

HPLC retention time: 3.73 min.; Mass (ESI, Pos. 20V):m/z 310 (M+H)$^+$.

Example 1(41)

N-(3,5-dichlorophenyl)-1,3,4,9-tetrahydro-2H-β-carboline-2-carboxamide

HPLC retention time: 4.08 min.; Mass (ESI, Pos. 20V):m/z 362, 360 (M+H)$^+$.

Example 1(42)

N-pentyl-1,3,4,9-tetrahydro-2H-β-carboline-2-carboxamide

HPLC retention time: 3.75 min.; Mass (ESI, Pos. 20V):m/z 571 (2M+H)$^+$, 286 (M+H)$^+$.

Example 1(43)

N-(2-phenylethyl)-1,3,4,9-tetrahydro-2H-β-carboline-2-carboxamide

HPLC retention time: 3.73 min.; Mass (ESI, Pos. 20V):m/z 320 (M+H)$^+$.

Example 1(44)

N-(2,3-dichlorophenyl)-1,3,4,9-tetrahydro-2H-β-carboline-2-carboxamide

HPLC retention time: 4.00 min.; Mass (ESI, Pos. 20V):m/z 362, 360 (M+H)$^+$.

Example 1(45)

ethyl 3-[(1,3,4,9-tetrahydro-2H-β-carbolin-2-ylcarbonyl)amino]benzoate

HPLC retention time: 3.80 min.; Mass (ESI, Pos. 20V):m/z 727 (2M+H)$^+$, 364 (M+H)$^+$.

Example 1(46)

N-(3-phenoxyphenyl)-1,3,4,9-tetrahydro-2H-β-carboline-2-carboxamide

HPLC retention time: 4.04 min.; Mass (ESI, Pos. 20V):m/z 384 (M+H)$^+$.

Example 1(47)

N-[3,5-bis(trifluoromethyl)phenyl]-1,3,4,9-tetrahydro-2H-β-carboline-2-carboxamide HPLC retention time: 4.19 min.; Mass (ESI, Pos. 20V):m/z 428 (M+H)$^+$.

Example 1(48)

N-[3-fluoro-5-(trifluoromethyl)phenyl]-1,3,4,9-tetrahydro-2H-β-carboline-2-carboxamide HPLC retention time: 4.04 min.; Mass (ESI, Pos. 20V):m/z 378 (M+H)$^+$.

Example 1(49)

N-(3-chloro-5-fluorophenyl)-1,3,4,9-tetrahydro-2H-β-carboline-2-carboxamide

HPLC retention time: 3.99 min.; Mass (ESI, Pos. 20V):m/z 344 (M+H)$^+$.

Example 1(50)

N-[3-(cyclopentyloxy)phenyl]-1,3,4,9-tetrahydro-2H-β-carboline-2-carboxamide

HPLC retention time: 4.04 min.; Mass (ESI, Pos. 20V):m/z 376 (M+H)$^+$.

Example 1(51)

N-[3-(cyclohexyloxy)phenyl]-1,3,4,9-tetrahydro-2H-β-carboline-2-carboxamide

HPLC retention time: 4.11 min.; Mass (ESI, Pos. 20V):m/z 390 (M+H)$^+$.

Example 1(52)

N-(2,6-dichloropyridin-4-yl)-1,3,4,9-tetrahydro-2H-β-carboline-2-carboxamide

HPLC retention time: 3.88 min.; Mass (ESI, Pos. 20V):m/z 363, 361 (M+H)$^+$.

Example 1(53)

6-methoxy-N-phenyl-1-(trifluoromethyl)-1,3,4,9-tetrahydro-2H-β-carboline-2-carboxamide HPLC retention time: 3.86 min.; Mass (ESI, Pos. 20V):m/z 390 (M+H)$^+$.

Example 1(54)

N-(4-chlorophenyl)-6-methoxy-1-(trifluoromethyl)-1,3,4,9-tetrahydro-2H-β-carboline-carboxamide HPLC retention time: 4.00 min.; Mass (ESI, Pos. 20V):m/z 426, 424 (M+H)$^+$.

Example 1(55)

N-(3-chlorophenyl)-6-methoxy-1-(trifluoromethyl)-1,3,4,9-tetrahydro-2H-β-carboline-2-carboxamide HPLC retention time: 4.00 min.; Mass (ESI, Pos. 20V):m/z 426, 424 (M+H)$^+$.

Example 1(56)

N-cyclohexyl-6-methoxy-1-(trifluoromethyl)-1,3,4,9-tetrahydro-2H-β-carboline-2-carboxamide HPLC retention time: 3.93 min.; Mass (ESI, Pos. 20V):m/z 791 (2M+H)$^+$, 396 (M+H)$^+$.

Example 1(57)

N-(3,4-dichlorophenyl)-6-methoxy-1-(trifluoromethyl)-1,3,4,9-tetrahydro-2H-β-carboline-2-carboxamide HPLC retention time: 4.15 min.; Mass (ESI, Pos. 20V):m/z 460, 458 (M+H)$^+$.

Example 1(58)

6-methoxy-1-(trifluoromethyl)-N-[3-(trifluoromethyl)phenyl]-1,3,4,9-tetrahydro-2H-β-carboline-2-carboxamide HPLC retention time: 4.06 min.; Mass (ESI, Pos. 20V):m/z 458 (M+H)$^+$.

Example 1(59)

N-hexyl-6-methoxy-1-(trifluoromethyl)-1,3,4,9-tetrahydro-2H-β-carboline-2-carboxamide HPLC retention time: 4.04 min.; Mass (ESI, Pos. 20V):m/z 795 (2M+H), 398 (M+H)$^+$.

Example 1(60)

6-methoxy-N-(3-methoxyphenyl)-1-(trifluoromethyl)-1,3,4,9-tetrahydro-2H-β-carboline-2-carboxamide HPLC retention time: 3.86 min.; Mass (ESI, Pos. 20V):m/z 420 (M+H)$^+$.

Example 1(61)

6-methoxy-N-(4-methoxyphenyl)-1-(trifluoromethyl)-1,3,4,9-tetrahydro-2H-β-carboline-2-carboxamide HPLC retention time: 3.80 min.; Mass (ESI, Pos. 20V):m/z 420 (M+H)$^+$.

Example 1(62)

N-(3-fluorophenyl)-6-methoxy-1-(trifluoromethyl)-1,3,4,9-tetrahydro-2H-β-carboline-2-carboxamide HPLC retention time: 3.93 min.; Mass (ESI, Pos. 20V):m/z 408 (M+H)$^+$.

Example 1(63)

N-benzyl-6-methoxy-1-(trifluoromethyl)-1,3,4,9-tetrahydro-2H-β-carboline-2-carboxamide HPLC retention time: 3.82 min.; Mass (ESI, Pos. 20V):m/z 404 (M+H)$^+$.

Example 1(64)

N-(4-fluorophenyl)-6-methoxy-1-(trifluoromethyl)-1,3,4,9-tetrahydro-2H-β-carboline-2-carboxamide HPLC retention time: 3.88 min.; Mass (ESI, Pos. 20V):m/z 408 (M+H)$^+$.

Example 1(65)

6-methoxy-1-(trifluoromethyl)-N-[4-(trifluoromethyl)phenyl]-1,3,4,9-tetrahydro-2H-β-carboline-2-carboxamide HPLC retention time: 4.06 min.; Mass (ESI, Pos. 20V):m/z 458 (M+H)$^+$.

Example 1(66)

N-(3,5-dichlorophenyl)-6-methoxy-1-(trifluoromethyl)-1,3,4,9-tetrahydro-2H-β-carboline-2-carboxamide HPLC retention time: 4.22 min.; Mass (ESI, Pos. 20V):m/z 458 (M+H)$^+$.

Example 1(67)

N-(2,5-dichlorophenyl)-6-methoxy-1-(trifluoromethyl)-1,3,4,9-tetrahydro-2H-β-carboline-2-carboxamide HPLC retention time: 4.13 min.; Mass (ESI, Pos. 20V):m/z 460, 458 (M+H)$^+$.

Example 1(68)

6-methoxy-N-pentyl-1-(trifluoromethyl)-1,3,4,9-tetrahydro-2H-β-carboline-2-carboxamide HPLC retention time: 3.91 min.; Mass (ESI, Pos. 20V):m/z 767 (2M+H)$^+$, 384 (M+H)$^+$.

Example 1(69)

6-methoxy-N-(2-phenylethyl)-1-(trifluoromethyl)-1,3,4,9-tetrahydro-2H-β-carboline-2-carboxamide HPLC retention time: 3.86 min.; Mass (ESI, Pos. 20V):m/z 418 (M+H)$^+$.

Example 1(70)

N-(2,3-dichlorophenyl)-6-methoxy-1-(trifluoromethyl)-1,3,4,9-tetrahydro-2H-β-carboline-2-carboxamide HPLC retention time: 4.06 min.; Mass (ESI, Pos. 20V):m/z 460, 458 (M+H)$^+$.

Example 1(71)

N-(3-cyanophenyl)-6-methoxy-1-(trifluoromethyl)-1,3,4,9-tetrahydro-2H-β-carboline-2-carboxamide HPLC retention time: 3.84 min.; Mass (ESI, Pos. 20V):m/z 829 (2M+H)$^+$, 415 (M+H)$^+$.

Example 1(72)

ethyl 4-({[6-methoxy-1-(trifluoromethyl)-1,3,4,9-tetrahydro-2H-β-carbolin-2-yl]carbonyl}amino)benzoate HPLC retention time: 3.97 min.; Mass (ESI, Pos. 20V):m/z 462 (M+H)$^+$.

Example 1(73)

6-methoxy-N-(4-phenoxyphenyl)-1-(trifluoromethyl)-1,3,4,9-tetrahydro-2H-β-carboline-2-carboxamide HPLC retention time: 4.13 min.; Mass (ESI, Pos. 20V):m/z 482 (M+H)$^+$.

Example 1(74)

ethyl 3-({[6-methoxy-1-(trifluoromethyl)-1,3,4,9-tetrahydro-2H-β-carbolin-2-yl]carbonyl}amino)benzoate HPLC retention time: 3.97 min.; Mass (ESI, Pos. 20V):m/z 462 (M+H)$^+$.

Example 1(75)

6-methoxy-N-(3-phenoxyphenyl)-1-(trifluoromethyl)-1,3,4,9-tetrahydro-2H-β-carboline-2-carboxamide HPLC retention time: 4.13 min.; Mass (ESI, Pos. 20V):m/z 482 (M+H)$^+$.

Example 1(76)

N-(4-cyanophenyl)-6-methoxy-1-(trifluoromethyl)-1,3,4,9-tetrahydro-2H-β-carboline-2-carboxamide HPLC retention time: 3.84 min.; Mass (ESI, Pos. 20V):m/z 415 (M+H)$^+$.

Example 1(77)

N-(3,5-difluorophenyl)-6-methoxy-1-(trifluoromethyl)-1,3,4,9-tetrahydro-2H-β-carboline-2-carboxamide HPLC retention time: 4.00 min.; Mass (ESI, Pos. 20V):m/z 426 (M+H)$^+$.

Example 1(78)

N-[3,5-bis(trifluoromethyl)phenyl]-6-methoxy-1-(trifluoromethyl)-1,3,4,9-tetrahydro-2H-β-carboline-2-carboxamide HPLC retention time: 4.26 min.; Mass (ESI, Pos. 20V):m/z 526 (M+H)$^+$.

Example 1(79)

N-[3-fluoro-5-(trifluoromethyl)phenyl]-6-methoxy-1-(trifluoromethyl)-1,3,4,9-tetrahydro-2H-β-carboline-2-carboxamide HPLC retention time: 4.13 min.; Mass (ESI, Pos. 20V):m/z 476 (M+H)+.

Example 1(80)

N-(3-chloro-5-fluorophenyl)-6-methoxy-1-(trifluoromethyl)-1,3,4,9-tetrahydro-2H-β-carboline-2-carboxamide HPLC retention time: 4.10 min.; Mass (ESI, Pos. 20V):m/z 444, 442 (M+H)+.

Example 1(81)

N-[3-(cyclopentyloxy)phenyl]-6-methoxy-1-(trifluoromethyl)-1,3,4,9-tetrahydro-2H-β-carboline-2-carboxamide HPLC retention time: 4.17 min.; Mass (ESI, Pos. 20V):m/z 947 (2M+H)+, 474 (M+H)+.

Example 1(82)

N-[3-(cyclohexyloxy)phenyl]-6-methoxy-1-(trifluoromethyl)-1,3,4,9-tetrahydro-2H-β-carboline-2-carboxamide HPLC retention time: 4.26 min.; Mass (ESI, Pos. 20V):m/z 488 (M+H)+.

Example 1(83)

N-(2,6-dichloropyridin-4-yl)-6-methoxy-1-(trifluoromethyl)-1,3,4,9-tetrahydro-2H-β-carboline-2-carboxamide HPLC retention time: 4.02 min.; Mass (ESI, Pos. 20V):m/z 461, 459 (M+H)+.

Example 1(84)

methyl 3-[(1,3,4,9-tetrahydro-2H-β-carbolin-2-ylcarbonyl)amino]benzoate

HPLC retention time: 3.77 min.; Mass (ESI, Pos. 20V):m/z 699 (2M+H)+, 350 (M+H)+.

Example 1(85)

methyl 3-{[(6-methoxy-1,3,4,9-tetrahydro-2H-β-carbolin-2-yl)carbonyl]amino}benzoate HPLC retention time: 3.17 min.; Mass (ESI, Pos. 20V):m/z 759 (2M+H)+, 380 (M+H)+.

Example 1(86)

N-(3-chlorophenyl)-1,3,4,9-tetrahydro-2H-β-carboline-2-carboxamide

TLC: Rf 0.49 (hexane:ethyl acetate=1:1);
NMR(CD$_3$OD): δ 2.85 (m, 2H), 3.87 (t, J=9.00 Hz, 2H), 4.73 (t, J=1.46 Hz, 2H), 7.01 (m, 3H), 7.22 (t, J=8.06 Hz, 1H), 7.29 (m, 2H), 7.40 (m, 1H), 7.53 (t, J=2.01 Hz, 1H).

Example 2

2-acetyl-1-(3-fluorophenyl)-2,3,4,9-tetrahydro-1H-β-carboline

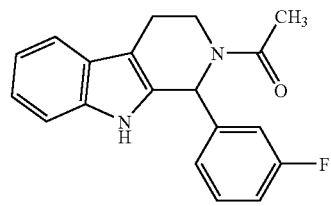

A solution of 1-(3-fluorophenyl)-2,3,4,9-tetrahydro-1H-β-carboline (161 mg) in tetrahydrofuran (60 mL) was added by triethylamine (0.09 mL) and acetylchloride (0.045 mL) successively under the ice and the mixture was stirred for 3 hours at the room temperature. The reaction mixture was added by 1N hydrochloric acid. The deposited crystals were washed with water, dispersed into methanol and concentrated under reduced pressure to give the title compounds (158 mg) having the following physical data.

TLC: Rf 0.20 (hexane:ethyl acetate=1:1);
NMR(DMSO-d$_6$): δ 2.18 (m, 3H), 2.83 (m, 2H), 3.23 (m, 1H), 4.14 (m, 1H), 6.60 (m, 1H), 7.06 (m, 5H), 7.39 (m, 3H), 10.94 (m, 1H).

Example 2(1)-Example 2(5)

By the same procedure as described in Example 2 using the corresponding derivative instead of 1-(3-fluorophenyl)-2,3,4,9-tetrahydro-1H-β-carboline, the following compounds in the present invention were obtained.

Example 2(1)

2-acetyl-1-(trifluoromethyl)-1,2,3,4,5,10-hexahydroazepino[3,4-b]indole

TLC: Rf 0.38 (hexane:ethyl acetate=2:1);
NMR(DMSO-d$_6$): δ 1.64 (m, 1H), 2.16 (m, 4H), 2.74 (m, 1H), 3.10 (m, 1H), 3.58 (m, 1H), 4.44 (m, 1H), 6.38 (m, 1H), 7.07 (m, 2H), 7.36 (m, 1H), 7.51 (d, J=7.87 Hz, 1H), 11.13 (m, 1H).

Example 2(2)

2-acetyl-1-(3-fluorophenyl)-1,2,3,4,5,10-hexahydroazepino[3,4-b]indole

TLC: Rf 0.17 (hexane:ethyl acetate=2:1);
NMR(DMSO-d$_6$): δ 1.80 (m, 2H), 2.20 (m, 3H), 2.64 (m, 1H), 3.03 (m, 2H), 4.02 (m, 1H), 7.07 (m, 8H), 7.50 (m, 1H), 11.09 (m, 1H).

Example 2(3)

2-acetyl-1,2,3,4,5,10-hexahydroazepino[3,4-b]indole

TLC: Rf 0.51 (dichloromethane: methanol: ammonia water=9:1:0.1);

NMR(DMSO-$d_6$): δ 1.86 (1,2H), 2.00 (m, 3H), 2.82 (m, 2H), 3.75 (m, 2H), 4.70 (m, 2H), 6.97 (m, 2H), 7.25 (m, 1H), 7.39 (m, 1H), 10.99 (s, 1H).

Example 2(4)

2-acetyl-6-methoxy-1-(trifluoromethyl)-2,3,4,9-tetrahydro-1H-β-carboline

TLC: Rf 0.28 (hexane:ethyl acetate=2:1);

NMR(DMSO-$d_6$): δ 2.22 (m, 3H), 2.88 (m, 2H), 3.53 (m, 1H), 3.75 (s, 3H), 4.52 (m, 1H), 6.09 (m, 1H), 6.78 (dd, J=8.79, 2.56 Hz, 1H), 6.96 (d, J=2.38 Hz, 1H), 7.30 (m, 1H), 10.88 (m, 1H).

Example 2(5)

2-acetyl-7-methoxy-1-(trifluoromethyl)-1,2,3,4,5,10-hexahydroazepino[3,4-b]indole TLC: Rf 0.36 (hexane:ethyl acetate=2:1);

NMR(DMSO-$d_6$): δ 1.65 (m, 1H), 2.08 (m, 1H), 2.18 (m, 3H), 2.71 (m, 1H), 3.06 (m, 1H), 3.56 (m, 1H), 3.75 (s, 3H), 4.36 (m, 1H), 6.46 (m, 2H), 6.99 (d, J=2.38 Hz, 1H), 7.25 (m, 1H), 11.04 (m, 1H).

Example 3

1-(trifluoromethyl)-1,2,3,4,5,10-hexahydroazepino[3,4-b]indole

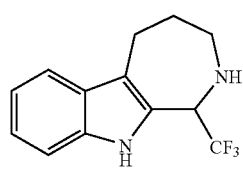

A solution of [3-(1H-indol-3-yl)propyl]amine (866 mg) in acetic acid (50 mL) was added by 1-ethoxy-2,2,2-trifluoroethanol (1.21 g) and refluxed for 5 hours. The mixture was cooled down and then concentrated under reduced pressure. The residue was added by ethyl acetate and hexane and extracted by 1N hydrochloric acid. The aqueous layer was neutralized with 1N sodium hydroxide aqueous solution, added by sodium chloride to saturate and then extracted by ethyl acetate. The organic layer was dried over anhydrous magnesium sulfate and then concentrated under reduced pressure to give the title compounds (654 mg) having the following physical data.

TLC: Rf 0.49 (dichloromethane:methanol:ammonia water=9:1:0.1);

NMR(CDCl$_3$): δ 1.93 (m, 2H), 2.95 (m, 2H), 3.17 (m, 1H), 3.40 (m, 1H), 4.56 (q, J=8.24 Hz, 1H), 7.16 (m, 2H), 7.33 (m, 1H), 7.55 (d, J=7.87 Hz, 1H), 8.00 (s, 1H).

Example 4

2-(chloroacetyl)-1-(3-fluorophenyl)-1,2,3,4,5,10-hexahydroazepino[3,4-b]indole

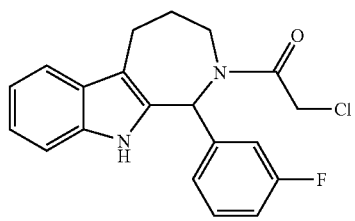

A solution of 1-(3-fluorophenyl)-1,2,3,4,5,10-hexahydroazepino[3,4-b]indole (282 mg) in tetrahydrofuran (10 mL) was added by triethylamine (0.17 mL) and chloroacetylchloride (0.08 mL) successively under the ice and the mixture was stirred for 2 hours at the room temperature. The organic layer was washed with water, saturated sodium bicarbonate and saturated brine successively, dried over anhydrous magnesium sulfate and then concentrated under reduced pressure. The residue was purified by column chromatography on silica gel (hexane:ethyl acetate=3:1) to give the title compounds (202 mg) having the following physical data.

TLC: Rf 0.24 (hexane:ethyl acetate=4:1);

NMR(CDCl$_3$): δ 1.95 (m, 2H), 2.78 (m, 1H), 3.23 (m, 2H), 4.13 (m, 3H), 7.12 (m, 8H), 7.57 (m, 1H), 8.36 (m, 1H).

Example 5

1-(3-fluorophenyl)-2-({[5-(trifluoromethyl)pyridin-2-yl]thio}acetyl)-1,2,3,4,5,10-hexahydroazepino[3,4-b]indole

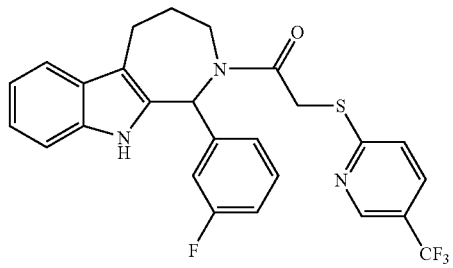

A solution of the compound prepared in Example 4 (88 mg) in dimethylformamide (1 mL) was added by 5-(trifluoromethyl)pyridine-2-thiol (48 mg), potassium carbonate (56 mg) and tetra-n-butyl ammonium iodide (12 mg) successively and the mixture was stirred for 4 hours at the room temperature. The reaction mixture was added by water and extracted by ethyl acetate. The organic layer was washed with saturated brine, dried over anhydrous magnesium sulfate and then concentrated under reduced pressure. The residue was washed with a mixed solvent of hexane and ethyl acetate to give the title compounds (39 mg) having the following physical data.
TLC: Rf 0.19 (hexane:ethyl acetate=4:1);
NMR(DMSO-$d_6$): δ 1.82 (m, 2H), 2.67 (m, 1H), 3.08 (m, 2H), 4.36 (m, 3H), 7.18 (m, 10H), 7.95 (m, 1H), 8.47 (m, 1H), 11.09 (m, 1H).

Example 5(1)-Example 5(11)

By the same procedure as described in Example 5 using the compounds prepared in Example 4 or the corresponding derivative instead thereof and 5-(trifluoromethyl)pyridine-2-thiol or the corresponding derivative instead thereof, the following compounds in the present invention were obtained.

Example 5(1)

2-({[5-(trifluoromethyl)pyridin-2-yl]thio}acetyl)-2,3,4,9-tetrahydro-1H-β-carboline TLC: Rf 0.38 (hexane:ethyl acetate=1:1);
NMR(CDCl$_3$): δ 2.89 (m, 2H), 3.98 (m, 2H), 4.33 (m, 2H), 4.87 (m, 2H), 7.15 (m, 2H), 7.34 (m, 2H), 7.50 (m, 1H), 7.68 (dd, J=8.42, 2.38 Hz, 1H), 7.93 (m, 1H), 8.60 (m, if).

Example 5(2)

2-{[(2,5-dimethoxyphenyl)thio]acetyl}-2,3,4,9-tetrahydro-1H-β-carboline

TLC: Rf 0.23 (hexane:ethyl acetate=1:1);
NMR(CDCl$_3$): δ 2.85 (m, 2H), 3.82 (m, 10H), 4.77 (m, 2H), 6.76 (m, 2H), 7.10 (m, 3H), 7.34 (m, 1H), 7.48 (m, 1H), 7.87 (m, 1H).

Example 5(3)

6-methoxy-1-(trifluoromethyl)-2-({[5-(trifluoromethyl)pyridin-2-yl]thio}acetyl-2,3,4,9-tetrahydro-1H-β-carboline TLC: Rf 0.43 (hexane:ethyl acetate=2:1);
NMR(DMSO-$d_6$): δ 2.93 (m, 2H), 3.60 (m, 1H), 3.76 (s, 3H), 4.57 (m, 3H), 6.29 (m, 1H), 6.79 (m, 1H), 6.99 (m, 1H), 7.31 (m, 1H), 7.58 (m, 1H), 7.99 (m, 1H), 8.57 (m, 1H), 10.95 (s, 1H).

Example 5(4)

2-{[(2,5-dimethoxyphenyl)thio]acetyl}-1-(3-fluorophenyl)-1,2,3,4,5,10-hexahydroazepino[3,4-b]indole TLC: Rf 0.40 (hexane:ethyl acetate=2:1);
NMR(DMSO-$d_6$): δ 1.79 (m, 2H), 2.66 (m, 1H), 3.05 (m, 2H), 3.66 (m, 6H), 4.10 (m, 3H), 6.92 (m, 9H), 7.36 (m, 2H), 7.51 (m, 1H), 11.09 (m, 1H).

Example 5(5)

1-(trifluoromethyl)-2-({[5-(trifluoromethyl)pyridin-2-yl]thio}acetyl)-1,2,3,4,5,10-hexahydroazepino[3,4-b]indole TLC: Rf 0.36 (hexane:ethyl acetate=4:1);
NMR(DMSO-$d_6$): δ 2.06 (m, 2H), 2.77 (m, 1H), 3.13 (m, 1H), 3.68 (m, 1H), 4.28 (m, 3H), 6.56 (m, 1H), 7.08 (m, 2H), 7.37 (m, 1H), 7.56 (m, 2H), 7.96 (m, 1H), 8.41 (m, 1H), 11.16 (m, 1H).

Example 5(6)

2-{[(2,5-dimethoxyphenyl)thio]acetyl}-1-(trifluoromethyl)-1,2,3,4,5,10-hexahydroazepino[3,4-b]indole TLC: Rf 0.21 (hexane:ethyl acetate=4:1);
NMR(DMSO-$d_6$): δ 2.02 (m, 2H), 2.76 (m, 1H), 3.11 (m, 1H), 3.67 (m, 7H), 4.05 (m, 2H), 4.48 (m, 1H), 6.61 (m, 4H), 7.01 (m, 1H), 7.12 (m, 1H), 7.37 (m, 1H), 7.52 (d, J=7.87 Hz, 1H), 11.22 (m, 1H).

Example 5(7)

2-({[5-(trifluoromethyl)pyridin-2-yl]thio}acetyl)-1,2,3,4,5,10-hexahydroazepino[3,4-b]indole TLC: Rf 0.26 (hexane:ethyl acetate=3:2);
NMR(DMSO-$d_6$): δ 1.91 (m, 2H), 2.86 (m, 2H), 3.84 (m, 2H), 4.27 (m, 2H), 4.80 (m, 2H), 6.98 (m, 2H), 7.26 (m, 1H), 7.45 (m, 2H), 7.87 (m, 1H), 8.46 (m, 1H), 11.00 (m, 1H).

Example 5(8)

2-{[(2,5-dimethoxyphenyl)thio]acetyl}-1,2,3,4,5,10-hexahydroazepino[3,4-b]indole TLC: Rf 0.20 (hexane:ethyl acetate=3:2);
NMR(DMSO-$d_6$): δ 1.90 (m, 2H), 2.84 (m, 2H), 3.57 (m, 3H), 3.81 (m, 7H), 4.76 (m, 2H), 6.67 (m, 1H), 6.83 (m, 2H), 6.98 (m, 2H), 7.26 (m, 1H), 7.41 (m, 1H), 11.01 (m, 1H).

Example 5(9)

2-{[(2,5-dimethoxyphenyl)thio]acetyl}-6-methoxy-1-(trifluoromethyl)-2,3,4,9-tetrahydro-1H-β-carboline TLC: Rf 0.29 (hexane:ethyl acetate=2:1);
NMR(DMSO-$d_6$): δ 2.88 (m, 2H), 3.59 (m, 10H), 4.10 (m, 2H), 4.50 (m, 1H), 6.20 (m, 1H), 6.75 (m, 2H), 6.92 (m, 3H), 7.30 (m, 1H), 10.90 (m, 1H).

Example 5(10)

7-methoxy-1-(trifluoromethyl)-2-({[5-(trifluoromethyl)pyridin-2-yl]thio}acetyl)-1,2,3,4,5,10-hexahydroazepino[3,4-b]indole TLC: Rf 0.34 (hexane:ethyl acetate=3:1);
NMR(DMSO-$d_6$): δ 1.93 (m, 1H), 2.13 (m, 1H), 2.77 (m, 1H), 3.11 (m, 1H), 3.66 (m, 1H), 3.75 (m, 3H), 4.44 (m, 3H), 6.61 (m, 2H), 7.02 (d, J=2.38 Hz, 1H), 7.26 (m, 1H), 7.56 (m, 1H), 7.95 (m, 1H), 8.46 (m, 1H), 11.05 (m, 1H).

Example 5(11)

2-{[(2,5-dimethoxyphenyl)thio]acetyl}-7-methoxy-1-(trifluoromethyl)-1,2,3,4,5,10-hexahydroazepino[3,4-b]indole TLC: Rf 0.35 (hexane:ethyl acetate=2:1);
NMR(DMSO-$d_6$): δ 1.85 (m, 1H), 2.11 (m, 1H), 2.72 (m, 1H), 3.08 (m, 1H), 3.66 (m, 10H), 4.02 (d, J=15.01 Hz, 1H), 4.21 (m, 1H), 4.46 (m, 1H), 6.64 (m, 5H), 7.00 (d, J=2.38 Hz, 1H), 7.26 (m, 1H), 11.08 (m, 1H).

Example 6

N-(3-methylphenyl)-1-(trifluoromethyl)-3,4,5,10-tetrahydroazepino[3,4-b]indole-2(1H)-carboxamide

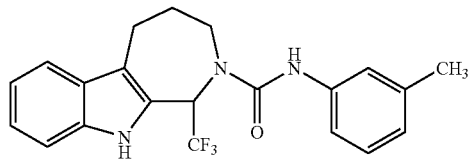

By the same procedure as described in Example 1 using the compounds prepared in Example 3 instead of 2,3,4,9-tetrahydro-1H-β-carboline and 1-isocyanato-3-methylbenzene instead of 1-isocyanato-3-(trifluoromethyl)benzene, the title compounds having the following physical data were obtained.

TLC: Rf 0.28 (hexane:ethyl acetate=4:1);

NMR(DMSO-$d_6$): δ 1.75 (m, 1H), 2.06 (m, 1H), 2.24 (s, 3H), 2.76 (m, 1H), 3.08 (m, 1H), 3.55 (m, 1H), 4.42 (m, 1H), 6.59 (m, 1H), 6.81 (d, J=7.69 Hz, 1H), 7.00 (m, 1H), 7.11 (m, 2H), 7.26 (m, 2H), 7.33 (d, J=8.06 Hz, 1H), 7.51 (d, J=7.69 Hz, 1H), 8.77 (s, 1H), 11.27 (s, 1H).

Example 6(1)-Example 6(69)

By the same procedure as described in Example 6 using the compounds prepared in Example 3 or the corresponding derivative instead thereof and 1-isocyanato-3-methylbenzene or the corresponding derivative instead thereof, the following compounds in the present invention ware obtained.

Example 6(1)

N-(3-methylphenyl)-3,4,5,10-tetrahydroazepino[3,4-b]indole-2(1H)-carboxamide

TLC: Rf 0.23 (hexane:ethyl acetate=2:1);

NMR(DMSO-$d_6$): δ 1.89 (m, 2H), 2.20 (s, 3H), 2.85 (m, 2H), 3.83 (m, 2H), 4.69 (s, 2H), 6.72 (d, J=7.32 Hz, 1H), 6.99 (m, 3H), 7.24 (m, 3H), 7.39 (d, J=7.32 Hz, 1H), 8.29 (s, 1H), 10.90 (s, 1H).

Example 6(2)

N-phenyl-3,4,5,10-tetrahydroazepino[3,4-b]indole-2(1H)-carboxamide

HPLC retention time: 3.73 min.; Mass (ESI, Pos. 20V):m/z 306 (M+H)$^+$.

Example 6(3)

N-butyl-3,4,5,10-tetrahydroazepino[3,4-b]indole-2(1H)-carboxamide

HPLC retention time: 3.69 min.; Mass (ESI, Pos. 20V):m/z 286 (M+H)$^+$.

Example 6(4)

N-(4-chlorophenyl)-3,4,5,10-tetrahydroazepino[3,4-b]indole-2(1H)-carboxamide

HPLC retention time: 3.89 min.; Mass (ESI, Pos. 20V):m/z 340 (M+H)$^+$.

Example 6(5)

N-(3-chlorophenyl)-3,4,5,10-tetrahydroazepino[3,4-b]indole-2(1H)-carboxamide

HPLC retention time: 3.91 min.; Mass (ESI, Pos. 20V):m/z 342, 340 (M+H)$^+$.

Example 6(6)

N-cyclohexyl-3,4,5,10-tetrahydroazepino[3,4-b]indole-2(1H)-carboxamide

HPLC retention time: 3.82 min.; Mass (ESI, Pos. 20V):m/z 312 (M+H)$^+$.

Example 6(7)

N-(2-chlorophenyl)-3,4,5,10-tetrahydroazepino[3,4-b]indole-2(1H)-carboxamide

HPLC retention time: 3.89 min.; Mass (ESI, Pos. 20V):m/z 342, 340 (M+H)$^+$.

Example 6(8)

N-(3,4-dichlorophenyl)-3,4,5,10-tetrahydroazepino[3,4-b]indole-2(1H)-carboxamide HPLC retention time: 4.04 min.; Mass (ESI, Pos. 20V):m/z 376, 374 (M+H)$^+$.

Example 6(9)

N-[3-(trifluoromethyl)phenyl]-3,4,5,10-tetrahydroazepino[3,4-b]indole-2(1H)-carboxamide HPLC retention time: 3.99 min.; Mass (ESI, Pos. 20V):m/z 374 (M+H)$^+$.

Example 6(10)

N-(2-methoxyphenyl)-3,4,5,10-tetrahydroazepino[3,4-b]indole-2(1H)-carboxamide

HPLC retention time: 3.82 min.; Mass (ESI, Pos. 20V):m/z 336 (M+H)$^+$.

Example 6(11)

N-hexyl-3,4,5,10-tetrahydroazepino[3,4-b]indole-2(1H)-carboxamide

HPLC retention time: 3.95 min.; Mass (ESI, Pos. 20V):m/z 314 (M+H)$^+$.

Example 6(12)

N-(3-methoxyphenyl)-3,4,5,10-tetrahydroazepino[3,4-b]indole-2(1H)-carboxamide

HPLC retention time: 3.75 min.; Mass (ESI, Pos. 20V):m/z 336 (M+H)$^+$.

Example 6(13)

N-(4-methoxyphenyl)-3,4,5,10-tetrahydroazepino[3,4-b]indole-2(1H)-carboxamide

HPLC retention time: 3.71 min.; Mass (ESI, Pos. 20V):m/z 336 (M+H)$^+$.

Example 6(14)

N-[2-(trifluoromethyl)phenyl]-3,4,5,10-tetrahydroazepino[3,4-b]indole-2(1H)-carboxamide HPLC retention time: 3.88 min.; Mass (ESI, Pos. 20V):m/z 374 (M+H)$^+$.

Example 6(15)

N-(2,4-dichlorophenyl)-3,4,5,10-tetrahydroazepino[3,4-b]indole-2(1H)-carboxamide HPLC retention time: 4.08 min.; Mass (ESI, Pos. 20V):m/z 376, 374 (M+H)$^+$.

Example 6(16)

ethyl [(3,4,5,10-tetrahydroazepino[3,4-b]indol-2(1H)-ylcarbonyl)amino]acetate

HPLC retention time: 3.49 min.; Mass (ESI, Pos. 20V):m/z 316 (M+H)$^+$.

Example 6(17)

N-(2-fluorophenyl)-3,4,5,10-tetrahydroazepino[3,4-b]indole-2(1H)-carboxamide

HPLC retention time: 3.77 min.; Mass (ESI, Pos. 20V):m/z 324 (M+H)$^+$.

Example 6(18)

N-(3-fluorophenyl)-3,4,5,10-tetrahydroazepino[3,4-b]indole-2(1H)-carboxamide

HPLC retention time: 3.82 min.; Mass (ESI, Pos. 20V):m/z 324 (M+H)$^+$.

Example 6(19)

N-(4-fluorophenyl)-3,4,5,10-tetrahydroazepino[3,4-b]indole-2(1H)-carboxamide

HPLC retention time: 3.77 min.; Mass (ESI, Pos. 20V):m/z 324 (M+H)$^+$.

Example 6(20)

N-[4-(trifluoromethyl)phenyl]-3,4,5,10-tetrahydroazepino[3,4-b]indole-2(1H)-carboxamide HPLC retention time: 3.99 min.; Mass (ESI, Pos. 20V):m/z 374 (M+H)$^+$.

Example 6(21)

N-(3,5-dichlorophenyl)-3,4,5,10-tetrahydroazepino[3,4-b]indole-2(1H)-carboxamide HPLC retention time: 4.13 min.; Mass (ESI, Pos. 20V):m/z 376, 374 (M+H)$^+$.

Example 6(22)

N-(2,5-dichlorophenyl)-3,4,5,10-tetrahydroazepino[3,4-b]indole-2(1H)-carboxamide HPLC retention time: 4.10 min.; Mass (ESI, Pos. 20V): m/z 376, 374 (M+H)$^+$.

Example 6(23)

N-pentyl-3,4,5,10-tetrahydroazepino[3,4-b]indole-2(1H)-carboxamide

HPLC retention time: 3.82 min.; Mass (ESI, Pos. 20V):m/z 300 (M+H)$^+$.

Example 6(24)

N-(2-phenylethyl)-3,4,5,10-tetrahydroazepino[3,4-b]indole-2(1H)-carboxamide

HPLC retention time: 3.80 min.; Mass (ESI, Pos. 20V):m/z 334 (M+H)$^+$.

Example 6(25)

N-(2,3-dichlorophenyl)-3,4,5,10-tetrahydroazepino[3,4-b]indole-2(1H)-carboxamide HPLC retention time: 4.06 min.; Mass (ESI, Pos. 20V):m/z 376, 374 (M+H)$^+$.

Example 6(26)

N-(3-cyanophenyl)-3,4,5,10-tetrahydroazepino[3,4-b]indole-2(1H)-carboxamide

HPLC retention time: 3.75 min.; Mass (ESI, Pos. 20V):m/z 331 (M+H)$^+$.

Example 6(27)

ethyl 4-[(3,4,5,10-tetrahydroazepino[3,4-b]indol-2(1H)-ylcarbonyl)amino]benzoate HPLC retention time: 3.89 min.; Mass (ESI, Pos. 20V):m/z 378 (M+H)$^+$.

Example 6(28)

N-(4-phenoxyphenyl)-3,4,5,10-tetrahydroazepino[3,4-b]indole-2(1H)-carboxamide

HPLC retention time: 4.04 min.; Mass (ESI, Pos. 20V):m/z 398 (M+H)$^+$.

Example 6(29)

ethyl 3-[(3,4,5,10-tetrahydroazepino[3,4-b]indol-2(1H)-ylcarbonyl)amino]benzoate HPLC retention time: 3.86 min.; Mass (ESI, Pos. 20V):m/z 755 (2M+H)$^+$, 378 (M+H)$^+$.

Example 6(30)

N-isopropyl-3,4,5,10-tetrahydroazepino[3,4-b]indole-2(1H)-carboxamide

HPLC retention time: 3.58 min.; Mass (ESI, Pos. 20V):m/z 272 (M+H)$^+$.

Example 6(31)

N-(4-cyanophenyl)-3,4,5,10-tetrahydroazepino[3,4-b]indole-2(1H)-carboxamide

HPLC retention time: 3.73 min.; Mass (ESI, Pos. 20V):m/z 331 (M+H)$^+$.

Example 6(32)

N-(3,5-difluorophenyl)-3,4,5,10-tetrahydroazepino[3,4-b]indole-2(1H)-carboxamide HPLC retention time: 3.91 min.; Mass (ESI, Pos. 20V):m/z 342 (M+H)$^+$.

Example 6(33)

N-[3-fluoro-5-(trifluoromethyl)phenyl]-3,4,5,10-tetrahydroazepino[3,4-b]indole-2(1H)-carboxamide HPLC retention time: 4.08 min.; Mass (ESI, Pos. 20V):m/z 392 (M+H)$^+$.

Example 6(34)

N-(3-chloro-5-fluorophenyl)-3,4,5,10-tetrahydroazepino[3,4-b]indole-2(1H)-carboxamide HPLC retention time: 3.99 min.; Mass (ESI, Pos. 20V):m/z 360, 358 (M+H)$^+$.

Example 6(35)

N-[3-(cyclopentyloxy)phenyl]-3,4,5,10-tetrahydroazepino[3,4-b]indole-2(1H)-carboxamide HPLC retention time: 4.08 min.; Mass (ESI, Pos. 20V):m/z 390 (M+H)$^+$.

Example 6(36)

N-[3-(cyclohexyloxy)phenyl]-3,4,5,10-tetrahydroazepino[3,4-b]indole-2(1H)-carboxamide HPLC retention time: 4.17 min.; Mass (ESI, Pos. 20V):m/z 404 (M+H)$^+$.

Example 6(37)

N-phenyl-1-(trifluoromethyl)-3,4,5,10-tetrahydroazepino[3,4-b]indole-2(1H)-caboxamide HPLC retention time: 3.99 min.; Mass (ESI, Pos. 20V):m/z 374 (M+H)$^+$, 354.

Example 6(38)

N-butyl-1-(trifluoromethyl)-3,4,5,10-tetrahydroazepino[3,4-b]indole-2(1H)-carboxamide HPLC retention time: 3.95 min.; Mass (ESI, Pos. 20V):m/z 354 (M+H)$^+$, 334.

Example 6(39)

N-(4-chlorophenyl)-1-(trifluoromethyl)-3,4,5,10-tetrahydroazepino[3,4-b]indole-2(1H)-carboxamide HPLC retention time: 4.13 min.; Mass (ESI, Pos. 20V):m/z 408 (M+H)$^+$, 388.

Example 6(40)

N-(3-chlorophenyl)-1-(trifluoromethyl)-3,4,5,10-tetrahydroazepino[3,4-b]indole-2(1H)-carboxamide HPLC retention time: 4.13 min.; Mass (ESI, Pos. 20V):m/z 408 (M+H)$^+$, 388.

Example 6(41)

N-cyclohexyl-1-(trifluoromethyl)-3,4,5,10-tetrahydroazepino[3,4-b]indole-2(1H)-carboxamide HPLC retention time: 4.10 min.; Mass (ESI, Pos. 20V):m/z 380 (M+H)$^+$, 360.

Example 6(42)

N-(2-chlorophenyl)-1-(trifluoromethyl)-3,4,5,10-teterhydroazepino[3,4-b]indole-2(1H)-carboxamide HPLC retention time: 4.10 min.; Mass (ESI, Pos. 20V):m/z 408 (M+H)$^+$, 388.

Example 6(43)

N-(3,4-dichlorophenyl)-1-(trifluoromethyl)-3,4,5,10-tetrahydroazepino[3,4-b]indole-2(1H)-carboxamide HPLC retention time: 4.24 min.; Mass (ESI, Pos. 20V):m/z 442 (M+H)$^+$, 422.

Example 6(44)

N-(2-methoxyphenyl)-1-(trifluoromethyl)-3,4,5,10-tetrahydroazepino[3,4-b]indole-2(1H)-carboxamide HPLC retention time: 4.10 min.; Mass (ESI, Pos. 20V):m/z 404 (M+H)$^+$, 384.

Example 6(45)

N-hexyl-1-(trifluoromethyl)-3,4,5,10-tetrahydroazepino[3,4-b]indole-2(1H)-carboxamide HPLC retention time: 4.19 min.; Mass (ESI, Pos. 20V):m/z 382 (M+H)$^+$, 362.

Example 6(46)

N-(3-methoxyphenyl)-1-(trifluoromethyl)-3,4,5,10-tetrahydroazepino[3,4-b]indole-2(1H)-carboxamide HPLC retention time: 3.97 min.; Mass (ESI, Pos. 20V):m/z 404 (M+H)$^+$.

Example 6(47)

N-(4-methoxyphenyl)-1-(trifluoromethyl)-3,4,5,10-tetrahydroazepino[3,4-b]indole-2(1H)-carboxamide HPLC retention time: 3.93 min.; Mass (ESI, Pos. 20V):m/z 404 (M+H)$^+$, 384.

Example 6(48)

1-(trifluoromethyl)-N-[2-(trifluoromethyl)phenyl]-3,4,5,10-tetrahydroazepino[3,4-b]indole-2(1H)-carboxamide HPLC retention time: 4.06 min.; Mass (ESI, Pos. 20V):m/z 442 (M+H)$^+$, 422.

Example 6(49)

N-(2,4-dichlorophenyl)-1-(trifluoromethyl)-3,4,5,10-tetrahydroazepino[3,4-b]indole-2(1H)-carboxamide HPLC retention time: 4.26 min.; Mass (ESI, Pos. 20V):m/z 442 (M+H)$^+$, 424, 422.

Example 6(50)

ethyl ({[1-(trifluoromethyl)-3,4,5,10-tetrahydroazepino[3,4-b]indol-2(1H)-yl]carbonyl}amino)acetate HPLC retention time: 3.75 min.; Mass (ESI, Pos. 20V):m/z 384 (M+H)$^+$, 364.

Example 6(51)

N-(3-fluorophenyl)-1-(trifluoromethyl)-3,4,5,10-tetrahydroazepino[3,4-b]inodole-2(1H)-carboxamide HPLC retention time: 4.04 min.; Mass (ESI, Pos. 20V):m/z 392 (M+H)$^+$, 372.

Example 6(52)

N-benzyl-1-(trifluoromethyl)-3,4,5,10-tetrahydroazepino[3,4-b]indole-2(1H)-caboxamide HPLC retention time: 3.97 min.; Mass (ESI, Pos. 20V):m/z 388 (M+H)$^+$, 368.

Example 6(53)

N-(4-fluorophenyl)-1-(trifluoromethyl)-3,4,5,10-tetrahydroazepino[3,4-b]indole-2(1H)-carboxamide HPLC retention time: 4.00 min.; Mass (ESI, Pos. 20V):m/z 392 (M+H)$^+$, 372.

Example 6(54)

1-(trifluoromethyl)-N-[4-(trifluoromethyl)phenyl]-3,4,5,10-tetrahydroazepino[3,4-b]indole-2(1H)-carboxamide HPLC retention time: 4.19 min.; Mass (ESI, Pos. 20V):m/z 442 (M+H)$^+$, 422.

Example 6(55)

N-(3,5-dichlorophenyl)-1-(trifluoromethyl)-3,4,5,10-tetrahydroazepino[3,4-b]indole-2(1H)-caboxamide HPLC reteniton time: 4.32 min.; Mass (ESI, Pos. 20V):m/z 442 (M+H)$^+$, 422.

Example 6(56)

N-(2,5-dichlorophenyl)-1-(trifluoromethyl)-3,4,5,10-tetrahydroazepino[3,4-b]inodole-2(1H)-carboxamide HPLC retention time: 4.28 min.; Mass (ESI, Pos. 20V):m/z 442 (M+H)$^+$, 422.

Example 6(57)

N-pentyl-1-(trifluoromethyl)-3,4,5,10-tetrahydroazepino[3,4-b]indole-2(1H)-carboxamide HPLC retenition time: 4.04 min.; Mass (ESI, Pos. 20V): m/z 368 (M+H)$^+$, 348.

Example 6(58)

N-(2,3-dichlorophenyl)-1-(trifluoromethyl)-3,4,5,10-tetrahydroazepino[3,4-b]indole-2(1H)-carboxamide HPLC retention time: 4.26 min.; Mass (ESI, Pos. 20V):m/z 442 (M+H)$^+$, 422.

Example 6(59)

N-(3-cyanophenyl)-1-(trifluoromethyl)-3,4,5,10-tetrahydroazepino[3,4-b]indole-2(1H)-carboxamide HPLC retention time: 3.97 min.; Mass (ESI, Pos. 20V):m/z 399 (M+H)$^+$, 379.

Example 6(60)

ethyl 4-({[1-(trifluroromethyl)-3,4,5,10-tetrahydroazepino[3,4-b]indol-2(1H)-yl]carbonyl}amino)benzoate HPLC retention time: 4.10 min.; Mass (ESI, Pos. 20V):m/z 446 (M+H)$^+$, 426.

Example 6(61)

N-(4-phenoxyphenyl)-1-(trifluoromethyl)-3,4,5,10-tetrahydroazepino[3,4-b]indole-2(1H)-carboxamide HPLC retention time: 4.22 min.; Mass (ESI, Pos. 20V):m/z 466 (M+H)⁺.

Example 6(62)

ethyl 3-({[1-(trifluoromethyl)-3,4,5,10-tetrahydroazepino[3,4-b]indol-2(1H)-yl]carbonyl}amino)benzoate HPLC retention time: 4.10 min.; Mass (ESI, Pos. 20V):m/z 446 (M+H)⁺, 426.

Example 6(63)

N-(4-cyanophenyl)-1-(trifluoromethyl)-3,4,5,10-tetrahydroazepino[3,4-b]indole-2(1H)-carboxamide HPLC retention time: 3.95 min.; Mass (ESI, Pos. 20V):m/z 399 (M+H)⁺, 379.

Example 6(64)

N-(3,5-difluorophenyl)-1-(trifluoromethyl)-3,4,5,10-tetrahydroazepino[3,4-b]indole-2(1H)-carboxamide HPLC retention time: 4.10 min.; Mass (ESI, Pos. 20V):m/z 410 (M+H)⁺, 390.

Example 6(65)

N-(3-chloro-5-fluorophenyl)-1-(trifluoromethyl)-3,4,5,10-tetrahydroazepino[3,4-b]indole-2(1H)-carboxamide HPLC retention time: 4.19 min.; Mass (ESI, Pos. 20V):m/z 426 (M+H)⁺, 406.

Example 6(66)

N-[3-(cyclohexyloxy)phenyl]-1-(trifluoromethyl)-3,4,5,10-tetrahydroazepino[3,4-b]indole-2(1H)-carboxamide HPLC retention time: 4.37 min.; Mass (ESI, Pos. 20V):m/z 943 (2M+H)⁺, 472 (M+H)⁺.

Example 6(67)

6-methoxy-N-(3-methylphenyl)-1-(trifluoromethyl)-1,3,4,9-tetrahydro-2H-β-carboline-2-carboxamide TLC: Rf 0.25 (hexane:ethyl acetate=3:1);
NMR(DMSO-d₆): δ 2.25 (s, 3H), 2.77 (m, 2H), 3.44 (m, 1H), 3.75 (s, 3H), 4.53 (m, 1H), 6.21 (q, J=7.87 Hz, 1H), 6.79 (m, 2H), 6.98 (d, J=2.20 Hz, 1H), 7.14 (t, J=7.69 Hz, 1H), 7.28 (m, 3H), 8.93 (s, 1H), 10.96 (s, 1H).

Example 6(68)

1-(3-fluorophenyl)-N-(3-methylphenyl)-3,4,5,10-tetrahydroazepino[3,4-b]indole-2(1H)-carboxamide TLC: Rf 0.56 (hexane:ethyl acetate=2:1);
NMR(DMSO-d₆): δ 1.85 (m, 2H), 2.24 (s, 3H), 2.68 (m, 1H), 3.01 (m, 2H), 4.10 (m, 1H), 6.78 (m, 3H), 7.08 (m, 5H), 7.30 (m, 3H), 7.40 (m, 1H), 7.49 (d, J=7.51 Hz, 1H), 8.51 (s, 1H), 11.10 (s, 1H).

Example 6(69)

7-methoxy-N-(3-methylphenyl)-1-(trifluoromethyl)-3,4,5,10-tetrahydroazepino[3,4-b]indole-2(1H)-carboxamide TLC: Rf 0.32 (hexane:ethyl acetate=3:1);
NMR(DMSO-d₆): δ 1.72 (m, 1H), 2.05 (m, 1H), 2.24 (s, 3H), 2.73 (m, 1H), 3.04 (m, 1H), 3.53 (m, 1H), 3.75 (s, 3H), 4.40 (m, 1H), 6.55 (q, J=9.40 Hz, 1H), 6.75 (dd, J=8.70, 2.47 Hz, 1H), 6.81 (d, J=7.69 Hz, 1H), 6.99 (d, J=2.38 Hz, 1H), 7.12 (t, J=7.96 Hz, 1H), 7.24 (m, 3H), 8.76 (s, 1H), 11.10 (s, 1H).

Example 7

2-[1-(3-fluorophenyl)-1,3,4,9-tetrahydro-2H-β-carbolin-2-yl]-N-phenylacetamide hydrochloride

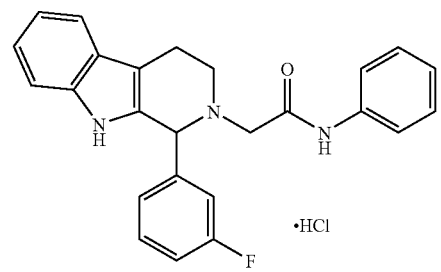

A solution of 1-(3-fluorophenyl)-2,3,4,9-tetrahydro-1H-β-carboline (264 mg) in acetonitrile (3 mL) was added by 2-chloro-N-phenylacetamide iodide (168 mg), potassium carbonate (274 mg) and tetra-n-butylammonium (38 mg) successively and the mixture was refluxed for 3 hours. The reaction mixture was cooled down, added by 1N hydrochloric acid and extracted by ethyl acetate. The organic layer was washed with water, saturated sodium bicarbonate aqueous solution and saturated brine successively, dried over anhydrous magnesium sulfate and then concentrated under reduced pressure. The residue was purified by column chromatography on silica gel to give the free compounds (317 mg) of the title compound having the following physical data. A solution of the obtained free compounds (240 mg) in dioxane (1 mL) was added by 4N hydrochloric acid-dioxane solution (0.15 mL) and was stirred for 10 minutes at the room temperature. The mixture was concentrated and the residue was fixed with isopropylether and benzene to give the hydrochloride (267 mg) having the following physical data.

Free Compounds:
TLC: Rf 0.35 (hexane:ethyl acetate=2:1);
NMR(DMSO-d₆): δ 2.94 (m, 4H), 3.31 (m, 2H), 5.02 (s, 1H), 7.05 (m, 4H), 7.33 (m, 7H), 7.61 (m, 2H), 9.71 (s, 1H), 10.47 (s, 1H).

Hydrochloride:
TLC: Rf 0.35 (hexane:ethyl acetate=2:1);
NMR(CD$_3$OD): δ 3.30 (m, 2H), 3.68 (m, 2H), 4.30 (s, 2H), 6.03 (s, 1H), 7.24 (m, 8H), 7.55 (m, 5H).

Example 8 benzyl 1,3,4,9-tetrahydro-2H-β-carboline-2-carboxylate

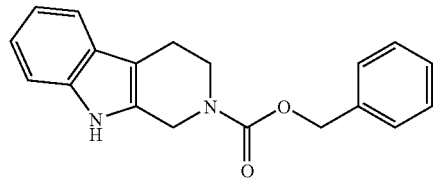

A solution of 2,3,4,9-tetrahydro-1H-β-carboline (999 mg) in tetrahydrofuran (30 mL) was added by triethylamine (0.90 mL) and benzylchloridecarbonate (0.83 mL) successively under the ice and the mixture was stirred for 30 minutes at the room temperature. The reaction mixture was added by 1N hydrochloric acid and extracted by ethyl acetate. The organic layer was washed with water, saturated sodium bicarbonate aqueous solution and saturated brine successively, dried over anhydrous magnesium sulfate and then concentrated under reduced pressure to give the title compounds (1.59 g) having the following physical data.
TLC: Rf 0.42 (hexane:ethyl acetate=2:1);
NMR(CDCl$_3$): δ 2.82 (m, 2H), 3.85 (m, 2H), 4.71 (s, 2H), 5.20 (s, 2H), 7.14 (m, 2H), 7.38 (m, 7H), 7.83 (m, 1H).

Example 9

2-(1-oxo-1,2,3,4-tetrahydro-9H-β-carbolin-9-yl)-N-phenylacetamide

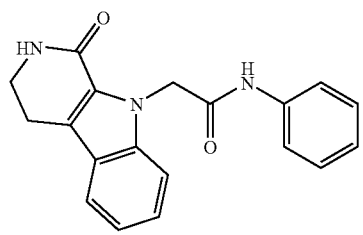

Sodium hydroxide (25 mg, 62.7% in Oil) was dispersed into dimethylformamide (1 mL) and the mixture was added by 2,3,4,9-tetrahydro-1H-β-carbolin-1-one (167 mg) under the ice and stirred for 10 minutes at 0° C. The reaction mixture was added by water and the deposit was filtrated. The filtrate was dissolved by ethyl acetate, washed with water and saturated brine successively, dried over anhydrous magnesium sulfate and then concentrated under reduced pressure. The residue was washed (ethyl acetate, 6 mL) to give the title compounds (149 mg) having the following physical data.
TLC: Rf 0.24 (hexane:ethyl acetate=1:1);
NMR(DMSO-d$_6$): δ 2.95 (t, J=6.87 Hz, 2H), 3.49 (m, 2H), 5.45 (s, 2H), 7.02 (t, J=7.41 Hz, 1H), 7.13 (m, 1H), 7.29 (m, 3H), 7.54 (m, 3H), 7.64 (m, 2H), 10.30 (s, 1H).

Example 10 tert-butyl 3-(cyanomethyl)-1H-indole-1-carboxylate

A solution of 1H-indol-3-ylacetonitrile (8.0 g) in acetonitrile (150 mL) was added by di-tert-butyl dicarbonate (13.5 g) and dimethylaminopyridine (938 mg) successively and stirred at the room temperature. The reaction mixture was concentrated and the obtained residue was purified by column chromatography on silica gel (hexane:ethyl acetate=from 10:1 to 5:1) to give the title compounds (10.5 mg) having the following physical data.
TLC: Rf 0.36 (hexane:ethyl acetate=5:1);
NMR(CDCl$_3$): δ 1.68 (s, 9H), 3.78 (d, J=1.28 Hz, 2H), 7.26-7.33 (m, 1H), 7.34-7.44 (m, 1H), 7.49-7.57 (m, 1H), 7.64 (s, 1H), 8.17 (d, J=8.06 Hz, 1H).

Example 11

1-(1H-indol-3-yl)cyclopropanecarbonitrile

A suspension of potassium hydroxide (3.37 g) in dimethylsulfoxide (80 mL) was dropped by the compounds prepared in Example 10 (5.12 g) and a solution of 1,2-dibromoethane (1.74 mL) in tert-butylmethylether (20 mL) at the room temperature and the mixture was stirred for 2 hours. The reaction mixture was diluted with tert-butylmethylether and poured into water. The aqueous layer was neutralized by 2N hydrochloric acid and extracted by ethyl acetate. The organic layer was washed with saturated brine, dried over anhydrous sodium sulfate and then concentrated. The residue was purified by column chromatography on silica gel (hexane:ethyl acetate=5:1) to give the mixed compound (1.5 g) of the title compounds and 1H-indol-3-ylacetonitrile. This compound was dissolved into acetonitrile (30 mL), added by di-tert-butyl dicarbonate (2.62 g) and dimethylaminopyridine (122 mg) at the room temperature and stirred overnight. The reaction mixture was added by water and extracted by ethyl acetate. The organic layer was washed with water, dried over anhydrous sodium sulfate and then concentrated. The residue was purified by column chromatography on silica gel (hexane:ethyl acetate=from 20:1 to 10:1) to give tert-butyl 3-(1-cyanocyclopropyl)-1H-indole-1-carboxylate (524 mg). The obtained compounds were dissolved into dichloromethane (3 mL) solution, added by trifluoroacetic acid (4.26 mL) at the room temperature and stirred for 2 hours. The reaction mixture was concentrated. The obtained residue was dissolved into dichloromethane, washed with 1N sodium hydroxide aqueous solution, dried over anhydrous sodium sulfate and concentrated to give the title compounds (320 mg) having the following physical data.
TLC: Rf 0.34 (hexane:ethyl acetate=2:1);
NMR(CDCl$_3$): δ 1.34-1.41 (m, 2H), 1.63-1.70 (m, 2H), 7.12 (d, J=2.75 Hz, 1H), 7.17-7.29 (m, 2H), 7.35-7.41 (m, 1H), 7.80-7.87 (m, 1H), 8.08 (s, 1H).

Example 12 tert-butyl 3-(1-cyano-1-methylethyl)-1H-indole-1-carboxylate

A mixed solution of the compounds prepared in Example 10 (512 mg) and methyl iodide (260 μL) in anhydrous dimethylformamide (5 mL) and anhydrous tetrahydrofuran (0.5 mL) was gradually added by sodium hydroxide (168 mg) under the ice and stirred overnight at the room temperature. The reaction mixture was added by saturated ammonium chloride aqueous solution and extracted by ethyl acetate. The organic layer was washed with water and saturated brine successively, dried over anhydrous sodium hydroxide and then concentrated. The residue was purified by column chromatography on silica gel (hexane ethyl acetate=10:1) to give the title compounds (380 mg) having the following physical data.

TLC: Rf 0.50 (hexane:ethyl acetate=5:1);

NMR(CDCl$_3$): δ 1.68 (s, 9H), 1.85 (s, 6H), 7.27-7.34 (m, 1H), 7.34-7.41 (m, 1H), 7.52 (s, 1H), 7.78-7.85 (m, 1H), 8.17 (d, J=8.42 Hz, 1H).

Example 13

2-(1H-indol-3-yl)-2-methylpropanenitrile

A solution of the compounds prepared in Example 12 (3.8 g) in dichloromethane (30 mL) was added by trifluoroacetic acid (26.2 mL) and stirred for 2 hours. The reaction mixture was concentrated. The obtained residue was dissolved into dichloromethane, washed with 1N sodium hydroxide aqueous solution, dried over anhydrous magnesium sulfate and then concentrated to give the title compounds (2.7 g) having the following physical data. The obtained compounds were used in the next reaction without purification.

TLC: Rf 0.17 (hexane:ethyl acetate=5:1);

NMR(CDCl$_3$): δ 1.86 (s, 6H), 7.10-7.29 (m, 3H), 7.35-7.43 (m, 1H), 7.80-7.87 (m, J=8.42 Hz, 1H), 8.10 (s, 1H).

Example 14

{[1-(1H-indol-3-yl)cyclopropyl]methyl}amine

A suspension of lithium aluminum hydride (217 mg) in anhydrous tetrahydrofuran (2 mL) was heated to the temperature of 50° C. and then the mixture was dropped by a solution of the compounds prepared in Example 11 (260 mg) in anhydrous tetrahydrofuran (3 mL) and stirred at the temperature of 80° C. Under the ice, the reaction mixture was added by ice and 1N hydrochloric acid to be acidic and then filtrated by celite (trade name). The filtrate was added by 2N sodium hydroxide aqueous solution to be basic and then filtrated by celite. The filtrate was extracted by dichloromethane. The organic layer was dried over anhydrous sodium sulfate and then concentrated to give the title compounds (280 mg) having the following physical data. The obtained compounds were used in the next reaction without purification.

TLC: Rf 0.33 (dichloromethane:methanol:28% ammonia water=9:1:0.1);

NMR(CDCl$_3$): δ 0.70-0.79 (m, 2H), 0.79-0.88 (m, 2H), 2.81 (s, 2H), 7.08 (d, J=2.38 Hz, 1H), 7.10-7.17 (m, 1H), 7.17-7.24 (m, 1H), 7.37 (d, J=8.06 Hz, 1H), 7.76 (d, J=7.69 Hz, 1H), 8.07 (s, 1H).

Example 14(1)

[2-(1H-indol-3-yl)-2-methylpropyl]amine

By the same procedure as described in Example 14 using the compounds prepared in Example 13 instead of the compounds prepared in Example 11, the title compounds having the following physical data ware obtained.

TLC: Rf 0.46 (dichloromethane:methanol:28% ammonia water=9:1:0.1);

NMR(CDCl$_3$): δ 1.41 (s, 6H), 3.00 (s, 2H), 6.97 (d, J=2.56 Hz, 1H), 7.03-7.12 (m, 1H), 7.13-7.22 (m, 1H), 7.33-7.40 (m, 1H), 7.77 (d, J=7.87 Hz, 1H), 8.10 (s, 1H).

Example 15

1-(3-fluorophenyl)-1,2,3,9-tetrahydrospiro[β-carboline-4,1'-cyclopropane]

A solution of the compounds prepared in Example 14 (280 mg) in acetic acid (5 mL) was added by 3-fluorobenzaldehyde (167 μL) and stirred at the temperature of 100° C. After the reaction, acetic acid was diluted away and the residue was dissolved into dichloromethane, washed away 1N sodium hydroxide aqueous solution, dried over anhydrous sodium sulfate and then concentrated. The residue was washed with mixed solvents (hexane:ethyl acetate=1:2) to give the title compounds (238 mg) having the following physical data.

TLC: Rf 0.40 (ethyl acetate);

NMR(CDCl$_3$): δ 0.71-0.81 (m, 1H), 0.81-0.92 (m, 1H), 1.38-1.52 (m, 1H), 1.52-1.65 (m, 1H), 2.82 (d, J=13.36 Hz, 1H), 3.12 (d, J=13.36 Hz, 1H), 5.23 (s, 1H), 6.96-7.18 (m, 5H), 7.20-7.28 (m, 1H), 7.28-7.40 (m, 2H), 7.52 (s, 1H).

Example 15(1)-Example 15(6)

By the same procedure as described in Example 15 using the corresponding amine derivatives instead of the compounds prepared in Example 14 and 3-fluorobenzaldehyde or the corresponding instead thereof, the following title compounds were obtained.

Example 15(1)

1-(3-fluorophenyl)-4,4-dimethyl-2,3,4,9-tetrahydro-1H-β-carboline

TLC: Rf 0.69 (dichloromethane:methanol:28% ammonia water=9:1:0.1);

NMR(CDCl$_3$): δ 1.47 (s, 3H), 1.52 (s, 3H), 2.89 (d, J=12.81 Hz, 1H), 2.94 (d, J=12.81 Hz, 1H), 5.11 (s, 1H), 6.96-7.16 (m, 5H), 7.18-7.41 (m, 3H), 7.64-7.76 (m, 1H).

Example 15(2)

1-(3-fluorophenyl)-6-methoxy-1-methyl-2,3,4,9-tetrahydro-1H-β-carboline

TLC: Rf 0.58 (ethyl acetate);

NMR(CDCl$_3$): δ 1.79 (s, 3H), 2.61-2.95 (m, 3H), 3.09-3.20 (m, 1H), 3.87 (s, 3H), 6.85 (dd, J=8.70, 2.47 Hz, 1H), 6.88-6.97 (m, 1H), 6.97-7.10 (m, 3H), 7.16-7.30 (m, 2H), 7.69 (s, 1H).

Example 15(3)

1-(3-fluorophenyl)-1-methyl-2,3,4,9-tetrahydro-1H-β-carboline

TLC: Rf 0.59 (ethyl acetate);

NMR(DMSO-d$_6$): δ 1.67 (s, 3H), 2.33-2.82 (m, 3H), 2.94-3.07 (m, 1H), 6.91-7.16 (m, 5H), 7.23-7.35 (m, 2H), 7.39 (d, J=7.32 Hz, 1H), 10.96 (s, 1H).

Example 15(4)

1-[3-(trimethylsilyl)phenyl]-2,3,4,9-tetrahydro-1H-β-carboline

TLC: Rf 0.27 (dichloromethane:methanol:ammonia water=9:1:0.1);
NMR(CDCl$_3$): δ 0.27 (s, 9H) 2.76-2.88 (m, 1H) 2.88-3.03 (m, 1H) 3.10-3.24 (m, 1H) 3.36-3.48 (m, 1H) 5.18 (t, J=1.83 Hz, 1H) 7.07-7.18 (m, 2H) 7.19-7.25 (m, 2H) 7.32 (t, J=7.51 Hz, 1H) 7.44-7.59 (m, 4H).

Example 15(5)

rac-(1R,3S)-1-(3-fluorophenyl)-3-methyl-2,3,4,9-tetrahydro-1H-β-carboline (cis-isomer)

TLC: Rf 0.42 (dichloromethane: methanol=19:1);
NMR(CDCl$_3$): δ 1.36 (d, J=6.41 Hz, 3H), 2.50-2.63 (m, 1H), 2.82-2.93 (m, 1H), 3.22-3.37 (m, 1H), 5.20-5.26 (m, 1H), 6.99-7.25 (m, 6H), 7.29-7.42 (m, 2H), 7.49-7.55 (m, 1H).

Example 15(6)

rac-(1R,3R)-1-(3-fluorophenyl)-3-methyl-2,3,4,9-tetrahydro-1H-β-carboline (trans-isomer)

TLC: Rf 0.27 (dichloromethane:methanol=9:1);
NMR(CDCl$_3$): δ 1.23 (d, J=6.41 Hz, 3H) 2.44-2.57 (m, 1H) 2.94 (dd, J=15.56, 4.21 Hz, 1H) 3.14-3.35 (m, 1H) 5.22 (s, 1H) 6.87-7.06 (m, 3H) 7.08-7.22 (m, 2H) 7.23-7.35 (m, 2H) 7.55 (dd, J=7.78, 1.19 Hz, 1H) 7.64 (s, 1H).

In addition, the compounds in Example 15(5) and Example 15(6) were prepared by separating diastereomer mixture which was obtained by reacting [2-(1H-indol-3-yl)-1-methylethyl]amine with 3-fluorobenzaldehyde, by column chromatography on silica gel.

Example 16-Example 16(23)

By the same procedure as described in Example 1 using the corresponding amine derivatives instead of 2,3,4,9-tetrahydro-1H-β-carboline and the corresponding isocyanate derivatives instead of 1-isocynato-3-(trifluoromethyl)benzene, the following compounds in the present invention were obtained.

Example 16

N-(3,5-dimethylphenyl)-1-(3-fluorophenyl)-1,9-dihydrospiro[β-carboline-4,1'-cyclopropane]-2(3H)-carboxamide TLC: Rf 0.41 (hexane:ethyl acetate=3:1);
NMR(DMSO-d$_6$): δ 0.69-0.81 (m, 1H), 1.00-1.28 (m, 2H), 1.53-1.66 (m, 1H), 2.21 (s, 6H), 3.41 (d, J=14.82 Hz, 1H), 3.64 (d, J=14.82 Hz, 1H), 6.60 (s, 1H), 6.76 (s, 1H), 6.88-6.96 (m, 1H), 6.97-7.20 (m, 6H), 7.24 (d, J=7.87 Hz, 1H), 7.31 (d, J=8.05 Hz, 1H), 7.37-7.47 (m, 1H), 8.48 (s, 1H), 11.10 (s, 1H).

Example 16(1)

N-(2-chlorophenyl)-7-methoxy-1-(trifluoromethyl)-3,4,5,10-tetrahydroazepino[3,4-b]inodole-2(1)-carboxamide TLC: Rf 0.34 (hexane:ethyl acetate=4:1);
NMR(DMSO-d$_6$): δ 1.87 (m, 1H), 2.07 (m, 1H), 2.75 (m, 1H), 3.08 (m, 1H), 3.56 (m, 1H), 3.75 (s, 3H), 4.38 (m, 1H), 6.52 (q, J=9.34 Hz, 1H), 6.75 (dd, J=8.70, 2.11 Hz, 1H), 7.00 (d, J=2.38 Hz, 1H), 7.20 (m, 2H), 7.30 (m, 1H), 7.40 (m, 1H), 7.47 (dd, J=7.87, 1.46 Hz, 1H), 8.68 (s, 1H), 11.07 (s, 1H).

Example 16(2)

7-methoxy-N-(2-methoxyphenyl)-1-(trifluoromethyl)-3,4,5,10-tetrahydroazepino[3,4-b]indole-2(1H)-carboxamide TLC: Rf 0.44 (hexane:ethyl acetate=2:1);
NMR(DMSO-d$_6$): δ 1.82 (m, 1H), 2.07 (m, 1H), 2.74 (m, 1H), 3.06 (m, 1H), 3.56 (m, 1H), 3.75 (s, 3H), 3.77 (s, 3H), 4.31 (m, 1H), 6.53 (m, 1H), 6.75 (dd, J=8.79, 2.38 Hz, 1H), 6.87 (m, 1H), 7.01 (m, 2H), 7.09 (m, 1H), 7.21 (d, J=8.79 Hz, 1H), 7.44 (dd, J=7.87, 1.46 Hz, 1H), 8.06 (s, 1H), 11.06 (s, 1H).

Example 16(3)

N-(2-fluorophenyl)-7-methoxy-1-(trifluoromethyl)-3,4,5,10-tetrahydroazepino[3,4-b]indole-2(1H)-carboxamide TLC: Rf 0.24 (hexane:ethyl acetate=4:1);
NMR(DMSO-d$_6$): δ 1.81 (m, 1H), 2.07 (m, 1H), 2.73 (m, 1H), 3.07 (m, 1H), 3.56 (m, 1H), 3.76 (s, 3H), 4.36 (m, 1H), 6.51 (q, J=9.09 Hz, 1H), 6.75 (dd, J=8.79, 2.38 Hz, 1H), 7.00 (d, J=2.38 Hz, 1H), 7.15 (m, 4H), 7.32 (m, 1H), 8.72 (s, 1H), 11.08 (s, 1H).

Example 16(4)

N-phenyl-3,4,5,6-tetrahydroazepino[4,3-b]indole-2(1H)-carboxamide

TLC: Rf 0.26 (hexane:ethyl acetate=1:1);
NMR(DMSO-d$_6$): δ 1.88 (m, 2H), 2.94 (m, 2H), 3.79 (m, 2H), 4.73 (s, 2H), 6.86 (m, 1H), 6.95 (m, 2H), 7.18 (m, 3H), 7.39 (m, 2H), 7.59 (m, 1H), 8.33 (s, 1H), 10.86 (s, 1H).

Example 16(5)

N-(2-chlorophenyl)-3,4,5,6-tetrahydroazpino[4,3-b]indole-2(1H)-carboxamide

TLC: Rf 0.45 (hexane:ethyl acetate=1:1);
NMR(DMSO-d$_6$): δ 1.95 (m, 2H), 2.95 (m, 2H), 3.82 (m, 2H), 4.71 (s, 2H), 6.98 (m, 3H), 7.22 (m, 2H), 7.35 (dd, J=8.06, 1.46 Hz, if), 7.53 (d, J=7.14 Hz, 1H), 7.64 (dd, J=8.06, 1.46 Hz, 1H), 7.74 (s, 1H), 10.89 (s, 1H).

Example 16(6)

N-(2-fluorophenyl)-3,4,5,6-tetrahydroazepino[4,3-b]indole-2(1H)-carboxamide

TLC: Rf 0.46 (hexane:ethyl acetate=1:1);
NMR(DMSO-$d_6$): δ 1.90 (m, 2H), 2.95 (m, 2H), 3.79 (m, 2H), 4.71 (s, 2H), 7.03 (m, 5H), 7.23 (m, 1H), 7.49 (m, 2H), 7.98 (s, 1H), 10.87 (s, 1H).

Example 16(7)

N-(3-methylphenyl)-3,4,5,6-tetrahydroazepino[4,3-b]indole-2(1H)-carboxamide

TLC: Rf 0.36 (hexane:ethyl acetate=1:1);
NMR(DMSO-$d_6$): δ 1.87 (m, 2H), 2.18 (s, 3H), 2.94 (m, 2H), 3.78 (m, 2H), 4.72 (s, 2H), 6.68 (d, J=7.51 Hz, 1H), 6.97 (m, 3H), 7.21 (m, 3H), 7.58 (m, 1H), 8.25 (s, 1H), 10.86 (s, 1H).

Example 16(8)

7-methoxy-N-phenyl-3,4,5,10-tetrahydroazpino[3,4-b]indole-2(1H)-carboxamide

TLC: Rf 0.15 (hexane:ethyl acetate=2:1);
NMR(CDCl$_3$): δ 2.07 (m, 2H), 2.93 (m, 2H), 3.78 (m, 2H), 3.84 (s, 3H), 4.71 (s, 2H), 6.53 (s, 1H), 6.74 (dd, J=8.70, 2.38 Hz, 1H), 6.90 (d, J=2.38 Hz, 1H), 7.01 (m, 2H), 7.23 (m, 2H), 7.30 (m, 2H), 8.53 (s, 1H).

Example 16(9)

N-(2-chlorophenyl)-7-methoxy-3,4,5,10-tetrahydroazepino[3,4-b]indole-2(1H)-carboxamide TLC: Rf 0.37 (hexane:ethyl acetate=2:1);
NMR(CDCl$_3$): δ 2.15 (m, 2H), 2.98 (m, 2H), 3.87 (m, 5H), 4.78 (s, 2H), 6.80 (dd, J=8.79, 2.38 Hz, 1H), 6.93 (m, 2H), 7.10 (s, 1H), 7.19 (m, 2H), 7.30 (dd, J=8.06, 1.28 Hz, 1H), 8.00 (s, 1H), 8.14 (dd, J=8.33, 1.56 Hz, 1H).

Example 16(10)

7-methoxy-N-(3-methylphenyl)-3,4,5,10-tetrahydroazepino[3,4-b]indole-2(1H)-carboxamide TLC: Rf 0.24 (hexane:ethyl acetate=2:1);
NMR(CDCl$_3$): δ 2.09 (m, 2H), 2.26 (s, 3H), 2.95 (m, 2H), 3.80 (m, 2H), 3.84 (s, 3H), 4.72 (s, 2H), 6.41 (s, 1H), 6.76 (dd, J=8.79, 2.38 Hz, 1H), 6.83 (d, J=6.96 Hz, 1H), 6.91 (d, J=2.38 Hz, 1H), 7.11 (m, 4H), 8.32 (s, 1H).

Example 16(11)

N-(2-fluorophenyl)-7-methoxy-3,4,5,10-tetrahydroazepino[3,4-b]indole-2(1H)-carboxamide TLC: Rf 0.24 (hexane:ethyl acetate=2:1);
NMR(CDCl$_3$): δ 2.11 (m, 2H), 2.97 (m, 2H), 3.84 (m, 5H), 4.76 (s, 2H), 6.67 (d, J=3.66 Hz, 1H), 6.79 (dd, J=8.79, 2.38 Hz, 1H), 7.00 (m, 4H), 7.16 (d, J=8.79 Hz, 1H), 8.04 (m, 2H).

Example 16(12)

N-(3,5-dichlorophenyl)-7-methoxy-3,4,5,10-tetrahydroazpino[3,4-b]indole-2(1H)-carboxamide TLC: Rf 0.39 (hexane:ethyl acetate=2:1);
NMR(CDCl$_3$): δ 2.07 (m, 2H), 2.94 (m, 2H), 3.78 (m, 2H), 3.84 (s, 3H), 4.69 (s, 2H), 6.53 (s, 1H), 6.79 (dd, J=8.78, 2.56 Hz, 1H), 6.91 (d, J=2.56 Hz, 1H), 6.97 (t, J=1.83 Hz, 1H), 7.13 (d, J=8.78 Hz, 1H), 7.25 (d, J=1.83 Hz, 2H), 8.19 (s, 1H).

Example 16(13)

N-(3,5-dimethylphenyl)-1-(3-fluorophenyl)-6-methoxy-1-methyl-1,3,4,9-tetrahydro-2H-β-carboline-2-carboxamide TLC: Rf 0.52 (hexane:ethyl acetate=3:1);
NMR(DMSO-$d_6$): δ 2.12 (s, 3H), 2.16 (s, 6H), 2.82 (m, 1H), 3.08 (m, 1H), 3.49 (m, 1H), 3.74 (s, 3H), 4.22 (m, 1H), 6.52 (s, 1H), 6.63 (dd, J=8.79, 2.38 Hz, 1H), 6.91 (m, 4H), 7.05 (d, J=8.79 Hz, 1H), 7.18 (m, 3H), 8.58 (s, if), 10.24 (s, 1H).

Example 16(14)

N-(3,5-dimethylphenyl)-1-(3-fluorophenyl)-1-methyl-1,3,4,9-tetrahydro-2H-β-carboline-2-carboxamide TLC: Rf 0.64 (hexane:ethyl acetate=3:1);
NMR(DMSO-$d_6$): δ 2.14 (s, 3H), 2.16 (s, 6H), 2.84 (m, 1H), 3.13 (m, 1H), 3.50 (m, 1H), 4.23 (m, 1H), 6.52 (s, 1H), 6.98 (m, 5H), 7.19 (m, 4H), 7.45 (d, J=7.32 Hz, 1H), 8.59 (s, 1H), 10.42 (s, 1H).

Example 16(15)

1-(3-fluorophenyl)-N-[3-(trimethylsilyl)phenyl]-1,3,4,9-tetrahydro-2H-β-carboline-2-carboxamide TLC: Rf 0.38 (hexane:ethyl acetate=3:1);
NMR(DMSO-$d_6$): δ 0.22 (s, 9H), 2.85 (m, 1H), 3.16 (m, 1H), 4.32 (dd, J=14.46, 4.21 Hz, 1H), 6.68 (s, 1H), 7.08 (m, 6H), 7.24 (m, 1H), 7.32 (m, 1H), 7.40 (m, 1H), 7.48 (d, J=7.87 Hz, 1H), 7.54 (m, 2H), 8.71 (s, 1H), 11.01 (s, 1H).

Example 16(16)

N-(3,5-dimethylphenyl)-1-[3-(trimethylsilyl)phenyl]-1,3,4,9-tetrahydro-2H-β-carboline-2-carboxamide TLC: Rf 0.31 (ethyl acetate:hexane=1:5);
NMR(CDCl$_3$): δ 0.26 (s, 9H), 2.27 (s, 6H), 2.92 (m, 1H), 3.04 (m, 1H), 3.50 (m, 1H), 4.12 (m, 1H), 6.40 (s, 1H), 6.57 (s, 1H), 6.68 (s, 1H), 6.95 (s, 2H), 7-16 (m, 2H), 7.30 (m, 3H), 7.50 (m, 1H), 7.55 (dd, J=7.69, 1.28 Hz, 1H), 7.64 (s, 1H), 7.71 (s, 1H).

Example 16(17)

rac-(1R,3S)—N-(3,5-dimethylphenyl)-1-(3-fluorophenyl)-3-methyl-1,3,4,9-tetrahydro-2H-β-carboline-2-carboxamide TLC: Rf 0.38 (ethyl acetate:hexane=1:4);
NMR(CDCl$_3$): δ 1.28 (d, J=6.96 Hz, 3H), 2.27 (s, 6H), 2.84 (m, 1H), 3.16 (m, 1H), 4.82 (m, 1H), 6.30 (s, 1H), 6.54 (d, J=1.46 Hz, 1H), 6.69 (s, 1H), 6.93 (s, 2H), 7.03 (m, 1H), 7.18 (m, 3H), 7.33 (m, 3H), 7.53 (m, 1H), 7.73 (s, 1H).

Example 16(18)

rac-(1R,3R)—N-(3,5-dimethylphenyl)-1-(3-fluorophenyl)-3-methyl-1,3,4,9-tetrahydro-2H-β-carboline-2-carboxamide TLC: Rf 0.32 (ethyl acetate:hexane=1:4);
NMR(CDCl$_3$): δ 1.25 (d, J=6.59 Hz, 3H), 2.16 (s, 6H), 2.83 (m, 1H), 3.24 (m, 1H), 4.77 (m, 1H), 5.78 (s, 1H), 6.41 (s, 1H), 6.58 (s, 1H), 6.76 (s, 2H), 6.88 (m, 1H), 7.06 (m, 3H), 7.21 (m, 3H), 7.45 (m, 1H), 7.58 (s, 1H).

Example 16(19)

N-(3,5-dimethylphenyl)-1-(3-fluorophenyl)-6-(trimethylsilyl)-1,3,4,9-tetrahydro-2H-β-carboline-2-carboxamide TLC: Rf 0.20 (hexane:ethyl acetate=5:1);
NMR(CDCl$_3$): δ 0.32 (s, 9H), 2.28 (s, 6H), 2.86-2.98 (m, 1H), 2.98-3.13 (m, 1H), 3.37-3.52 (m, 1H), 3.93 (dd, J=14.19, 4.12 Hz, 1H), 6.39 (s, 1H), 6.71 (s, 1H), 6.73 (s, 1H), 6.94-7.04 (m, 3H), 7.04-7.11 (m, 1H), 7.17 (d, J=7.69 Hz, 1H), 7.22-7.40 (m, 3H), 7.71 (d, J=0.73 Hz, 1H), 7.87 (s, 1H).

Example 16(20)

N-(3,5-dimethylphenyl)-1-(3-fluorophenyl)-4,4-dimethyl-1,3,4,9-tetrahydro-2H-β-carboline-2-carboxamide TLC: Rf 0.20 (hexane:ethyl acetate=5:1);
NMR(DMSO-d$_6$): δ 1.30 (s, 3H), 1.46 (s, 3H), 2.21 (s, 6H), 2.89 (d, J=14.46 Hz, 1H), 4.06 (d, J=14.46 Hz, 1H), 6.60 (s, 1H), 6.73 (s, 1H), 6.94-7.22 (m, 7H), 7.26-7.49 (m, 2H), 7.65 (d, J=7.87 Hz, 1H), 8.50 (s, 1H), 10.98 (s, 1H).

Example 16(21)

N-benzyl-1-(3-fluorophenyl)-3,3-dimethyl-1,3,4,9-tetrahydro-2H-β-carboline-2-carboxamide TLC: Rf 0.50 (hexane:ethyl acetate=2:1);
NMR(CDCl$_3$): δ 1.40 (s, 3H), 1.57 (s, 3H), 2.72 (dd, J=15.20, 1.28 Hz, 1H), 2.97 (dd, J=15.20, 1.28 Hz, 1H), 4.08 (dd, J=14.92, 4.76 Hz, 1H), 4.37 (dd, J=14.92, 7.05 Hz, 1H), 5.27-5.38 (m, 1H), 5.58 (s, 1H), 6.79-6.89 (m, 2H), 6.96-7.09 (m, 2H), 7.09-7.15 (m, 1H), 7.15-7.33 (m, 6H), 7.41 (s, 1H), 7.46-7.53 (m, 1H).

Example 16(22)

N-(3,5-dimethylphenyl)-1-(3-fluorophenyl)-1,9-dihydrospiro[β-carboline-4,1'-cyclobutane]-2(3H)-carboxamide TLC: Rf 0.34 (ethyl acetate:hexane=1:4);
NMR(CDCl$_3$): δ 1.92-2.12 (m, 1H), 2.13-2.41 (m, 9H), 2.43-2.77 (m, 1H), 3.07-3.27 (m, 1H), 3.33 (dd, J=14.09, 1.28 Hz, 1H), 4.04 (d, J=14.45 Hz, 1H), 6.47 (s, 1H), 6.65-6.81 (m, 2H), 6.91-7.11 (m, 4H), 7.13-7.36 (m, 5H), 7.85 (s, 1H), 7.92-8.01 (m, 1H).

Example 16(23)

N-(3,5-dimethylphenyl)-1-(3-fluorophenyl)-1,9-dihydrospiro[β-carboline-4,1'-cyclopentane]-2(3H)-carboxamide TLC: Rf 0.34 (hexane:ethyl acetate=4:1);
NMR(CDCl$_3$): δ 1.48-1.64 (m, 1H), 1.67-1.85 (m, 1H), 1.88-2.18 (m, 5H), 2.29 (s, 6H), 2.53-2.78 (m, 1H), 3.13 (d, J=14.27 Hz, 1H), 3.61 (d, J=14.27 Hz, 1H), 6.34 (s, 1H), 6.65-6.82 (m, 2H), 6.92-7.04 (m, 3H), 7.05-7.38 (m, 6H), 7.63 (d, J=7.87 Hz, 1H), 7.97 (s, 1H).

Example 17

2-acetyl-1-(3-fluorophenyl)-1,2,3,9-tetrahydrospiro[β-carboline-4,1'-cyclopropane]

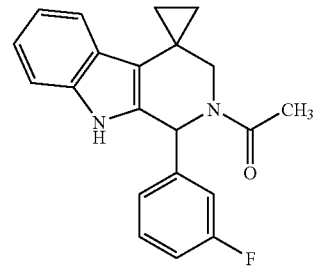

A solution of the compounds prepared in Example 15 (100 mg) in pyridine (2 mL) was added by acetic anhydride (36 μL) and stirred at the room temperature. The reaction mixture was concentrated and the obtained residue was dissolved into ethyl acetate, washed with 0.2N hydrochloric acid and saturated brine successively, dried over anhydrous sodium sulfate and then concentrated. The residue was washed with tert-butylmethylether to give the title compounds (108 mg; beige powder) having the following physical data.

TLC: Rf 0.50 (hexane:ethyl acetate=1:1);
NMR(DMSO-d$_6$): δ 0.74-0.87 (m, 1H), 1.07-1.18 (m, 2H), 1.52-1.68 (m, 1H), 2.12 (s, 3H), 3.29 (d, J=14.65 Hz, 1H), 3.55 (d, J=14.65 Hz, 1H), 6.89 (s, 1H), 6.90-6.96 (m, 1H), 6.96-7.02 (m, 1H), 7.02-7.10 (m, 2H), 7.10-7.20 (m, 1H), 7.25 (d, J=8.06 Hz, 1H), 7.31 (d, J=8.06 Hz, 1H), 7.35-7.47 (m, 1H), 11.09 (s, 1H).

Example 17(1)-Example 17(9)

By the same procedure as described in Example 17 using the corresponding amine derivatives instead of the compounds prepared in Example 15 and acetic anhydride or the corresponding sulfonyl halide derivatives instead thereof, the following compounds in the present invention were obtained.

Example 17(1)

6-methoxy-2-[(3-methylphenyl)sulfonyl]-1-(trifluoromethyl)-2,3,4,9-tetrahydro-1H-β-carboline TLC: Rf 0.39 (hexane:ethyl acetate=3:1);
NMR(CDCl$_3$): δ 2.33 (s, 3H), 2.56 (m, 2H), 3.51 (m, 1H), 3.83 (s, 3H), 4.06 (m, 1H), 5.76 (q, J=6.96 Hz, 1H), 6.84 (d, J=2.38 Hz, 1H), 6.90 (m, if), 7.32 (m, 3H), 7.62 (m, 2H), 7.95 (s, 1H).

Example 17(2)

2-(benzylsulfonyl)-1-(3-fluorophenyl)-2,3,4,9-tetrahydro-1H-β-carboline

TLC: Rf 0.52 (hexane:ethyl acetate=3:1);
NMR(CDCl$_3$): δ 2.84 (m, 2H), 3.13 (m, 1H), 3.83 (m, 1H), 4.02 (d, J=13.91 Hz, 1H), 4.22 (d, J=13.91 Hz, 1H), 5.92 (s, 1H), 7.14 (m, 12H), 7.54 (m, 2H).

Example 17(3)

rac-(1R,3S)-2-acetyl-1-(3-fluorophenyl)-3-methyl-2,3,4,9-tetrahydro-1H-β-carboline TLC: Rf 0.23 (ethyl acetate:hexane=2:3);
NMR(CDCl$_3$): δ 1.12 (d, J=6.96 Hz, 3H), 2.28 (s, 3H), 2.81 (d, J=15.38 Hz, 1H), 3.11 (ddd, J=15.56, 6.32, 1.56 Hz, 1H), 4.46-4.72 (m, 1H), 6.86-7.04 (m, 2H), 7.10-7.29 (m, 5H), 7.32-7.41 (m, 1H), 7.54 (d, J=7.87 Hz, 1H), 7.95 (s, 1H).

Example 17(4)

2-acetyl-1-[3-(trimethylsilyl)phenyl]-2,3,4,9-tetrahydro-1H-β-carboline

TLC: Rf 0.31 (hexane:ethyl acetate=2:1);
NMR(CDCl$_3$): δ 0.23 (s, 9H), 2.20 (s, 3H), 2.81-3.05 (m, 2H), 3.37-3.59 (m, 1H), 3.83-3.98 (m, 1H), 7.02 (s, 1H), 7.09-7.35 (m, 5H), 7.46 (d, J=7.32 Hz, 1H), 7.55 (d, J=7.32 Hz, 1H), 7.63 (s, 1H), 7.74 (s, 1H).

Example 17(5)

rac-(1R,3R)-2-acetyl-1-(3-fluorophenyl)-3-methyl-2,3,4,9-tetrahydro-1H-β-carboline TLC: Rf 0.50 (hexane:ethyl acetate=1:2);
NMR(CDCl$_3$): δ 1.27 (d, J=6.77 Hz, 3H), 2.26 (s, 3H), 2.85-3.01 (m, 1H), 3.26-3.45 (m, 1H), 4.57-4.79 (m, 1H), 5.89 (s, 1H), 6.78-6.90 (m, 1H), 6.98 (d, J=9.52 Hz, 1H), 7.06-7.32 (m, 5H), 7.48-7.56 (m, 1H), 7.67 (s, 1H).

Example 17(6)

2-acetyl-1-(3-fluorophenyl)-4,4-dimethyl-2,3,4,9-tetrahydro-1H-β-carboline

TLC: Rf 0.26 (hexane:ethyl acetate=2:1);
NMR(CDCl$_3$): δ 1.42 (s, 3H), 1.57 (s, 3H), 2.21 (s, 3H), 3.25 (d, J=13.91 Hz, 1H), 3.47 (d, J=13.91 Hz, 1H), 6.91-7.06 (m, 2H), 7.07-7.36 (m, 6H), 7.70 (d, J=8.05 Hz, 1H), 7.83 (s, 1H).

Example 17(7)

2-acetyl-1-(3-fluorophenyl)-3,3-dimethyl-2,3,4,9-tetrahydro-1H-β-carboline

TLC: Rf 0.35 (dichloromethane:ethyl acetate=19:1);
NMR(CDCl$_3$): δ 1.39 (s, 3H), 1.93 (s, 3H), 2.17 (s, 3H), 2.77 (d, J=15.20 Hz, 1H), 2.83 (d, J=15.20 Hz, 1H), 6.07 (s, 1H), 6.86-6.97 (m, 1H), 6.98-7.05 (m, 1H), 7.07-7.33 (m, 4H), 7.37-7.43 (m, 1H), 7.50 (d, J=7.32 Hz, 1H), 8.13 (s, 1H).

Example 17(8)

2-acetyl-1-(3-fluorophenyl)-1,2,3,9-tetrahydrospiro[β-carboline-4,1'-cyclobutane]

TLC: Rf 0.43 (ethyl acetate=1:2);
NMR(CDCl$_3$): δ 1.87-2.09 (m, 1H), 2.08-2.41 (m, 6H), 2.45-2.71 (m, 1H), 3.08-3.27 (m, 1H), 3.33 (d, J=14.09 Hz, 1H), 4.05 (d, J=13.72 Hz, 1H), 6.88-7.40 (m, 8H), 7.83 (s, 1H), 7.91-8.02 (m, 1H).

Example 17(9)

2-acetyl-1-(3-fluorophenyl)-1,2,3,9-tetrahydrospiro[β-carboline-4,1'-cyclopentane]

TLC: Rf 0.28 (hexane:ethyl acetate=2:1);
NMR(CDCl$_3$): δ 1.44-1.62 (m, 1H), 1.63-2.14 (m, 6H), 2.19 (s, 3H), 2.55-2.81 (m, 1H), 3.14 (d, J=13.91 Hz, 1H), 3.62 (d, J=13.91 Hz, 1H), 6.89-7.03 (m, 2H), 7.03-7.39 (m, 6H), 7.63 (d, J=7.50 Hz, 1H), 7.85 (s, 1H).

Example 18-Example 18(7)

By the same procedure as described in Example 8 using the corresponding amine derivatives instead of 2,3,4,9-tetrahydro-1H-β-carboline and the corresponding carbonate derivatives instead of benzylchloridecarbonate, the following compounds in the present invention were obtained.

Example 18 methyl rac-(1R,3S)-1-(3-fluorophenyl)-3-methyl-1,3,4,9-tetrahydrospiro-2H-β-carboline-2-carboxylate TLC: Rf 0.34 (ethyl acetate:hexane=1:5);
NMR(CDCl$_3$): δ 1.11 (d, J=7.14 Hz, 3H), 2.75 (d, J=15.56 Hz, 1H), 3.09 (ddd, J=15.56, 6.59, 2.01 Hz, 1H), 3.78 (s, 3H), 4.96-5.09 (m, 1H), 6.40 (s, 1H), 6.94-7.03 (m, 1H), 7.11-7.36 (m, 6H), 7.51-7.58 (m, 1H), 7.74 (s, 1H).

Example 18(1)

isopropyl rac-(1R,3S)-1-(3-fluorophenyl)-3-methyl-1,3,4,9-tetrahydrospiro-2H-β-carboline-2-carboxylate TLC: Rf 0.44 (ethyl acetate:hexane=1:5);
NMR(CDCl$_3$): δ 1.12 (d, J=7.14 Hz, 2H), 1.21 (d, J=6.22 Hz, 2H), 1.28 (d, J=6.22 Hz, 3H), 2.75 (d, J=15.56 Hz, 1H), 3.09 (ddd, J=15.42, 6.45, 2.11 Hz, 1H), 4.92-5.13 (m, 2H), 6.36 (s, 1H), 6.94-7.03 (m, 1H), 7.11-7.35 (m, 6H), 7.54 (d, J=7.51 Hz, 1H), 7.70 (s, 1H).

Example 18(2)

methyl rac-(1R,3R)-1-(3-fluorophenyl)-3-methyl-1,3,4,9-tetrahydro-2H-β-carboline-2-carboxylate TLC: Rf 0.19 (ethyl acetate:hexane=1:5);
NMR(CDCl$_3$): δ 1.27 (d, J=6.77 Hz, 3H), 2.88 (ddd, J=15.47, 3.48, 1.01 Hz, 1H), 3.20 (ddd, J=15.42, 5.26, 1.10 Hz, 1H), 3.65 (s, 3H), 4.62-4.76 (m, 1H), 5.85 (s, 1H), 6.85-6.95 (m, 1H), 6.96-7.04 (m, 1H), 7.07-7.20 (m, 3H), 7.20-7.30 (m, 2H), 7.52 (dd, J=7.96, 1.19 Hz, 1H), 7.62 (s, 1H).

Example 18(3)

methyl 1-[3-(trimethylsilyl)phenyl]-1,3,4,9-tetrahydro-2H-β-carboline-2-carboxylate TLC: Rf 0.21 (ethyl acetate:hexane=1:5);
NMR(CDCl$_3$): δ 0.25 (s, 9H), 2.75-3.03 (m, 2H), 3.22 (ddd, J=13.55, 11.44, 4.67 Hz, 1H), 3.78 (s, 3H), 4.14-4.62 (m, 1H), 6.17-6.66 (m, 1H), 7.10-7.22 (m, 3H), 7.24-7.31 (m, 2H), 7.45-7.49 (m, 1H), 7.53-7.59 (m, 1H), 7.61 (s, 1H), 7.63-7.72 (m, 1H).

Example 18(4)

isopropyl rac-(1R,3R)-1-(3-fluorophenyl)-3-methyl-1,3,4,9-tetrahydro-2H-β-carboline-2-carboxylate TLC: Rf 0.54 (hexane:ethyl acetate=2:1);
NMR(CDCl$_3$): δ 0.96 (s, 3H), 1.19 (d, J=6.22 Hz, 3H), 1.25 (d, J=6.59 Hz, 3H), 2.82-2.91 (m, 1H), 3.15-3.29 (m, 1H), 4.70-4.95 (m, 2H), 5.79 (s, 1H), 6.83-6.94 (m, 1H), 6.96-7.06 (m, 1H), 7.06-7.18 (m, 3H), 7.18-7.30 (m, 2H), 7.47-7.56 (m, 1H), 7.63 (s, 1H).

Example 18(5)

isopropyl 1-[3-(trimethylsilyl)phenyl]-1,3,4,9-tetrahydro-2H-β-carboline-2-carboxylate TLC: Rf 0.28 (ethyl acetate:hexane=1:5);
NMR(CDCl$_3$): δ 0.25 (s, 9H), 1.29 (d, J=6.04 Hz, 6H), 2.77-3.03 (m, 2H), 3.12-3.28 (m, 1H), 4.12-4.60 (m, 1H), 4.94-5.07 (m, 1H), 6.19-6.69 (m, 1H), 7.09-7.22 (m, 3H), 7.23-7.31 (m, 2H), 7.44-7.49 (m, 1H), 7.53-7.59 (m, 1H), 7.63 (s, 2H).

Example 18(6)

methyl 1-(3-fluorophenyl)-3,3-dimethyl-1,3,4,9-tetrahydro-2H-β-carboline-2-carboxylate TLC: Rf 0.50 (hexane:ethyl acetate=2:1);
NMR(CDCl$_3$): δ 1.36 (s, 3H), 1.78 (s, 3H), 2.87 (s, 2H), 3.71 (s, 3H), 6.28 (s, 1H), 6.83-6.94 (m, 1H), 6.94-7.01 (m, 1H), 7.01-7.08 (m, 1H), 7.09-7.29 (m, 3H), 7.33-7.40 (m, 1H), 7.52 (d, J=7.51 Hz, 1H), 7.99 (s, 1H).

Example 18(7)

isopropyl 1-(3-fluorophenyl)-3,3-dimethyl-1,3,4,9-tetrahydro-2H-β-carboline-2-carboxylate TLC: Rf 0.60 (hexane:ethyl acetate=2:1);
NMR(CDCl$_3$): δ 1.13 (d, J=6.22 Hz, 3H), 1.28 (d, J=6.41 Hz, 3H), 1.38 (s, 3H), 1.79 (s, 3H), 2.87 (s, 2H), 4.92-5.02 (m, 1H), 6.26 (s, 1H), 6.83-6.94 (m, 1H), 6.95-7.02 (m, 1H), 7.02-7.08 (m, 1H), 7.09-7.29 (m, 3H), 7.36 (dd, J=7.60, 1.56 Hz, 1H), 7.52 (d, J=7.32 Hz, 1H), 7.96 (s, 1H).

Example 19

3-fluoro-N-[2-(1H-pyrolo[2,3-b]pyridin-3-yl)ethyl]benzamide

A solution of [2-(1H-pyrolo[2,3-b]pyridin-3-yl)ethyl]amine (86 mg), 1-hydroxybenzotriazol monohydrate (87 mg), 1-ethyl-3-(3-dimethylaminopropyl)carbodiimde monohydrochloride (123 mg) and 3-fluorobenzoic acid in anhydrous dimethylformamide (2 mL) was stirred overnight at the room temperature. The reaction mixture was added by iced water and extracted by ethyl acetate. The organic layer was washed with saturated sodium bicarbonate aqueous solution and saturated brine successively, dried over anhydrous sodium sulfate and then concentrated. The residue was purified by chromatography on silica gel (hexane:ethyl acetate=from 1:1 to 1:2) to give the title compounds (106 mg) having the following physical data.
TLC: Rf 0.26 (hexane:ethyl acetate=1:4);
NMR(CDCl$_3$): δ 3.04-3.13 (m, 2H), 3.79 (q, J=6.65 Hz, 2H), 6.17 (s, 1H), 7.09 (dd, J=7.87, 4.76 Hz, 1H), 7.13-7.23 (m, 2H), 7.29-7.52 (m, 3H), 7.97 (dd, J=7.87, 1.46 Hz, 1H), 8.33 (dd, J=4.76, 1.46 Hz, 1H), 8.99 (s, 1H).

Example 20

8-(3-fluorophenyl)-6,9-dihydro-5H-pyrido[4',3':4,5]pyrolo[2,3-b]pyridine

A mixture of the compounds prepared in Example 19 (70 mg) and phosphoryl chloride (3.0 g) was stirred for 8 hours at the temperature of 120° C. The organic layer was washed with saturated brine, dried over anhydrous sodium sulfate and then concentrated. The residue was purified by column chromatography on silica gel (hexane:ethyl acetate=1:2) to give the title compounds (28 mg) having the following physical data.
TLC: Rf 0.42 (hexane:ethyl acetate=1:4);
NMR(CDCl$_3$): δ 2.91-3.00 (m, 2H), 4.04-4.12 (m, 2H), 7.05 (dd, J=7.96, 4.85 Hz, 1H), 7.18-7.25 (m, 1H), 7.42-7.51 (m, 1H), 7.52-7.58 (m, 1H), 7.58-7.64 (m, 1H), 7.80 (dd, J=4.85, 1.56 Hz, 1H), 7.96 (dd, J=7.96, 1.56 Hz, 1H), 10.33 (s, 1H).

Example 21

8-(3-fluorophenyl)-6,7,8,9-tetrahydro-5H-pyrido[4',3':4,5]pyrolo[2,3-b]pyridine

A solution of the compounds prepared in Example 20 (26 mg) in methanol (2 mL) was gradually added by sodium borohydride (18.6 mg) and stirred at the room temperature. The reaction mixture was concentrated. The residue was dissolved into ethyl acetate and dichloromethane. The organic layer was washed with 1N sodium hydroxide aqueous solution and saturated brine, dried over anhydrous sodium sulfate and then concentrated to give the title compounds (25 mg) having the following physical data. The obtained compounds were used in the next reaction without purification.
TLC: Rf 0.62 (dichloromethane: methanol:28% ammonia water=9:1:0.1);
NMR(CDCl$_3$): δ 2.70-2.94 (m, 2H), 3.07-3.20 (m, 1H), 3.27-3.39 (m, 1H), 5.24 (s, 1H), 6.92 (dd, J=7.69, 4.94 Hz, 1H), 6.98-7.11 (m, 2H), 7.13-7.20 (m, 1H), 7.28-7.38 (m, 1H), 7.53 (dd, J=4.94; 1.56 Hz, 1H), 7.79 (dd, J=7.69, 1.56 Hz, 1H), 11.04 (s, 1H).

Example 22

N-(3,5-dimethylphenyl)-8-(3-fluorophenyl)-5,6,8,9-tetrahydro-7H-pyrido[4',3':4,5]pyrolo[2,3-b]pyridine-7-carboxamide

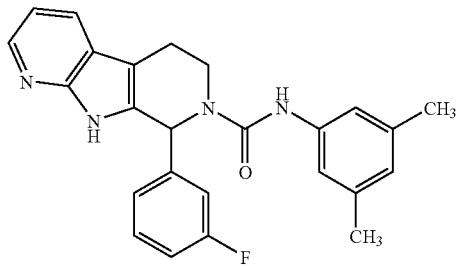

By the same procedure as described in Example 1 using the compounds prepared in Example 21 instead of 2,3,4,9-tetrahydro-1H-β-carboline and 1-isocyanato-3,5-dimethylbenzene instead of 1-isocyanato-3-(trifluoromethyl)benzene, the compound in the present invention having the following physical data were obtained.

TLC: Rf 0.15 (hexane:ethyl acetate=2:1);

NMR(DMSO-d$_6$): δ 2.21 (s, 6H), 2.69-2.96 (m, 2H), 3.06-3.20 (m, 1H), 4.28 (dd, J=14.01, 4.30 Hz, 1H), 6.61 (s, 1H), 6.67 (s, 1H), 6.99-7.20 (m, 6H), 7.36-7.46 (m, 1H), 7.90 (dd, J=7.51, 1.46 Hz, 1H), 8.18 (dd, J=4.67, 1.56 Hz, 1H), 8.61 (s, 1H), 11.55 (s, 1H).

Example 23

7-acetyl-8-(3-fluorophenyl)-6,7,8,9-tetrahydro-5H-pyrido[4',3':4,5]pyrolo[2,3-b]pyridine

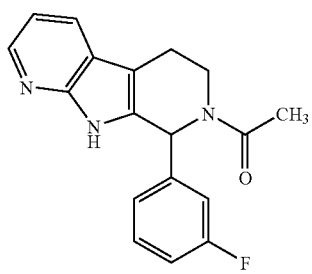

By the same procedure as described in Example 17 using the compounds prepared in Example 21 instead of the compounds prepared in Example 15, the compounds in the present invention having the following physical data were obtained.

TLC: Rf 0.23 (hexane:ethyl acetate=1:1);

NMR(CDCl$_3$): δ 2.22 (s, 3H), 2.78-3.03 (m, 2H), 3.34-3.55 (m, 1H), 3.93 (dd, J=14.45, 4.21 Hz, 1H), 6.92-7.06 (m, 2H), 7.07-7.15 (m, 2H), 7.19 (d, J=7.50 Hz, 1H), 7.22-7.35 (m, 1H), 7.65-7.97 (m, 2H), 11.19 (s, 1H).

Example 24

1-(3-fluorophenyl)-2-(1H-imidazol-1-ylsulfonyl)-2,3,4,9-tetrahydro-1H-β-carboline A solution of 1-(3-fluorophenyl)-2,3,4,9-tetrahydro-1H-β-carboline (150 mg) in acetonitrile (3 mL) was added by 1-(1H-imidazol-1-ylsulfonyl)-3-methyl-1H-imidazol-3-ium trifluoromethansulfonate (270 mg) and triethylamine (307 μL) and stirred at the room temperature. The reaction mixture was concentrated. The residue was dissolved into ethyl acetate, washed with water and saturated brine successively, dried over anhydrous sodium sulfate and then concentrated. The residue was purified by column chromatography on silica gel (hexane:ethyl acetate=2:1) to give the title compounds (54 mg) having the following physical data.

Rf: 0.60 (hexane:ethyl acetate=1:1);

NMR(CDCl$_3$): δ 2.49-2.67 (m, 1H), 2.75-2.85 (m, 1H), 3.35-3.48 (m, 1H), 4.04-4.17 (m, 1H), 6.30 (s, 1H), 6.88 (dd, J=1.65, 0.92 Hz, 1H), 6.92-7.00 (m, 2H), 7.00-7.40 (m, 6H), 7.47 (d, J=7.69 Hz, 1H), 7.78 (dd, J=1.28, 0.92 Hz, 1H), 7.85 (s, 1H).

Example 25

1-{[1-(3-fluorophenyl)-1,3,4,9-tetrahydro-2H-β-carbolin-2-yl]sulfonyl}-3-methyl-1H-imidazol-3-ium trifluoromethanesulfonate The compounds prepared in Example 24 (50 mg) were dissolved into dichloromethane (2 mL) and chloroform (2 mL), added by methyl trifluoromethanesulfonate (14.3 μL) under the ice and stirred for 1 hour. The reaction mixture was concentrated to give the title compounds having the following physical data. The obtained compounds were used in the next reaction without purification.

TLC: Rf 0.57 (butanol:ethyl acetate:water=4:2:1);

NMR(CDCl$_3$): δ 2.58-2.93 (m, 2H), 3.34 (s, 3H), 3.43-3.67 (m, 1H), 4.11-4.27 (m, 1H), 6.69 (s, 1H), 6.75-6.83 (m, 1H), 6.92-7.00 (m, 1H), 7.01-7.15 (m, 3H), 7.17-7.29 (m, 1H), 7.28-7.41 (m, 2H), 7.42-7.56 (m, 2H), 9.52 (s, 1H), 10.04 (s, 1H).

Example 26

N-(3,5-dimethylphenyl)-1-(3-fluorophenyl)-1,3,4,9-tetrahydro-2H-β-carboline-2-sulfonamide

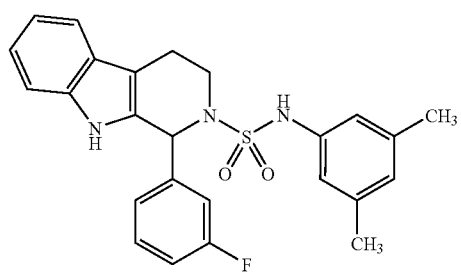

A solution of the compounds prepared in Example 25 in acetonitrile (3 mL) was added by 3,5-dimethylaniline (16 μL)

and stirred overnight at the temperature of 65° C., for 8 hours at the temperature of 85° C. The reaction mixture was cooled down to the room temperature and then concentrated. The residue was purified by column chromatography on silica gel (hexane:ethyl acetate=2:1) to give the title compounds (22 mg) to give the title compounds having the following physical data.

TLC: Rf 0.72 (hexane:ethyl acetate=2:1);

NMR(CDCl$_3$): δ 2.00 (s, 6H), 2.73 (m, 2H), 3.21 (m, if), 3.98 (m, 1H), 6.07 (s, 1H), 6.10 (s, 1H), 6.44 (s, 2H), 6.61 (s, 1H), 7.10 (m, 7H), 7.47 (d, J=7.69 Hz, 1H), 7.57 (s, 1H).

Biological Example 1

Receptor Binding Experiment

The affinity of the compounds in the present invention to MBR was determined using rat brain membrane preparation. In addition, the measurement in the present invention was improved the accuracy of measurement and the sensitivity of measurement for evaluating the compounds in the present invention as follows. After male Wister rats were decapitated to extirpate the whole brain and cerebellums were removed. They were homogenized in ice-cold 50 mmol/L Tris-HCL buffer solution (pH7.4), centrifuged and the obtained pellets were washed. The pellets resuspended and adjusted to about 1 mg/mL were used as rat brain membrane preparations for binding assay. The binding assay were experimented using [$^3$H]PK11195 as a MBR selective ligand. In addition, PK11195 was described in "European Journal of Pharmacology, 119, 153-167, 1985" as a MBR selective ligand, (1-(2-chlorophenyl)-N-methyl-N-(1-methylpropyl)-3-isoquinolinecarboxamide).

To determine the amount of total binding in saturation binding experiment, membrane preparations, various concentrations of [$^3$H]PK11195, final concentration: 0.5 vol % dimethylsulfoxide (DMSO) and 50 mmol/L Tris-HCL buffer solution (pH7.4) were mixed (total volume 200 µL) and were incubated for 1 hour at room temperature. To determine the amount of non-specific binding, the mixture was added by final concentration 20 µmol/L of PK11195 instead of DMSO to be incubated for 1 hour. The mixture was rapidly filtrated on GF/B filter pretreated with 0.3% polyethyleneimine using cell harvester and washed over 50 mmol/L Tris-HCl buffer solution (pH7.4) twice. The filter was dried and then the radioactivity on the filter was measured by liquid scintillation counter. The data obtained by the binding experiments were Scatchard-analyzed using analysis software, KELL (Ver. 6, BIOSOFT) and the dissociation constant ($K_D$ value) was determined.

To determine the amount of total binding in competition binding experiment, membrane preparations or 1 nmol/L [$^3$H]PK11195, final concentration: 0.5 vol % dimethylsulfoxide (DMSO) and 50 mmol/L Tris-HCL buffer solution (pH7.4) were mixed (total volume 200 µL) and were incubated for 1 hour at room temperature. To determine the amount of non-specific binding, the mixture was added by final concentration 20 µmmol/L of PK11195 instead of DMSO to be incubated for 1 hour. In addition, to determine the affinity of the compounds in the present invention, the mixture was added by final concentration 10 pmol/L to 1 µmol/L of the solution of the compounds in the present invention in DMSO instead of DMSO to be incubated. After 1 hour, the mixture was saction filtrated by the above-mentioned method and the radioactivity on the filter was measured by liquid scintillation counter. The concentration of the compounds in the present invention ($IC_{50}$) which was necessary for inhibiting the amount of specific binding by 50% was determined from the obtained data. The inhibition constant ($K_i$ value) was calculated according to Cheng and Prusoff formula (Biochemical Pharmacolgy, 22, 3099-3108, 1973) using $K_D$ value and $IC_{50}$.

In consequence, it was clear that the compounds in the present invention had high affinity to MBR.

For example, $K_i$ value of the compounds of Example 17 was 21 nM.

Biological Example 2

Evaluation of Anti-Stress Effects

Psychological stress was loaded to male Wistar rats (*Brain Research*, 641, 21-28, 1994). Water was stored up to the depth of about 10 cm in a container where the platform was set at the center. A stressor began to load to rats 30 minutes after the vehicle or the compound in the present invention (the compound of Example 17) were orally administered by dosage of 10 mg/kg. The number of defecation was counted 1 hour later (10 per each group). Rats without administration and load of stressor rarely defecated for 1 hour. In contrast, remarkable defecation was admitted in media treated group (average 8.0 feces) loaded by stressor. However, it proved that the compound in the present invention controlled the number of defecation (average 5.4 feces) more significantly than that of media treated group. The results clarified that the compounds in the present invention had anti-stress effects.

Preparation Example 1

The following components were admixed in conventional method, punched out to give 10000 tablets each containing 10 mg of active ingredient.

| | |
|---|---|
| N-[3-(trifluoromethyl)phenyl]-1,3,4,9-tetrahydro-2H-β-carboline-2-carboxamide | 100 g |
| carboxymethylcellulosecalcium (disintegrant) | 20.0 g |
| magnesium stearate (lubricant) | 10.0 g |
| microcrystalline cellulose | 870 g |

Preparation Example 2

After mixing the following components by a conventional method, the resulting solution was filtrated by dust-proof filter and 5 mL portions thereof were filled in amples, respectively, and heat-sterilized by autoclave to obtain 10000 amples of injection containing each 20 mg of the active ingredient.

| | |
|---|---|
| N-[3-(trifluoromethyl)phenyl]-1,3,4,9-tetrahydro-2H-β-carboline-2-carboxamide | 200 g |
| mannitol | 2 kg |
| distilled water | 50 L |

The invention claimed is:

1. A compound represented by formula (I-3-4):

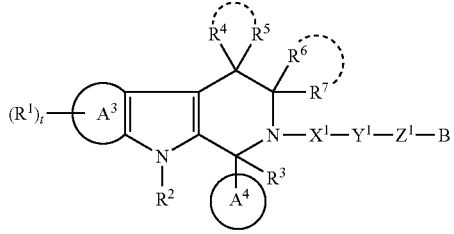

(I-3)

wherein, ring $A^3$ is benzene, pyridine, pyrimidine or pyrazine;

ring $A^4$ is benzene which may be substituted with 1 to 4 substituent(s) optionally selected from C1-8 alkyl, C2-8 alkenyl, C2-8 alkynyl, hydroxyl, C1-8 alkoxy, amino, $NR^{104}R^{105}$, carboxyl, C1-6 alkoxycarbonyl, nitro, cyano, a halogen atom, oxo, acyl, formyl and tri(C1-6 alkyl)silyl;

$R^{104}$ and $R^{105}$ are each independently a hydrogen atom or C1-8 alkyl;

$R^1$ is C1-8 alkyl, C2-8 alkenyl, C2-8 alkynyl, hydroxyl, C1-8 alkoxy, mercapto, C1-8 alkylthio, amino, $NR^{104}R^{105}$, C1-6 alkoxycarbonyl, nitro, cyano, a halogen atom, oxo, acyl, formyl or tri(C1-6 alkyl)silyl;

$R^2$, $R^3$, $R^6$ and $R^7$ represent a hydrogen atom;

$R^4$ and $R^5$ are together with their binding carbon atom to form C3-8 cycloalkyl;

$X^1$ and $Z^1$ represent a single bond;

$Y^1$ is —C(=O)—, —C(=O)$NR^{103}$—, —$SO_2$—, —C(=O)O— or $SO_2NR^{103}$;

$R^{103}$ is a hydrogen atom;

B is C1-8 alkyl, C2-8 alkenyl or C2-8 alkynyl which may be substituted with 1 to 4 substituent(s) optionally selected from hydroxyl, mercapto, amino, carboxyl, nitro, cyano, mono- or di-C1-6 alkylamino, C1-6 alkoxy, C1-6 alkylcarbonyloxy, C1-6 alkylthio, a halogen atom, acyl, or benzene which may be substituted with 1 to 4 substituent(s) optionally selected from C1-8 alkyl, C2-8 alkenyl, C2-8 alkynyl, hydroxyl, C1-8 alkoxy, amino, $NR^{104}R^{105}$, carboxyl, C1-6 alkoxycarbonyl, nitro, cyano, a halogen atom, oxo, acyl, formyl and tri(C1-6 alkyl)silyl; and t is 0 or an integer 1 to 5, a salt thereof.

2. The compound according to claim 1, wherein ring $A^3$ is a benzene; $Y^1$ is —C(=O)— or —C(=O)$NR^{103}$.

3. The compound according to claim 1, which is selected from (1) N-(3,5-dimethylphenyl)-1-(3-fluorophenyl)-1,9-dihydrospiro[β-carboline-4,1'-cyclopropane]-2(3H)-carboxamide, and (2) 2-acetyl-1-(3-fluorophenyl)-1,2,3,9-tetrahydrospiro [β-carboline-4,1'-cyclopropane].

4. A pharmaceutical composition comprising the compound represented by formula (I-3-4) according to claim 1, a salt thereof.

5. A method for treatment for irritable bowel syndrome in a mammal, which comprises administering an effective amount of the compound represented by formula (I-3-4) according to claim 1, or a salt thereof, to a mammal in need thereof.

* * * * *

UNITED STATES PATENT AND TRADEMARK OFFICE
CERTIFICATE OF CORRECTION

| | | |
|---|---|---|
| PATENT NO. | : 7,872,133 B2 | Page 1 of 1 |
| APPLICATION NO. | : 10/561973 | |
| DATED | : January 18, 2011 | |
| INVENTOR(S) | : Kazuyuki Ohmoto et al. | |

It is certified that error appears in the above-identified patent and that said Letters Patent is hereby corrected as shown below:

Please amend the title as follows.

TRICYCLIC ~~HETEROCYCLE~~ <u>HETEROCYCLIC RING</u> COMPOUND

Signed and Sealed this
Ninth Day of August, 2011

David J. Kappos
*Director of the United States Patent and Trademark Office*

UNITED STATES PATENT AND TRADEMARK OFFICE
CERTIFICATE OF CORRECTION

PATENT NO.         : 7,872,133 B2
APPLICATION NO.    : 10/561973
DATED              : January 18, 2011
INVENTOR(S)        : Kazuyuki Ohmoto et al.

It is certified that error appears in the above-identified patent and that said Letters Patent is hereby corrected as shown below:

Title Page, Item (54) and at Column 1, line 1,

Please amend the title as follows.

TRICYCLIC ~~HETEROCYCLE~~ HETEROCYCLIC RING COMPOUND

This certificate supersedes the Certificate of Correction issued August 9, 2011.

Signed and Sealed this
Thirtieth Day of August, 2011

David J. Kappos
*Director of the United States Patent and Trademark Office*